United States Patent
Sakamoto et al.

(10) Patent No.: US 12,359,000 B2
(45) Date of Patent: Jul. 15, 2025

(54) ANTI-8-HYDROXY-2'-DEOXYGUANOSINE ANTIBODY OR ANTIBODY FRAGMENT THEREOF, PRODUCTION METHOD, KIT, MEASURING METHOD, AND DEVICE FOR MEASUREMENT

(71) Applicant: TDK CORPORATION, Tokyo (JP)

(72) Inventors: Takeshi Sakamoto, Tokyo (JP); Hiroko Yanagisawa, Osaka (JP); Toshiaki Maruyama, San Diego, CA (US); Shigeru C J Okumura, San Diego, CA (US)

(73) Assignee: TDK CORPORATION, Tokyo (JP)

( * ) Notice: Subject to any disclaimer, the term of this patent is extended or adjusted under 35 U.S.C. 154(b) by 628 days.

(21) Appl. No.: 17/626,755

(22) PCT Filed: Oct. 6, 2020

(86) PCT No.: PCT/JP2020/037883
§ 371 (c)(1),
(2) Date: Jan. 12, 2022

(87) PCT Pub. No.: WO2021/100342
PCT Pub. Date: May 27, 2021

(65) Prior Publication Data
US 2022/0372119 A1 Nov. 24, 2022

Related U.S. Application Data

(60) Provisional application No. 62/939,076, filed on Nov. 22, 2019.

(51) Int. Cl.
| | | |
|---|---|---|
| *C07K 16/44* | (2006.01) | |
| *C12N 5/10* | (2006.01) | |
| *C12N 15/63* | (2006.01) | |
| *G01N 33/53* | (2006.01) | |
| *C07K 16/18* | (2006.01) | |

(52) U.S. Cl.
CPC .............. *C07K 16/44* (2013.01); *C12N 5/10* (2013.01); *C12N 15/63* (2013.01); *G01N 33/5308* (2013.01); *C07K 16/18* (2013.01); *C07K 2317/20* (2013.01); *C07K 2317/33* (2013.01); *C07K 2317/565* (2013.01); *C07K 2317/567* (2013.01); *G01N 33/53* (2013.01)

(58) Field of Classification Search
CPC ........ C07K 16/18; C07K 16/44; G01N 33/53; G01N 33/5308
See application file for complete search history.

(56) References Cited

FOREIGN PATENT DOCUMENTS

| | | |
|---|---|---|
| JP | H04-135484 A | 5/1992 |
| JP | 3091974 B2 | 9/2000 |
| JP | 2006-056859 A | 3/2006 |

OTHER PUBLICATIONS

Benjamini et al, 1991. Immunology: A Short Course, 2nd edition, p. 40 only.*
Ferrara et al (2015. mAbs. 7(1): 32-41).*
Aug. 23, 2022 Decision to Grant a Patent issued in Japanese Patent Application No. 2021-558206.
Song et al., "Urea, the most abundant component in urine, cross-reacts with a commercial 8-OH-dG ELISA kit and contributes to overestimation of urinary 8-OH-dG," Free Radical Biology & Medicine, 2009, vol. 47, pp. 41-46.
Toyokuni et al., "Quantitative Immunohistochemical Determination of 8-Hydroxy-2'-Deoxyguanosine by a Monoclonal Antibody, N45. 1: Its Application to Ferric Nitrilotriacetate-Induced Renal Carcinogenesis Model," Laboratory Investigation, Mar. 1997, vol. 76, No. 3, pp. 365-374.
Wu et al., "Urinary 8-OHdG: a marker of oxidative stress to DNA and a risk factor for cancer, atherosclerosis and diabetics," Clinica Chimica Acta, 2004, vol. 339, pp. 1-9.
Park et al., "Assay of excised oxidative DNA lesions: Isolation of 8-oxoguanine and its nucleoside derivatives from biological fluids with a monoclonal antibody column," Proc. Natl. Acad. Sci. USA, Apr. 1992, vol. 89, pp. 3375-3379.
Dec. 22, 2020 International Search Report issued in International Patent Application No. PCT/JP2020/037883.
May 10, 2022 Translation of Office Action issued in Japanese Patent Application No. 2021-558206.

* cited by examiner

*Primary Examiner* — Zachary C Howard
(74) *Attorney, Agent, or Firm* — Oliff PLC

(57) ABSTRACT

An anti-8-OHdG antibody and an antibody fragment thereof, with which 8-hydroxy-2'-deoxyguanosine (8-OHdG) in a specimen, particularly urine, can be accurately analyzed, and a measuring method capable of measuring 8-OHdG in a specimen, particularly urine, with high sensitivity are provided. An anti-8-OHdG antibody or an antibody fragment thereof which reacts specifically with 8-OHdG and substantially does not react with urea; the antibody or antibody fragment thereof in which the complementarity-determining regions of the variable regions of heavy and light chains are specific amino acid sequences; and a measuring method for 8-OHdG in a specimen using the antibody or antibody fragment thereof are disclosed.

20 Claims, 8 Drawing Sheets
Specification includes a Sequence Listing.

ANTI-8-HYDROXY-2'-DEOXYGUANOSINE ANTIBODY OR ANTIBODY FRAGMENT THEREOF, PRODUCTION METHOD, KIT, MEASURING METHOD, AND DEVICE FOR MEASUREMENT

Priority is claimed on U.S. Provisional Patent Application No. 62/939,076, filed Nov. 22, 2019, the content of which is incorporated herein by reference.

TECHNICAL FIELD

The present invention relates to an anti-8-hydroxy-2'-deoxyguanosine (hereinafter, also referred to as 8-OHdG) antibody or an antibody fragment thereof, a nucleic acid encoding the antibody or the antibody fragment thereof, a vector containing a nucleic acid, an antibody-producing cell containing the vector, a method for producing the antibody or the antibody fragment thereof, an immunological measuring method of the antibody or the antibody fragment thereof, a kit including the antibody or the antibody fragment thereof, and a device including the antibody or the antibody fragment thereof.

BACKGROUND ART

The atmosphere includes about 20% oxygen, and living organisms utilize this oxygen to maintain their vital activities. Oxygen receives various external stimuli and changes into a highly reactive oxygen species having high reactivity. The reactive oxygen species acts as a transmitter between cells and has an immune function, while excessive production injures cells. Since the living body is equipped with an antioxidant defense mechanism that suppresses the production of reactive oxygen species and promotes the repair and regeneration of damage caused by the injury made by reactive oxygen species, homeostasis in the body can usually be maintained.

Oxidative stress is defined as a state in which the production of reactive oxygen species exceeds the antioxidant defense mechanism in the living body and the balance is lost. Oxidative stress acts harmfully on the living body and causes various diseases including cancer, cardiovascular disease, various lifestyle-related diseases such as diabetes, and Alzheimer's disease, as well as aging. It has also been pointed out that oxidative stress is related to mental stress.

It has been expected to prevent diseases and aging caused by oxidative stress, by measuring the oxidative stress. Furthermore, utilization of the measurement of oxidative stress for screening tests to detect potential diseases may be considered.

Regarding a method for measuring oxidative stress, various methods have been studied and put into practical use. These methods include an electron spin resonance method (ESR) of measuring superoxide ($\cdot O^{2-}$, hydroxyl radical ($\cdot OH$), and the like, which are reactive oxygen species present in blood and cells; a method of measuring hydrogen peroxide ($H_2O_2$), which is one of the reactive oxygen species, by color comparison of Xylenol Orange; a method of measuring the reactive oxygen species by a color reaction with an aromatic amine N,N-diethylparaphenylenediamine; and the like. Since reactive oxygen species cause injury to cells, there is also a method of detecting substances generated at that time. For example, methods for measuring hydroxylinoleic acid (HODE), linoleic acid peroxide, and 8-isoprostaglandin, which are lipid peroxides generated by disorders in the cell membranes and lipids, protein-derived nitrotyrosine, 8-OHdG produced by DNA degradation, 8-nitroguanosine, and the like are available. In addition to those, there are also methods for measuring antioxidant enzymes such as superoxide dismutase, catalase, and glutathione peroxidase; antioxidants such as glutathione and bilirubin; and the like.

Among them, 8-OHdG is an oxidative stress marker that is used most. Patent Document 1 discloses an anti-8-OHdG monoclonal antibody and a hybridoma producing the same. Regarding a method for measuring the 8-OHdG concentration, high-performance liquid chromatography and enzyme-linked immuno-sorbent assay (hereinafter, also referred to as ELISA) have been put into practical use. Anti-8-OHdG antibodies for ELISA have also been developed, and for example, N45.1 and the like have been commercially used for a long period of time. Non-Patent Document 1 shows an evaluation of the specificity of N45.1 to 8-OHdG.

However, Non-Patent Document 2 shows the results obtained for the specificity of the anti-8-OHdG antibody N45.1 by evaluating the cross-reactivity with various analogs of 8-OHdG by ELISA, and among the analogs, the cross-reactivity with 8-OHG and 8-mercaptoguanosine (hereinafter, also referred to as 8-SHG) has been recognized.

Furthermore, Non-Patent Document 2 shows the results obtained for the specificity of the anti-8-OHdG antibody N45.1 by evaluating the specificity to urea at the concentration at which urea is included in urine by ELISA, and N45.1 has been recognized to have cross-reactivity with urea at the concentration at which urea is included in urine.

Non-Patent Document 3 shows a comparison of the results obtained by measuring the 8-OHdG concentration in human urine by high-performance liquid chromatography (HPLC) and ELISA. The measured value of the 8-OHdG concentration in human urine obtained by ELISA shows a value that is about twice or more compared to the measured value obtained by HPLC, and it has been shown that fluctuation is large.

CITATION LIST

Patent Document

[Patent Document 1]
  Japanese Patent No. 3091974

Non-Patent Documents

[Non-Patent Document 1]
  Song, et. al., Free Radical Biology & Medicine, 47, (2009), 41
[Non-Patent Document 2]
  Toyokuni, et. al., Lab. Invest. 76, (1997), 365
[Non-Patent Document 3]
  Wu, et. al., Clinica Chimica Acta 339, (2004), 1

DISCLOSURE OF INVENTION

Technical Problem

Detection of biological substances has been carried out in the fields of medical care, healthcare, environment, and the like. Thus, it is desirable to develop an analysis method capable of selectively quantifying, with high sensitivity and simple operability, a biological substance as an object of measurement from a plurality of biological substances.

As one of the methods capable of selectively measuring a trace amount of a biological substance in a specimen with high sensitivity, an immunoassay method is known. An immunoassay method is a method for quantifying an antigen by utilizing a reaction (antigen-antibody reaction) between a biological substance (antigen, hapten, or the like) as an object of measurement and a substance binding to the antigen (antibody).

An immunoassay method can specifically detect a particular biological substance from a plurality of biological substances; however, what determines the specificity of the immunoassay method is the antibody or a fragment thereof that is used therein. That is, the specificity of the antibody or a fragment thereof itself determines the accuracy of the immunoassay method.

However, conventional antibodies that specifically bind to 8-hydroxy-2'-deoxyguanosine (8-OHdG) in urine certainly have specificity; however, such an antibody is affected by urea at the concentration at which the urea is included in urine, so that the concentration of 8-OHdG could not be measured accurately by the antibody. Furthermore, since the antibodies also react with analogs such as 8-mercaptoguanosine (8-SHG), it cannot be said that the antibodies have perfect specificity. As has been pointed out in Non-Patent Document 2, especially when the 8-OHdG concentration in urine is measured by ELISA using a conventional antibody, there has been a problem in that the concentration shows a high value compared to HPLC, and the fluctuation is large.

The present invention was achieved in view of the above-described problems, and an object of the present invention is to provide, in order to more accurately analyze 8-OHdG in a specimen, particularly urine, an antibody and an antibody fragment thereof having high selectivity and specificity without being affected by analogs or urea at the concentration at which urea is included in urine, and a measurement method capable of measuring 8-OHdG in a specimen, particularly urine, with high sensitivity.

Solution to Problem

The inventors of the present invention found an anti-8-hydroxy-2'-deoxyguanosine antibody that specifically reacts with 8-hydroxy-2'-deoxyguanosine and substantially does not react with urea, and determined complementarity-determining regions (hereinafter, also referred to as CDRs) of a heavy chain variable region (hereinafter, also referred to as VH) and a light chain variable region (hereinafter, also referred to as VL), and a Framework region (hereinafter, also referred to as FR). Furthermore, the inventors found that 8-OHdG in urine can be accurately measured by the antibody, without being affected by urea, thus completing the present invention.

That is, the present invention provides the following means in order to solve the above-described problems.

(1) An anti-8-OHdG antibody or an antibody fragment thereof according to a first aspect reacts specifically with 8-OHdG and substantially does not react with urea.

(2) With regard to the antibody or the antibody fragment thereof according to the above-described embodiment, a concentration of urea that inhibits an immune response between the antibody or the antibody fragment thereof and 8-OHdG by 50% may be 30 mg/mL or more.

(3) With regard to the antibody or the antibody fragment thereof according to the above-described embodiment, a concentration of 8-mercaptoguanosine (hereinafter, also referred to as 8-SHG) that inhibits an immune response between the antibody or the antibody fragment thereof and 8-OHdG by 50% may be 100 or more times the concentration of 8-OHdG that inhibits the immune response by 50%.

(4) With regard to the antibody or the antibody fragment thereof according to the above-described embodiment, an amino acid sequence of CDR2 of the antibody or the antibody fragment thereof may include an amino acid sequence set forth in SEQ ID NO:1, an amino acid sequence of CDR3 of a VH may include an amino acid sequence set forth in SEQ ID NO:2 or an amino acid sequence in which the 8th isoleucine of SEQ ID NO:2 is substituted with valine, an amino acid sequence of CDR1 of a light chain variable region (hereinafter, also referred to as VL) of the antibody or the antibody fragment thereof may include an amino acid sequence set forth in SEQ ID NO:3, and an amino acid sequence of CDR3 of the VL may include an amino acid sequence set forth in SEQ ID NO:4.

(5) With regard to the antibody or the antibody fragment thereof according to the above-described embodiment, an amino acid sequence of CDR1 of a VH of the antibody or the antibody fragment thereof may include any one amino acid sequence selected from the group consisting of an amino acid sequence set forth in SEQ ID NO:11, an amino acid sequence in which the 4th leucine of SEQ ID NO:11 is substituted with proline, and an amino acid sequence in which the 5th serine of SEQ ID NO:11 is substituted with methionine;

an amino acid sequence of CDR2 of the VH may include any one amino acid sequence selected from the group consisting of an amino acid sequence set forth in SEQ ID NO:6, an amino acid sequence in which the 6th asparagine of SEQ ID NO:6 is substituted with histidine or phenylalanine, an amino acid sequence in which the 7th isoleucine of SEQ ID NO:6 is substituted with valine, and an amino acid sequence in which the 6th asparagine of SEQ ID NO:6 is substituted with threonine and the 7th isoleucine is substituted with leucine;

an amino acid sequence of CDR3 of the VH may include any one amino acid sequence selected from the group consisting of an amino acid sequence set forth in SEQ ID NO:7, an amino acid sequence in which the 4th valine of SEQ ID NO:7 is substituted with isoleucine, and an amino acid sequence in which the 12th isoleucine of SEQ ID NO:7 is substituted with valine;

an amino acid sequence of CDR1 of the VL may include any one amino acid sequence selected from the group consisting of an amino acid sequence set forth in SEQ ID NO:8 and an amino acid sequence in which the 5th serine of SEQ ID NO:8 is substituted with asparagine or glycine;

an amino acid sequence of CDR2 of the VL may include an amino acid sequence set forth in SEQ ID NO:9; and an amino acid sequence of CDR3 of the VL may include any one amino acid sequence selected from the group consisting of an amino acid sequence set forth in SEQ ID NO:10, an amino acid sequence in which the 8th serine of SEQ ID NO:10 is substituted with tyrosine, and an amino acid sequence in which the 8th serine of SEQ ID NO:10 is substituted with tyrosine and the 9th glycine is substituted with serine.

(6) With regard to the antibody or the antibody fragment thereof according to the above-described embodiment, the antibody or the antibody fragment thereof may be any one antibody or antibody fragment thereof selected from the group consisting of the following (a) to (i) and (A) to (C):

(a) an antibody or an antibody fragment thereof in which:
the amino acid sequence of CDR1 of the VH includes an amino acid sequence set forth in SEQ ID NO:5,
the amino acid sequence of CDR2 of the VH includes the amino acid sequence set forth in SEQ ID NO:6,
the amino acid sequence of CDR3 of the VH includes the amino acid sequence set forth in SEQ ID NO:7,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(b) an antibody or an antibody fragment thereof in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes the amino acid sequence set forth in SEQ ID NO:7,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(c) an antibody or an antibody fragment thereof in which:
the amino acid sequence of CDR1 of the VH includes the amino acid sequence set forth in SEQ ID NO:11,
the amino acid sequence of CDR2 of the VH includes an amino acid sequence set forth in SEQ ID NO:12,
the amino acid sequence of CDR3 of the VH includes the amino acid sequence set forth in SEQ ID NO:7,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(d) an antibody or an antibody fragment thereof in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes an amino acid sequence set forth in SEQ ID NO:13,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes an amino acid sequence set forth in SEQ ID NO:14;

(e) an antibody or an antibody fragment thereof in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes an amino acid sequence set forth in SEQ ID NO:13,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes an amino acid sequence set forth in SEQ ID NO:15;

(f) an antibody or an antibody fragment thereof in which:
the amino acid sequence of CDR1 of the VH includes the amino acid sequence set forth in SEQ ID NO:11,
the amino acid sequence of CDR2 of the VH includes an amino acid sequence set forth in SEQ ID NO:16,
the amino acid sequence of CDR3 of the VH includes an amino acid sequence set forth in SEQ ID NO:13,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(g) an antibody or an antibody fragment thereof in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes an amino acid sequence set forth in SEQ ID NO:13,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(h) an antibody or an antibody fragment thereof in which:
the amino acid sequence of CDR1 of the VH includes an amino acid sequence set forth in SEQ ID NO:17,
the amino acid sequence of CDR2 of the VH includes the amino acid sequence set forth in SEQ ID NO:6,
the amino acid sequence of CDR3 of the VH includes the amino acid sequence set forth in SEQ ID NO:7,
the amino acid sequence of CDR1 of the VL includes an amino acid sequence set forth in SEQ ID NO:18,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(i) an antibody or an antibody fragment thereof in which:
the amino acid sequence of CDR1 of the VH includes the amino acid sequence set forth in SEQ ID NO:11,
the amino acid sequence of CDR2 of the VH includes an amino acid sequence set forth in SEQ ID NO:19,
the amino acid sequence of CDR3 of the VH includes an amino acid sequence set forth in SEQ ID NO:13,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(A) an anti-8-OHdG antibody or an antibody fragment thereof in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes the amino acid sequence set forth in SEQ ID NO:7,
the amino acid sequence of CDR1 of the VL includes an amino acid sequence set forth in SEQ ID NO:69,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(B) an anti-8-OHdG antibody or an antibody fragment thereof in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes an amino acid sequence set forth in SEQ ID NO:70,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;
(C) an anti-8-OHdG antibody or an antibody fragment thereof in which:
the amino acid sequence of CDR1 of the VH includes the amino acid sequence set forth in SEQ ID NO:11,
the amino acid sequence of CDR2 of the VH includes an amino acid sequence set forth in SEQ ID NO:71,
the amino acid sequence of CDR3 of the VH includes the amino acid sequence set forth in SEQ ID NO:7,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(7) With regard to the antibody or the antibody fragment thereof according to the above-described embodiment, an amino acid sequence of FR1 of a VH of the antibody or the antibody fragment thereof may include an amino acid sequence set forth in SEQ ID NO:20,
an amino acid sequence of FR2 of the VH may include amino acid sequences set forth in SEQ ID NO:21 and SEQ ID NO:22,
an amino acid sequence of FR3 of the VH may include an amino acid sequence set forth in SEQ ID NO:23,
an amino acid sequence of FR4 of the VH may include amino acid sequences set forth in SEQ ID NO:24 and SEQ ID NO:25,
an amino acid sequence of FR1 of a VL of the antibody or the antibody fragment thereof may include an amino acid sequence set forth in SEQ ID NO:26,
an amino acid sequence of FR2 of the VL may include an amino acid sequence set forth in SEQ ID NO:27,
an amino acid sequence of FR3 of the VL may include amino acid sequences set forth in SEQ ID NO:28 and SEQ ID NO:29, and
an amino acid sequence of FR4 of the VL may include an amino acid sequence set forth in SEQ ID NO:30.

(8) With regard to the antibody or the antibody fragment thereof according to the above-described embodiment, the amino acid sequence of FR1 of a VH of the antibody or the antibody fragment thereof may include an amino acid sequence set forth in any one of SEQ ID NO:31 to SEQ ID NO:41 and SEQ ID NO:72,
the amino acid sequence of FR2 of the VH may include an amino acid sequence set forth in any one of SEQ ID NO:42 to SEQ ID NO:45,
the amino acid sequence of FR3 of the VH may include an amino acid sequence set forth in any one of SEQ ID NO:46 to SEQ ID NO:49,
the amino acid sequence of FR4 of the VH may include an amino acid sequence set forth in SEQ ID NO:50 or SEQ ID NO:51,
the amino acid sequence of FR1 of a VL of the antibody or the antibody fragment thereof may include an amino acid sequence set forth in any one of SEQ ID NO:52 to SEQ ID NO:59,
the amino acid sequence of FR2 of the VL may include an amino acid sequence set forth in any one of SEQ ID NO:60 to SEQ ID NO:62,
the amino acid sequence of FR3 of the VL may include an amino acid sequence set forth in any one of SEQ ID NO:63 to SEQ ID NO:68, and
an amino acid sequence of FR4 of the VL may include an amino acid sequence set forth in SEQ ID NO:30.

(9) With regard to the antibody or the antibody fragment thereof according to the above-described embodiment, the antibody or the antibody fragment thereof may be any one antibody or antibody fragment thereof selected from the group consisting of following (j) to (z) and (D) to (I):
(j) an antibody or an antibody fragment thereof in which:
the amino acid sequence of FR1 of the VH includes an amino acid sequence set forth in SEQ ID NO:31,
the amino acid sequence of FR2 of the VH includes an amino acid sequence set forth in SEQ ID NO:44,
the amino acid sequence of FR3 of the VH includes an amino acid sequence set forth in SEQ ID NO:46,
the amino acid sequence of FR4 of the VH includes an amino acid sequence set forth in SEQ ID NO:50,
the amino acid sequence of FR1 of the VL includes an amino acid sequence set forth in SEQ ID NO:52,
the amino acid sequence of FR2 of the VL includes an amino acid sequence set forth in SEQ ID NO:60,
the amino acid sequence of FR3 of the VL includes an amino acid sequence set forth in SEQ ID NO:63, and
the amino acid sequence of FR4 of the VL includes the amino acid sequence set forth in SEQ ID NO:30;
(k) an antibody or an antibody fragment thereof in which:
the amino acid sequence of FR1 of the VH includes an amino acid sequence set forth in SEQ ID NO:32,
the amino acid sequence of FR2 of the VH includes an amino acid sequence set forth in SEQ ID NO:44,
the amino acid sequence of FR3 of the VH includes an amino acid sequence set forth in SEQ ID NO:47,
the amino acid sequence of FR4 of the VH includes an amino acid sequence set forth in SEQ ID NO:50,
the amino acid sequence of FR1 of the VL includes an amino acid sequence set forth in SEQ ID NO:53,
the amino acid sequence of FR2 of the VL includes an amino acid sequence set forth in SEQ ID NO:60,
The amino acid sequence of FR3 of the VL includes an amino acid sequence set forth in SEQ ID NO:64, and
the amino acid sequence of FR4 of the VL includes the amino acid sequence set forth in SEQ ID NO:30;
(l) an antibody or an antibody fragment thereof in which:
the amino acid sequence of FR1 of the VH includes an amino acid sequence set forth in SEQ ID NO:33,
the amino acid sequence of FR2 of the VH includes an amino acid sequence set forth in SEQ ID NO:44,
the amino acid sequence of FR3 of the VH includes an amino acid sequence set forth in SEQ ID NO:47,
the amino acid sequence of FR4 of the VH includes an amino acid sequence set forth in SEQ ID NO:50,
the amino acid sequence of FR1 of the VL includes an amino acid sequence set forth in SEQ ID NO:54,
the amino acid sequence of FR2 of the VL includes an amino acid sequence set forth in SEQ ID NO:60,
the amino acid sequence of FR3 of the VL includes an amino acid sequence set forth in SEQ ID NO:65, and the amino acid sequence of FR4 of the VL includes the
amino acid sequence set forth in SEQ ID NO:30;
(m) an antibody or an antibody fragment thereof in which:
the amino acid sequence of FR1 of the VH includes an
amino acid sequence set forth in SEQ ID NO:34,
the amino acid sequence of FR2 of the VH includes an
amino acid sequence set forth in SEQ ID NO:44,
the amino acid sequence of FR3 of the VH includes an
amino acid sequence set forth in SEQ ID NO:46,
the amino acid sequence of FR4 of the VH includes an
amino acid sequence set forth in SEQ ID NO:51,
the amino acid sequence of FR1 of the VL includes an
amino acid sequence set forth in SEQ ID NO:54,
the amino acid sequence of FR2 of the VL includes an
amino acid sequence set forth in SEQ ID NO:61,
The amino acid sequence of FR3 of the VL includes an
amino acid sequence set forth in SEQ ID NO:64, and
the amino acid sequence of FR4 of the VL includes the
amino acid sequence set forth in SEQ ID NO:30;
(n) an antibody or an antibody fragment thereof in which:
the amino acid sequence of FR1 of the VH includes an
amino acid sequence set forth in SEQ ID NO:35,
the amino acid sequence of FR2 of the VH includes an
amino acid sequence set forth in SEQ ID NO:43,
the amino acid sequence of FR3 of the VH includes an
amino acid sequence set forth in SEQ ID NO:48,
the amino acid sequence of FR4 of the VH includes an
amino acid sequence set forth in SEQ ID NO:50,
the amino acid sequence of FR1 of the VL includes an
amino acid sequence set forth in SEQ ID NO:55,
the amino acid sequence of FR2 of the VL includes an
amino acid sequence set forth in SEQ ID NO:60,
the amino acid sequence of FR3 of the VL includes an
amino acid sequence set forth in SEQ ID NO:66, and
the amino acid sequence of FR4 of the VL includes the
amino acid sequence set forth in SEQ ID NO:30;
(o) an antibody or an antibody fragment thereof in which:
the amino acid sequence of FR1 of the VH includes an
amino acid sequence set forth in SEQ ID NO:36,
the amino acid sequence of FR2 of the VH includes an
amino acid sequence set forth in SEQ ID NO:44,
the amino acid sequence of FR3 of the VH includes an
amino acid sequence set forth in SEQ ID NO:47,
the amino acid sequence of FR4 of the VH includes an
amino acid sequence set forth in SEQ ID NO:50,
the amino acid sequence of FR1 of the VL includes an
amino acid sequence set forth in SEQ ID NO:56,
the amino acid sequence of FR2 of the VL includes an
amino acid sequence set forth in SEQ ID NO:60,
the amino acid sequence of FR3 of the VL includes an
amino acid sequence set forth in SEQ ID NO:65, and
the amino acid sequence of FR4 of the VL includes the
amino acid sequence set forth in SEQ ID NO:30;
(p) an antibody or an antibody fragment thereof in which:
the amino acid sequence of FR1 of the VH includes an
amino acid sequence set forth in SEQ ID NO:37,
the amino acid sequence of FR2 of the VH includes an
amino acid sequence set forth in SEQ ID NO:43,
the amino acid sequence of FR3 of the VH includes an
amino acid sequence set forth in SEQ ID NO:48,
the amino acid sequence of FR4 of the VH includes an
amino acid sequence set forth in SEQ ID NO:50,
the amino acid sequence of FR1 of the VL includes an
amino acid sequence set forth in SEQ ID NO:57,
the amino acid sequence of FR2 of the VL includes an
amino acid sequence set forth in SEQ ID NO:60,
the amino acid sequence of FR3 of the VL includes an
amino acid sequence set forth in SEQ ID NO:66, and
the amino acid sequence of FR4 of the VL includes the
amino acid sequence set forth in SEQ ID NO:30;
(q) an antibody or an antibody fragment thereof in which:
the amino acid sequence of FR1 of the VH includes an
amino acid sequence set forth in SEQ ID NO:38,
the amino acid sequence of FR2 of the VH includes an
amino acid sequence set forth in SEQ ID NO:44,
the amino acid sequence of FR3 of the VH includes an
amino acid sequence set forth in SEQ ID NO:46,
the amino acid sequence of FR4 of the VH includes an
amino acid sequence set forth in SEQ ID NO:50,
the amino acid sequence of FR1 of the VL includes an
amino acid sequence set forth in SEQ ID NO:57,
the amino acid sequence of FR2 of the VL includes an
amino acid sequence set forth in SEQ ID NO:60,
the amino acid sequence of FR3 of the VL includes an
amino acid sequence set forth in SEQ ID NO:65, and
the amino acid sequence of FR4 of the VL includes the
amino acid sequence set forth in SEQ ID NO:30;
(r) an antibody or an antibody fragment thereof in which:
the amino acid sequence of FR1 of the VH includes an
amino acid sequence set forth in SEQ ID NO:39,
the amino acid sequence of FR2 of the VH includes an
amino acid sequence set forth in SEQ ID NO:43,
the amino acid sequence of FR3 of the VH includes an
amino acid sequence set forth in SEQ ID NO:49,
the amino acid sequence of FR4 of the VH includes an
amino acid sequence set forth in SEQ ID NO:50,
the amino acid sequence of FR1 of the VL includes an
amino acid sequence set forth in SEQ ID NO:56,
the amino acid sequence of FR2 of the VL includes an
amino acid sequence set forth in SEQ ID NO:61,
the amino acid sequence of FR3 of the VL includes an
amino acid sequence set forth in SEQ ID NO:67, and
the amino acid sequence of FR4 of the VL includes the
amino acid sequence set forth in SEQ ID NO:30;
(s) an antibody or an antibody fragment thereof in which:
the amino acid sequence of FR1 of the VH includes the
amino acid sequence set forth in SEQ ID NO:32,
the amino acid sequence of FR2 of the VH includes an
amino acid sequence set forth in SEQ ID NO:44,
the amino acid sequence of FR3 of the VH includes an
amino acid sequence set forth in SEQ ID NO:47,
the amino acid sequence of FR4 of the VH includes an
amino acid sequence set forth in SEQ ID NO:50,
the amino acid sequence of FR1 of the VL includes an
amino acid sequence set forth in SEQ ID NO:55,
the amino acid sequence of FR2 of the VL includes an
amino acid sequence set forth in SEQ ID NO:60,
The amino acid sequence of FR3 of the VL includes an
amino acid sequence set forth in SEQ ID NO:64, and
the amino acid sequence of FR4 of the VL includes the
amino acid sequence set forth in SEQ ID NO:30;
(t) an antibody or an antibody fragment thereof in which:
the amino acid sequence of FR1 of the VH includes the
amino acid sequence set forth in SEQ ID NO:35,
the amino acid sequence of FR2 of the VH includes an
amino acid sequence set forth in SEQ ID NO:43,
the amino acid sequence of FR3 of the VH includes an
amino acid sequence set forth in SEQ ID NO:48,
the amino acid sequence of FR4 of the VH includes an
amino acid sequence set forth in SEQ ID NO:50,
the amino acid sequence of FR1 of the VL includes an
amino acid sequence set forth in SEQ ID NO:58, the amino acid sequence of FR2 of the VL includes an amino acid sequence set forth in SEQ ID NO:60,
the amino acid sequence of FR3 of the VL includes an amino acid sequence set forth in SEQ ID NO:65, and
the amino acid sequence of FR4 of the VL includes the amino acid sequence set forth in SEQ ID NO:30;
(u) an antibody or an antibody fragment thereof in which:
the amino acid sequence of FR1 of the VH includes an amino acid sequence set forth in SEQ ID NO:40,
the amino acid sequence of FR2 of the VH includes an amino acid sequence set forth in SEQ ID NO:44,
the amino acid sequence of FR3 of the VH includes an amino acid sequence set forth in SEQ ID NO:46,
the amino acid sequence of FR4 of the VH includes an amino acid sequence set forth in SEQ ID NO:50,
the amino acid sequence of FR1 of the VL includes an amino acid sequence set forth in SEQ ID NO:52,
the amino acid sequence of FR2 of the VL includes an amino acid sequence set forth in SEQ ID NO:61,
The amino acid sequence of FR3 of the VL includes an amino acid sequence set forth in SEQ ID NO:64, and
the amino acid sequence of FR4 of the VL includes the amino acid sequence set forth in SEQ ID NO:30;
(v) an antibody or an antibody fragment thereof in which:
the amino acid sequence of FR1 of the VH includes an amino acid sequence set forth in SEQ ID NO:41,
the amino acid sequence of FR2 of the VH includes an amino acid sequence set forth in SEQ ID NO:43,
the amino acid sequence of FR3 of the VH includes an amino acid sequence set forth in SEQ ID NO:49,
the amino acid sequence of FR4 of the VH includes an amino acid sequence set forth in SEQ ID NO:50,
the amino acid sequence of FR1 of the VL includes an amino acid sequence set forth in SEQ ID NO:58,
the amino acid sequence of FR2 of the VL includes an amino acid sequence set forth in SEQ ID NO:61,
the amino acid sequence of FR3 of the VL includes an amino acid sequence set forth in SEQ ID NO:68, and
the amino acid sequence of FR4 of the VL includes the amino acid sequence set forth in SEQ ID NO:30;
(w) an antibody or an antibody fragment thereof in which:
the amino acid sequence of FR1 of the VH includes the amino acid sequence set forth in SEQ ID NO:33,
the amino acid sequence of FR2 of the VH includes an amino acid sequence set forth in SEQ ID NO:44,
the amino acid sequence of FR3 of the VH includes an amino acid sequence set forth in SEQ ID NO:46,
the amino acid sequence of FR4 of the VH includes an amino acid sequence set forth in SEQ ID NO:50,
the amino acid sequence of FR1 of the VL includes an amino acid sequence set forth in SEQ ID NO:59,
the amino acid sequence of FR2 of the VL includes an amino acid sequence set forth in SEQ ID NO:61,
The amino acid sequence of FR3 of the VL includes an amino acid sequence set forth in SEQ ID NO:64, and
the amino acid sequence of FR4 of the VL includes the amino acid sequence set forth in SEQ ID NO:30;
(x) an antibody or an antibody fragment thereof in which:
the amino acid sequence of FR1 of the VH includes the amino acid sequence set forth in SEQ ID NO:33,
the amino acid sequence of FR2 of the VH includes an amino acid sequence set forth in SEQ ID NO:44,
the amino acid sequence of FR3 of the VH includes an amino acid sequence set forth in SEQ ID NO:47,
the amino acid sequence of FR4 of the VH includes an amino acid sequence set forth in SEQ ID NO:50,
the amino acid sequence of FR1 of the VL includes an amino acid sequence set forth in SEQ ID NO:58,
the amino acid sequence of FR2 of the VL includes an amino acid sequence set forth in SEQ ID NO:62,
The amino acid sequence of FR3 of the VL includes an amino acid sequence set forth in SEQ ID NO:64, and
the amino acid sequence of FR4 of the VL includes the amino acid sequence set forth in SEQ ID NO:30;
(y) an antibody or an antibody fragment thereof in which:
the amino acid sequence of FR1 of the VH includes the amino acid sequence set forth in SEQ ID NO:33,
the amino acid sequence of FR2 of VH includes an amino acid sequence set forth in SEQ ID NO:45,
the amino acid sequence of FR3 of the VH includes an amino acid sequence set forth in SEQ ID NO:47,
the amino acid sequence of FR4 of the VH includes an amino acid sequence set forth in SEQ ID NO:50,
the amino acid sequence of FR1 of the VL includes an amino acid sequence set forth in SEQ ID NO:54,
the amino acid sequence of FR2 of the VL includes an amino acid sequence set forth in SEQ ID NO:61,
The amino acid sequence of FR3 of the VL includes an amino acid sequence set forth in SEQ ID NO:64, and
the amino acid sequence of FR4 of the VL includes the amino acid sequence set forth in SEQ ID NO:30;
(z) an antibody or an antibody fragment thereof in which:
the amino acid sequence of FR1 of the VH includes the amino acid sequence set forth in SEQ ID NO:35,
the amino acid sequence of FR2 of the VH includes an amino acid sequence set forth in SEQ ID NO:43,
the amino acid sequence of FR3 of the VH includes an amino acid sequence set forth in SEQ ID NO:49,
the amino acid sequence of FR4 of the VH includes an amino acid sequence set forth in SEQ ID NO:50,
the amino acid sequence of FR1 of the VL includes an amino acid sequence set forth in SEQ ID NO:54,
the amino acid sequence of FR2 of the VL includes an amino acid sequence set forth in SEQ ID NO:60,
the amino acid sequence of FR3 of the VL includes an amino acid sequence set forth in SEQ ID NO:65, and
the amino acid sequence of FR4 of the VL includes the amino acid sequence set forth in SEQ ID NO:30;
(D) an antibody or an antibody fragment thereof in which:
the amino acid sequence of FR1 of the VH includes the amino acid sequence set forth in SEQ ID NO:31,
the amino acid sequence of FR2 of the VH includes an amino acid sequence set forth in SEQ ID NO:44,
the amino acid sequence of FR3 of the VH includes an amino acid sequence set forth in SEQ ID NO:46,
the amino acid sequence of FR4 of the VH includes an amino acid sequence set forth in SEQ ID NO:51,
the amino acid sequence of FR1 of the VL includes an amino acid sequence set forth in SEQ ID NO:54,
the amino acid sequence of FR2 of the VL includes an amino acid sequence set forth in SEQ ID NO:61,
The amino acid sequence of FR3 of the VL includes an amino acid sequence set forth in SEQ ID NO:64, and
the amino acid sequence of FR4 of the VL includes the amino acid sequence set forth in SEQ ID NO:30;
(E) an antibody or an antibody fragment thereof in which:
the amino acid sequence of FR1 of the VH includes an amino acid sequence set forth in SEQ ID NO:72,
the amino acid sequence of FR2 of the VH includes an amino acid sequence set forth in SEQ ID NO:44,
the amino acid sequence of FR3 of the VH includes an amino acid sequence set forth in SEQ ID NO:46, the amino acid sequence of FR4 of the VH includes an amino acid sequence set forth in SEQ ID NO:50,
the amino acid sequence of FR1 of the VL includes an amino acid sequence set forth in SEQ ID NO:58,
the amino acid sequence of FR2 of the VL includes an amino acid sequence set forth in SEQ ID NO:60,
the amino acid sequence of FR3 of the VL includes an amino acid sequence set forth in SEQ ID NO:65, and
the amino acid sequence of FR4 of the VL includes the amino acid sequence set forth in SEQ ID NO:30;
(F) an antibody or an antibody fragment thereof in which:
the amino acid sequence of FR1 of the VH includes the amino acid sequence set forth in SEQ ID NO:32,
the amino acid sequence of FR2 of the VH includes an amino acid sequence set forth in SEQ ID NO:44,
the amino acid sequence of FR3 of the VH includes an amino acid sequence set forth in SEQ ID NO:47,
the amino acid sequence of FR4 of the VH includes an amino acid sequence set forth in SEQ ID NO:50,
the amino acid sequence of FR1 of the VL includes an amino acid sequence set forth in SEQ ID NO:56,
the amino acid sequence of FR2 of the VL includes an amino acid sequence set forth in SEQ ID NO:61,
The amino acid sequence of FR3 of the VL includes an amino acid sequence set forth in SEQ ID NO:64, and
the amino acid sequence of FR4 of the VL includes the amino acid sequence set forth in SEQ ID NO:30;
(G) an antibody or an antibody fragment thereof in which:
the amino acid sequence of FR1 of the VH includes the amino acid sequence set forth in SEQ ID NO:33,
the amino acid sequence of FR2 of the VH includes an amino acid sequence set forth in SEQ ID NO:44,
the amino acid sequence of FR3 of the VH includes an amino acid sequence set forth in SEQ ID NO:49,
the amino acid sequence of FR4 of the VH includes an amino acid sequence set forth in SEQ ID NO:50,
the amino acid sequence of FR1 of the VL includes an amino acid sequence set forth in SEQ ID NO:58,
the amino acid sequence of FR2 of the VL includes an amino acid sequence set forth in SEQ ID NO:60,
the amino acid sequence of FR3 of the VL includes an amino acid sequence set forth in SEQ ID NO:63, and
the amino acid sequence of FR4 of the VL includes the amino acid sequence set forth in SEQ ID NO:30;
(H) an antibody or an antibody fragment thereof in which:
the amino acid sequence of FR1 of the VH includes the amino acid sequence set forth in SEQ ID NO:39,
the amino acid sequence of FR2 of the VH includes an amino acid sequence set forth in SEQ ID NO:43,
the amino acid sequence of FR3 of the VH includes an amino acid sequence set forth in SEQ ID NO:48,
the amino acid sequence of FR4 of the VH includes an amino acid sequence set forth in SEQ ID NO:50,
the amino acid sequence of FR1 of the VL includes an amino acid sequence set forth in SEQ ID NO:58,
the amino acid sequence of FR2 of the VL includes an amino acid sequence set forth in SEQ ID NO:60,
The amino acid sequence of FR3 of the VL includes an amino acid sequence set forth in SEQ ID NO:64, and
the amino acid sequence of FR4 of the VL includes the amino acid sequence set forth in SEQ ID NO:30;
(I) an antibody or an antibody fragment thereof in which:
the amino acid sequence of FR1 of the VH includes the amino acid sequence set forth in SEQ ID NO:31,
the amino acid sequence of FR2 of the VH includes an amino acid sequence set forth in SEQ ID NO:44, the amino acid sequence of FR3 of the VH includes an amino acid sequence set forth in SEQ ID NO:46,
the amino acid sequence of FR4 of the VH includes an amino acid sequence set forth in SEQ ID NO:51,
the amino acid sequence of FR1 of the VL includes an amino acid sequence set forth in SEQ ID NO:57,
the amino acid sequence of FR2 of the VL includes an amino acid sequence set forth in SEQ ID NO:60,
The amino acid sequence of FR3 of the VL includes an amino acid sequence set forth in SEQ ID NO:64, and
the amino acid sequence of FR4 of the VL includes the amino acid sequence set forth in SEQ ID NO:30;

(10) A nucleic acid according to a second aspect encodes the antibody or an antibody fragment thereof according to the first aspect.

(11) A vector according to a third aspect includes the nucleic acid according to the second aspect.

(12) With regard to the vector according to the above-described embodiment, the vector may be an expression vector derived from mammal.

(13) An antibody-producing cell according to a fourth aspect may be obtained by introducing the vector according to the second aspect into a host cell.

(14) With regard to the antibody-producing cell according to the above-described embodiment, the host cell may be a HEK293 cell or a CHO cell.

(15) A method for producing the antibody or the antibody fragment thereof according to a fifth aspect includes culturing the antibody-producing cell according to the fourth aspect to produce and accumulate the antibody or the antibody fragment thereof according to the first aspect, and collecting the antibody or the antibody fragment thereof from the culture.

(16) An immunological measuring method of 8-OHdG in a specimen according to a sixth aspect includes using the antibody or the antibody fragment thereof according to the first aspect.

(17) With regard to the measuring method according to the above-described embodiment, the specimen may be urine.

(18) A kit for measuring 8-OHdG in a specimen according to a seventh aspect includes the antibody or the antibody fragment thereof according to the first aspect.

(19) With regard to the kit according to the above-described embodiment, the specimen may be urine.

(20) A device for measuring 8-OHdG in a specimen according to an eighth aspect includes the antibody or the antibody fragment thereof according to the first aspect.

(21) With regard to the device according to the above-described embodiment, the specimen may be urine.

Advantageous Effects of Invention

According to the present invention, in order to more accurately analyze 8-OHdG in a specimen, particularly urine, an antibody and an antibody fragment thereof having high selectivity and specificity without being affected by an analog or urea at the concentration at which urea is included in urine, and a measurement method capable of measuring 8-OHdG in a specimen, particularly urine, with high sensitivity can be provided.

BEST MODE FOR CARRYING OUT THE INVENTION

Figure 1:
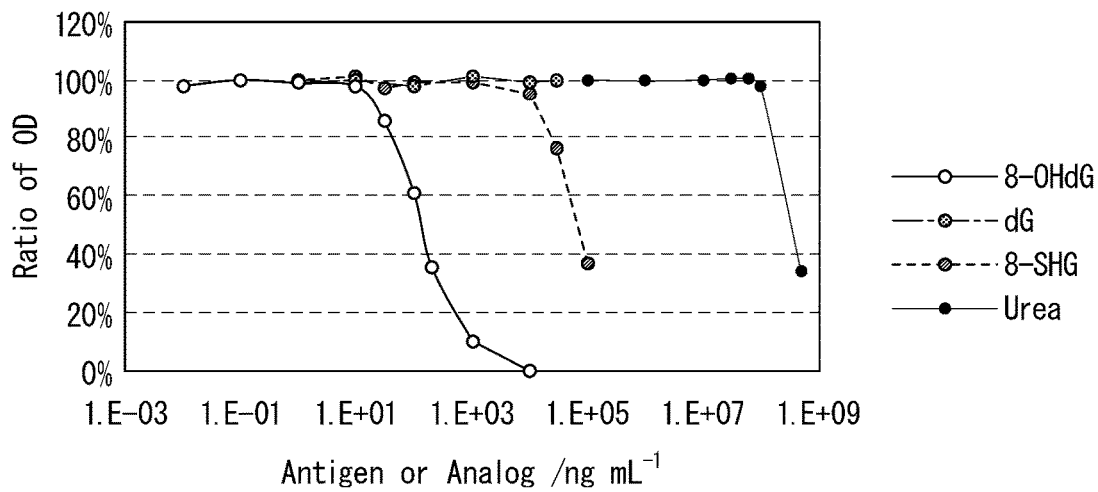
FIG. 1 is a diagram showing the results of measuring the reactivity of an anti-8-OHdG antibody (R4B-E5) of the present invention with 8-OHdG, 8-OHdG analogs, and urea by a competitive ELISA method. In the diagram, the ordinate axis shows the OD value when the OD value obtained at an 8-OHdG concentration in a specimen of 0.1 ng/mL is taken as 100%. The abscissa axis shows the concentration of 8-OHdG, 8-mercaptoguanosine (8-SHG), 2'-deoxyguanosine (dG), or urea in the specimen.

Hereinafter, embodiments of the present invention will be described in detail.

First Embodiment

[Antibody or Antibody Fragment Thereof]

According to the present invention, the term antibody is used synonymously with immunoglobulin (or Ig). In the present specification, unless stated otherwise herein, an antibody or immunoglobulin represents an intact (or whole) antibody molecule.

In nature, antibodies are glycoprotein molecules produced by B lymphocytes. In general, antibodies bind to antigens with a high degree of specificity and can be subclassified into five classes (or isotypes) indicated as IgG, IgM, IgA, IgD, and IgE, based on the physical and functional characteristics. These different types of antibodies share a common basic structural unit having a molecular weight of about 150,000 daltons (150 kDa) and each of the antibodies has two identical polypeptide heavy chains (H-chains) and two identical light chains (L-chains) which are covalently linked by interchain disulfide (S—S) bonds between cysteine residues. The intact antibody of the present invention also has this structure. Preferably, they are of the IgG type.

The antibody according to the present invention may be any antibody such as a monoclonal antibody or a polyclonal antibody; however, a monoclonal antibody is preferred. Specific examples of the antibody of the present invention include an antibody produced by a hybridoma and an antibody produced by a gene recombination technology. A monoclonal antibody is an antibody produced by a monoclonal antibody-producing cell, and the monoclonal antibody recognizes only one epitope and has uniform amino acid sequences constituting the antibody.

In the present invention, an antibody fragment means any portion of an antibody, and preferably an antigen-binding portion, and includes a variant of such a portion. Examples of the antigen-binding fragment according to the present invention include Fab, Fab', F(ab')$_2$, and minibody. Variants of such antibody fragments include dimers and trimers of those antibody fragments and fusion products between fragments, or chemical conjugates, all of which can be obtained using natural hinge sequences, synthetic hinge sequences, and peptide linkers. The antibody fragment of the present invention may be monovalent (for example, Fab fragment), divalent (for example, F(ab')$_2$ fragment), or polyvalent (for example, chemical conjugate including a trimer Fab fragment).

Here, complementarity-determining regions (CDR) are composed of heavy chain complementarity-determining regions (hereinafter, also referred to as H-CDRs) and light chain complementarity-determining regions (hereinafter, also referred to as L-CDRs). Each of the variable regions of the heavy and light chains consists of three CDRs and four framework regions (FRs) connected by the CDRs. The CDRs in each chain are held in the neighborhood by the FRs and, together with the CDRs in the other chain, contribute to the formation of an antigen-binding site of the antibody.

The amino acid sequence of a CDR in the antibody molecule can be determined based on a known method, for example, the Analyze immunoglobulin (Ig) sequences database of the NCBI (National Center for Biotechnology Information).

The antibody or the antibody fragment thereof of the present embodiment is an anti-8-OHdG antibody or an antibody fragment thereof which specifically reacts with 8-OHdG and substantially does not react with urea.

In the present specification, when it is said that the anti-8-OHdG antibody or the antibody fragment thereof of the present embodiment substantially does not react with urea, it is meant that there is no reactivity at all, or only very weak reactivity is exhibited, between the antibody or the antibody fragment thereof and urea in the concentration range of urea at which urea is normally present in the specimen. For example, the antibody or the antibody fragment thereof may not react with $1\times10^5$ to $6\times10^7$ ng/mL of urea in a specimen, or the concentration of urea that inhibits the immune response between the antibody or the antibody fragment thereof and 8-OHdG by 50% may be 100 mg/mL or more, 300 mg/mL or more, or 400 mg/mL or more. Since the urea concentration in the urine of a healthy person is 10 to 30 mg/mL, it is preferable that the anti-8-OHdG antibody or the antibody fragment thereof of the present embodiment not react with urea in urine even at a urea concentration in urine of preferably 30 mg/mL, more preferably 60 mg/mL, and even more preferably 80 mg/mL.

Furthermore, it is preferable that the anti-8-OHdG antibody or the antibody fragment thereof of the present embodiment substantially not react with substances other than 8-OHdG included in urine (hereinafter, also referred to as substances contained in urine, including urea), in addition to urea. Examples of the substances contained in urine include urea, uric acid, creatine, and creatinine.

It is preferable that the anti-8-OHdG antibody or the antibody fragment thereof of the present embodiment substantially not react with an analog of 8-OHdG. Examples of the analog of 8-OHdG include 8-hydroxyguanosine, 8-hydroxyguanine, 8-mercaptoguanosine, 8-bromoguanosine, guanosine, guanine, 2'-deoxyguanosine, 2'-deoxyadenosine, 2'-deoxyinosine, 2'-deoxycytidine, 2'-deoxythymidine, 2'-deoxyuridine, 7-methylguanosine, 6-O-methylguanine, 6-O-methyldeoxyguanosine, and 6-O-methylguanosine.

In the present specification, when it is said that the anti-8-OHdG antibody or the antibody fragment thereof of the present embodiment substantially does not react with an analog of 8-OHdG, it is meant that there is no reactivity at all, or only very weak reactivity is exhibited, between the antibody or the antibody fragment thereof with the analog of 8-OHdG in the concentration range of the analog of 8-OHdG at which the analog of 8-OHdG is usually present in the specimen, and for example, the antibody or the antibody fragment thereof may not react with the analog of 8-OHdG at a concentration of 100 ng/mL or less in the specimen. Examples of an antibody or antibody fragment thereof that substantially does not react with an analog of 8-OHdG include an antibody or an antibody fragment thereof such that the concentration of 8-mercaptoguanosine (also referred to as 8-SHG) that inhibits an immune response between the antibody or the antibody fragment and 8-OHdG by 50% is 100 or more times, 200 or more times, 300 or more times, 400 or more times, or 500 or more times, the concentration of 8-OHdG that inhibits the above-described immune response by 50%; and an antibody or an antibody fragment thereof such that the concentration of 2'-deoxyguanosine (also referred to as dG) that inhibits an immune response between the antibody or the antibody fragment thereof and 8-OHdG by 50% is 30 µg/mL or more.

The reactivity of the anti-8-OHdG or the antibody fragment thereof of the present embodiment with 8-OHdG, an analog thereof, or a substance contained in urine including urea can also be represented as an affinity between the antibody or the antibody fragment thereof and 8-OHdG, an analog thereof, or a substance contained in urine. Affinity can be expressed by the affinity constant $K_A$, and this is the ratio of the association rate constant ($k_a$) of an antibody or an antibody fragment and an antigen, to the dissociation rate constant ($k_d$). As the affinity is higher, the $K_A$ is higher. Alternatively, the affinity can also be expressed by the dissociation constant $K_D$, where $K_D=1/K_A$. The unit of $K_D$ is M, and as the affinity is higher, the $K_D$ is lower. According to the present invention, affinity is usually expressed by $K_D$. Since most of the affinity-measuring methods take into account the number of binding sites of the antibody or the antibody fragment, the $K_A$ and $K_D$ affinity values actually reflect the affinity for a monovalent antibody or antibody fragment, and avidity can be regarded to be related to a polyvalent antibody or antibody fragment.

Examples of the method that can be used to measure the affinity include surface plasmon resonance (SPR) using a Biacore method. Using this method, not only the affinity constant but also the binding rate can be measured. According to this method, $K_D=k_d/k_a$ (in the formula, $k_d$ is the dissociation rate constant; and $k_a$ is the association rate constant).

The anti-8-OHdG antibody or the antibody fragment thereof of the present embodiment can be produced by using a known method. Specifically, a rabbit is immunized with an antigen in which 8-OHdG is immobilized by succinylation on keyhole limpet hemocyanin, messenger RNA is extracted from total RNA isolated from either or both of the bone marrow cells and spleen cells of the immunized rabbit, and cDNA is synthesized by using the messenger RNA as a template. An antibody sequence region of the obtained cDNA is amplified and inserted into a phagemid vector, and the phagemid vector having the antibody sequence region inserted therein is used to transform a bacterium. Nucleic acids containing the antibody sequence region are extracted from the obtained transformant to create a gene library, each nucleic acid containing the antibody sequence region in the gene library is individually used to transform a bacterium while the bacterium is also infected with helper phages, and phages are extracted from the bacterial culture supernatant to create a phage library. Next, positive phage clones that react with 8-OHdG are screened by a biopanning method in which an immobilized antigen (8-OHdG) and a phage antibody in the phage library are subjected to an antigen-antibody reaction, nucleic acids are extracted from the positive phage clones, subsequently the genetic information is decoded, and the antibody sequence region is inserted into a vector for expressing IgG. The obtained vector is introduced into a host bacterium to transform the host bacterium, and then the vector is amplified and purified. The obtained vector is introduced into a host cell to obtain an antibody-producing cell. An 8-OHdG antibody or an antibody fragment thereof can be produced and accumulated in the antibody-producing cell, and the anti-8-OHdG antibody or the antibody fragment thereof of the present embodiment can be produced from the culture.

Regarding the anti-8-OHdG antibody or the antibody fragment thereof of the present embodiment, an antibody or an antibody fragment thereof in which the amino acid sequence of CDR2 includes the amino acid sequence set forth in SEQ ID NO:1; the amino acid sequence of CDR3 of the VH includes the amino acid sequence set forth in SEQ ID NO:2 or an amino acid sequence represented by the amino acid sequence in which the 8th isoleucine of SEQ ID NO:2 substituted with valine; the amino acid sequence of CDR1 of the VL includes the amino acid sequence set forth in SEQ ID NO:3; and the amino acid sequence of CDR3 of the VL includes the amino acid sequence set forth in SEQ ID NO:4 may be mentioned.

The amino acid sequences set forth in SEQ ID NO: 1 to SEQ ID NO:4 are shown in Table 1.

TABLE 1

| Sequence No. | Variable region | CDR | Amino acid sequence |
|---|---|---|---|
| 1 | VH | 2 | INEWG |
| 2 | VH | 3 | WGSRVFNI |
| 3 | VL | 1 | QSVY |
| 4 | VL | 3 | LGSYDAR |

Regarding such an anti-8-OHdG antibody or an antibody fragment thereof, for example, an anti-8-OHdG antibody or an antibody fragment thereof in which the amino acid sequence of CDR1 of the VH includes any one amino acid sequence selected from the group consisting of the amino acid sequence set forth in SEQ ID NO:11, an amino acid sequence in which the 4th leucine of SEQ ID NO:11 is substituted with proline, and an amino acid sequence in which the 5th serine of SEQ ID NO:11 is substituted with methionine; the amino acid sequence of CDR2 of the VH includes any one amino acid sequence selected from the group consisting of an amino acid sequence set forth in SEQ ID NO:6, an amino acid sequence in which the 6th asparagine of SEQ ID NO:6 is substituted with histidine or phenylalanine, an amino acid sequence in which the 7th isoleucine of SEQ ID NO:6 is substituted with valine, and an amino acid sequence in which the 6th asparagine of SEQ ID NO:6 is substituted with threonine and the 7th isoleucine is substituted with leucine; the amino acid sequence of CDR3 of the VH includes any one amino acid sequence selected from the group consisting of an amino acid sequence set forth in SEQ ID NO:7, an amino acid sequence in which the 4th valine of SEQ ID NO:7 is substituted with isoleucine, and an amino acid sequence in which the 12th isoleucine of SEQ ID NO:7 is substituted with valine; the amino acid sequence of CDR1 of the VL includes any one amino acid sequence selected from the group consisting of an amino acid sequence set forth in SEQ ID NO:8, and an amino acid sequence in which the 5th serine of SEQ ID NO:8 is substituted with asparagine or glycine; the amino acid sequence of CDR2 of the VL includes an amino acid sequence set forth in SEQ ID NO:9; and the amino acid sequence of CDR3 of the VL includes any one amino acid sequence selected from the group consisting of an amino acid sequence set forth in SEQ ID NO:10, an amino acid sequence in which the 8th serine of SEQ ID NO:10 is substituted with tyrosine, and an amino acid sequence in which the 8th serine of SEQ ID NO:10 is substituted with tyrosine and the 9th glycine is substituted with serine may be mentioned.

Specific examples of the anti-8-OHdG antibody or the antibody fragment thereof of the present embodiment include the anti-8-OHdG antibodies or antibody fragments thereof shown in the following (a) to (i) and (A) to (C).

(a) an anti-8-OHdG antibody or an antibody fragment thereof in which:
the amino acid sequence of CDR1 of the VH includes an amino acid sequence set forth in SEQ ID NO:5,
the amino acid sequence of CDR2 of the VH includes the amino acid sequence set forth in SEQ ID NO:6,
the amino acid sequence of CDR3 of the VH includes the amino acid sequence set forth in SEQ ID NO:7,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(b) an anti-8-OHdG antibody or an antibody fragment thereof in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes the amino acid sequence set forth in SEQ ID NO:7,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(c) an anti-8-OHdG antibody or an antibody fragment thereof in which:
the amino acid sequence of CDR1 of the VH includes the amino acid sequence set forth in SEQ ID NO:11,
the amino acid sequence of CDR2 of the VH includes an amino acid sequence set forth in SEQ ID NO:12,
the amino acid sequence of CDR3 of the VH includes the amino acid sequence set forth in SEQ ID NO:7,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(d) an anti-8-OHdG antibody or an antibody fragment thereof in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes an amino acid sequence set forth in SEQ ID NO:13,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:14;

(e) an anti-8-OHdG antibody or an antibody fragment thereof in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes an amino acid sequence set forth in SEQ ID NO:13,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:15;

(f) an anti-8-OHdG antibody or an antibody fragment thereof in which:
the amino acid sequence of CDR1 of the VH includes the amino acid sequence set forth in SEQ ID NO:11,
the amino acid sequence of CDR2 of the VH includes an amino acid sequence set forth in SEQ ID NO:16,
the amino acid sequence of CDR3 of the VH includes an amino acid sequence set forth in SEQ ID NO:13,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(g) an anti-8-OHdG antibody or an antibody fragment thereof in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes an amino acid sequence set forth in SEQ ID NO:13,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(h) an anti-8-OHdG antibody or an antibody fragment thereof in which:
the amino acid sequence of CDR1 of the VH includes an amino acid sequence set forth in SEQ ID NO:17,
the amino acid sequence of CDR2 of the VH includes the amino acid sequence set forth in SEQ ID NO:6,
the amino acid sequence of CDR3 of the VH includes the amino acid sequence set forth in SEQ ID NO:7,
the amino acid sequence of CDR1 of the VL includes an amino acid sequence set forth in SEQ ID NO:18,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(i) an anti-8-OHdG antibody or an antibody fragment thereof in which:
the amino acid sequence of CDR1 of the VH includes the amino acid sequence set forth in SEQ ID NO:11,
the amino acid sequence of CDR2 of the VH includes an amino acid sequence set forth in SEQ ID NO:19,
the amino acid sequence of CDR3 of the VH includes an amino acid sequence set forth in SEQ ID NO:13,
the amino acid sequence of CDR1 of the VL includes the amino acid sequence set forth in SEQ ID NO:8, the amino acid sequence of CDR2 of the VL includes the
amino acid sequence set forth in SEQ ID NO:9, and
the amino acid sequence of CDR3 of the VL includes the
amino acid sequence set forth in SEQ ID NO:10;
(A) an anti-8-OHdG antibody or an antibody fragment thereof in which:
the amino acid sequence of CDR1 of the VH includes the
amino acid sequence set forth in SEQ ID NO:11,
the amino acid sequence of CDR2 of the VH includes the
amino acid sequence set forth in SEQ ID NO:6,
the amino acid sequence of CDR3 of the VH includes the
amino acid sequence set forth in SEQ ID NO:7,
the amino acid sequence of CDR1 of the VL includes an
amino acid sequence set forth in SEQ ID NO:69,
the amino acid sequence of CDR2 of the VL includes the
amino acid sequence set forth in SEQ ID NO:9, and
the amino acid sequence of CDR3 of the VL includes the
amino acid sequence set forth in SEQ ID NO:10;
(B) an anti-8-OHdG antibody or an antibody fragment thereof in which:
the amino acid sequence of CDR1 of the VH includes the
amino acid sequence set forth in SEQ ID NO:11,
the amino acid sequence of CDR2 of the VH includes the
amino acid sequence set forth in SEQ ID NO:6,
the amino acid sequence of CDR3 of the VH includes an
amino acid sequence set forth in SEQ ID NO:70,
the amino acid sequence of CDR1 of the VL includes the
amino acid sequence set forth in SEQ ID NO:8,
the amino acid sequence of CDR2 of the VL includes the
amino acid sequence set forth in SEQ ID NO:9, and
the amino acid sequence of CDR3 of the VL includes the
amino acid sequence set forth in SEQ ID NO:10;
(C) an anti-8-OHdG antibody or an antibody fragment thereof in which:
the amino acid sequence of CDR1 of the VH includes the
amino acid sequence set forth in SEQ ID NO:11,
the amino acid sequence of CDR2 of the VH includes an
amino acid sequence set forth in SEQ ID NO:71,
the amino acid sequence of CDR3 of the VH includes the
amino acid sequence set forth in SEQ ID NO:7,
the amino acid sequence of CDR1 of the VL includes the
amino acid sequence set forth in SEQ ID NO:8,
the amino acid sequence of CDR2 of the VL includes the
amino acid sequence set forth in SEQ ID NO:9, and
the amino acid sequence of CDR3 of the VL includes the
amino acid sequence set forth in SEQ ID NO:10;

The amino acid sequences set forth in SEQ ID NO: 5 to SEQ ID NO:19 and SEQ ID NO:69 to SEQ ID NO:71 are shown in Table 2.

TABLE 2

| Sequence No. | Variable region | CDR | Amino acid sequence |
|---|---|---|---|
| 5 | VH | 1 | GFSPSTYG |
| 6 | VH | 2 | INEWGNI |
| 7 | VH | 3 | ASEVWGSRVFNI |
| 8 | VL | 1 | QSVYSKNY |
| 9 | VL | 2 | RAS |
| 10 | VL | 3 | LGSYDARSGDSNV |
| 11 | VH | 1 | GFSLSTYG |

TABLE 2-continued

| Sequence No. | Variable region | CDR | Amino acid sequence |
|---|---|---|---|
| 12 | VH | 2 | INEWGNV |
| 13 | VH | 3 | ASEIWGSRVFNI |
| 14 | VL | 3 | LGSYDARYGDSNV |
| 15 | VL | 3 | LGSYDARYSDSNV |
| 16 | VH | 2 | INEWGHI |
| 17 | VH | 1 | GFSLMTYG |
| 18 | VL | 1 | QSVYNKNY |
| 19 | VH | 2 | INEWGFI |
| 69 | VL | 1 | QSVYGKNY |
| 70 | VH | 3 | ASEVWGSRVFNV |
| 71 | VH | 2 | INEWGTL |

Regarding the anti-8-OHdG antibody or the antibody fragment thereof of the present embodiment, an anti-8-OHdG antibody or an antibody fragment thereof in which the amino acid sequence of FR1 of the VH includes the amino acid sequence set forth in SEQ ID NO:20; the amino acid sequence of FR2 of the VH includes the amino acid sequences set forth in SEQ ID NO:21 and SEQ ID NO:22; the amino acid sequence of FR3 of the VH includes the amino acid sequence set forth in SEQ ID NO:23; the amino acid sequence of FR4 of the VH includes the amino acid sequences set forth in SEQ ID NO:24 and SEQ ID NO:25; the amino acid sequence of FR1 of the VL includes the amino acid sequence set forth in SEQ ID NO:26; the amino acid sequence of FR2 of the VL includes the amino acid sequence set forth in SEQ ID NO:27; the amino acid sequence of FR3 of the VL includes the amino acid sequences set forth in SEQ ID NO:28 and SEQ ID NO:29; and the amino acid sequence of FR4 of the VL includes the amino acid sequence set forth in SEQ ID NO:30 is preferred.

The amino acid sequences set forth in SEQ ID NO: 20 to SEQ ID NO:30 are shown in Table 3.

TABLE 3

| Sequence No. | Variable region | FR | Sequence |
|---|---|---|---|
| 20 | VH | 1 | LTLTCTVS |
| 21 | VH | 2 | VSWVRQAPG |
| 22 | VH | 2 | GLDWIGN |
| 23 | VH | 3 | NTVTLKMTSLTAADTATYFC |
| 24 | VH | 4 | WGPGT |
| 25 | VH | 4 | VTVSS |
| 26 | VL | 1 | TQTPSSVSAAVGGTVTINCQAS |
| 27 | VL | 2 | LSWFQQKPGQPP |
| 28 | VL | 3 | NLASGVPSRFSGSGSG |
| 29 | VL | 3 | QCDDAATYYC |
| 30 | VL | 4 | FGGGTEVVVK |

Regarding the amino acid sequence of FR1 of the VH including the amino acid sequence set forth in SEQ ID NO:20, for example, an amino acid sequence set forth in any one of SEQ ID NO:31 to SEQ ID NO:41 and SEQ ID NO:72 may be mentioned.

Regarding the amino acid sequence of FR2 of the VH including the amino acid sequences set forth in SEQ ID NO:21 and SEQ ID NO:22, for example, an amino acid sequence set forth in any one of SEQ ID NO:42 to SEQ ID NO:45 may be mentioned.

Regarding the amino acid sequence of FR3 of the VH including the amino acid sequence set forth in SEQ ID NO:23, for example, an amino acid sequence set forth in any one of SEQ ID NO: 46 to SEQ ID NO:49 may be mentioned.

Regarding the amino acid sequence of FR4 of the VH including the amino acid sequences set forth in SEQ ID NO:24 and SEQ ID NO:25, for example, an amino acid sequence set forth in SEQ ID NO:50 or SEQ ID NO:51 may be mentioned.

Regarding the amino acid sequence of FR1 of the VL including the amino acid sequence set forth in SEQ ID NO:26, for example, an amino acid sequence set forth in any one of SEQ ID NO: 52 to SEQ ID NO:59 may be mentioned.

Regarding the amino acid sequence of FR2 of the VL including the amino acid sequence set forth in SEQ ID NO:27, for example, an amino acid sequence set forth in any one of SEQ ID NO:60 to SEQ ID NO:62 may be mentioned.

Regarding the amino acid sequence of FR3 of the VL including the amino acid sequences set forth in SEQ ID NO:28 and SEQ ID NO:29, for example, an amino acid sequence set forth in any one of SEQ ID NO:63 to SEQ ID NO:68 may be mentioned.

Specific examples of the FR of the anti-8-OHdG antibody of the present invention or an antibody fragment thereof include FRs represented by the following (j) to (z) and (D) to (I).

(j) an antibody or an antibody fragment thereof in which:
the amino acid sequence of FR1 of the VH includes an amino acid sequence set forth in SEQ ID NO:31,
the amino acid sequence of FR2 of the VH includes an amino acid sequence set forth in SEQ ID NO:44,
the amino acid sequence of FR3 of the VH includes an amino acid sequence set forth in SEQ ID NO:46,
the amino acid sequence of FR4 of the VH includes an amino acid sequence set forth in SEQ ID NO:50,
the amino acid sequence of FR1 of the VL includes an amino acid sequence set forth in SEQ ID NO:52,
the amino acid sequence of FR2 of the VL includes an amino acid sequence set forth in SEQ ID NO:60,
the amino acid sequence of FR3 of the VL includes an amino acid sequence set forth in SEQ ID NO:63, and
the amino acid sequence of FR4 of the VL includes the amino acid sequence set forth in SEQ ID NO:30;

(k) an antibody or an antibody fragment thereof in which:
the amino acid sequence of FR1 of the VH includes an amino acid sequence set forth in SEQ ID NO:32,
the amino acid sequence of FR2 of the VH includes an amino acid sequence set forth in SEQ ID NO:44,
the amino acid sequence of FR3 of the VH includes an amino acid sequence set forth in SEQ ID NO:47,
the amino acid sequence of FR4 of the VH includes an amino acid sequence set forth in SEQ ID NO:50,
the amino acid sequence of FR1 of the VL includes an amino acid sequence set forth in SEQ ID NO:53,
the amino acid sequence of FR2 of the VL includes an amino acid sequence set forth in SEQ ID NO:60,
The amino acid sequence of FR3 of the VL includes an amino acid sequence set forth in SEQ ID NO:64, and
the amino acid sequence of FR4 of the VL includes the amino acid sequence set forth in SEQ ID NO:30;

(l) an antibody or an antibody fragment thereof in which:
the amino acid sequence of FR1 of the VH includes an amino acid sequence set forth in SEQ ID NO:33,
the amino acid sequence of FR2 of the VH includes an amino acid sequence set forth in SEQ ID NO:44,
the amino acid sequence of FR3 of the VH includes an amino acid sequence set forth in SEQ ID NO:47,
the amino acid sequence of FR4 of the VH includes an amino acid sequence set forth in SEQ ID NO:50,
the amino acid sequence of FR1 of the VL includes an amino acid sequence set forth in SEQ ID NO:54,
the amino acid sequence of FR2 of the VL includes an amino acid sequence set forth in SEQ ID NO:60,
the amino acid sequence of FR3 of the VL includes an amino acid sequence set forth in SEQ ID NO:65, and
the amino acid sequence of FR4 of the VL includes the amino acid sequence set forth in SEQ ID NO:30;

(m) an antibody or an antibody fragment thereof in which:
the amino acid sequence of FR1 of the VH includes an amino acid sequence set forth in SEQ ID NO:34,
the amino acid sequence of FR2 of the VH includes an amino acid sequence set forth in SEQ ID NO:44,
the amino acid sequence of FR3 of the VH includes an amino acid sequence set forth in SEQ ID NO:46,
the amino acid sequence of FR4 of the VH includes an amino acid sequence set forth in SEQ ID NO:51,
the amino acid sequence of FR1 of the VL includes an amino acid sequence set forth in SEQ ID NO:54,
the amino acid sequence of FR2 of the VL includes an amino acid sequence set forth in SEQ ID NO:61,
The amino acid sequence of FR3 of the VL includes an amino acid sequence set forth in SEQ ID NO:64, and
the amino acid sequence of FR4 of the VL includes the amino acid sequence set forth in SEQ ID NO:30;

(n) an antibody or an antibody fragment thereof in which:
the amino acid sequence of FR1 of the VH includes an amino acid sequence set forth in SEQ ID NO:35,
the amino acid sequence of FR2 of the VH includes an amino acid sequence set forth in SEQ ID NO:43,
the amino acid sequence of FR3 of the VH includes an amino acid sequence set forth in SEQ ID NO:48,
the amino acid sequence of FR4 of the VH includes an amino acid sequence set forth in SEQ ID NO:50,
the amino acid sequence of FR1 of the VL includes an amino acid sequence set forth in SEQ ID NO:55,
the amino acid sequence of FR2 of the VL includes an amino acid sequence set forth in SEQ ID NO:60,
the amino acid sequence of FR3 of the VL includes an amino acid sequence set forth in SEQ ID NO:66, and
the amino acid sequence of FR4 of the VL includes the amino acid sequence set forth in SEQ ID NO:30;

(o) an antibody or an antibody fragment thereof in which:
the amino acid sequence of FR1 of the VH includes an amino acid sequence set forth in SEQ ID NO:36,
the amino acid sequence of FR2 of the VH includes an amino acid sequence set forth in SEQ ID NO:44,
the amino acid sequence of FR3 of the VH includes an amino acid sequence set forth in SEQ ID NO:47,
the amino acid sequence of FR4 of the VH includes an amino acid sequence set forth in SEQ ID NO:50,
the amino acid sequence of FR1 of the VL includes an amino acid sequence set forth in SEQ ID NO:56, the amino acid sequence of FR2 of the VL includes an amino acid sequence set forth in SEQ ID NO:60,
the amino acid sequence of FR3 of the VL includes an amino acid sequence set forth in SEQ ID NO:65, and
the amino acid sequence of FR4 of the VL includes the amino acid sequence set forth in SEQ ID NO:30;
(p) an antibody or an antibody fragment thereof in which:
the amino acid sequence of FR1 of the VH includes an amino acid sequence set forth in SEQ ID NO:37,
the amino acid sequence of FR2 of the VH includes an amino acid sequence set forth in SEQ ID NO:43,
the amino acid sequence of FR3 of the VH includes an amino acid sequence set forth in SEQ ID NO:48,
the amino acid sequence of FR4 of the VH includes an amino acid sequence set forth in SEQ ID NO:50,
the amino acid sequence of FR1 of the VL includes an amino acid sequence set forth in SEQ ID NO:57,
the amino acid sequence of FR2 of the VL includes an amino acid sequence set forth in SEQ ID NO:60,
the amino acid sequence of FR3 of the VL includes an amino acid sequence set forth in SEQ ID NO:66, and
the amino acid sequence of FR4 of the VL includes the amino acid sequence set forth in SEQ ID NO:30;
(q) an antibody or an antibody fragment thereof in which:
the amino acid sequence of FR1 of the VH includes an amino acid sequence set forth in SEQ ID NO:38,
the amino acid sequence of FR2 of the VH includes an amino acid sequence set forth in SEQ ID NO:44,
the amino acid sequence of FR3 of the VH includes an amino acid sequence set forth in SEQ ID NO:46,
the amino acid sequence of FR4 of the VH includes an amino acid sequence set forth in SEQ ID NO:50,
the amino acid sequence of FR1 of the VL includes an amino acid sequence set forth in SEQ ID NO:57,
the amino acid sequence of FR2 of the VL includes an amino acid sequence set forth in SEQ ID NO:60,
the amino acid sequence of FR3 of the VL includes an amino acid sequence set forth in SEQ ID NO:65, and
the amino acid sequence of FR4 of the VL includes the amino acid sequence set forth in SEQ ID NO:30;
(r) an antibody or an antibody fragment thereof in which:
the amino acid sequence of FR1 of the VH includes an amino acid sequence set forth in SEQ ID NO:39,
the amino acid sequence of FR2 of the VH includes an amino acid sequence set forth in SEQ ID NO:43,
the amino acid sequence of FR3 of the VH includes an amino acid sequence set forth in SEQ ID NO:49,
the amino acid sequence of FR4 of the VH includes an amino acid sequence set forth in SEQ ID NO:50,
the amino acid sequence of FR1 of the VL includes an amino acid sequence set forth in SEQ ID NO:56,
the amino acid sequence of FR2 of the VL includes an amino acid sequence set forth in SEQ ID NO:61,
the amino acid sequence of FR3 of the VL includes an amino acid sequence set forth in SEQ ID NO:67, and
the amino acid sequence of FR4 of the VL includes the amino acid sequence set forth in SEQ ID NO:30;
(s) an antibody or an antibody fragment thereof in which:
the amino acid sequence of FR1 of the VH includes the amino acid sequence set forth in SEQ ID NO:32,
the amino acid sequence of FR2 of the VH includes an amino acid sequence set forth in SEQ ID NO:44,
the amino acid sequence of FR3 of the VH includes an amino acid sequence set forth in SEQ ID NO:47,
the amino acid sequence of FR4 of the VH includes an amino acid sequence set forth in SEQ ID NO:50,
the amino acid sequence of FR1 of the VL includes an amino acid sequence set forth in SEQ ID NO:55,
the amino acid sequence of FR2 of the VL includes an amino acid sequence set forth in SEQ ID NO:60,
The amino acid sequence of FR3 of the VL includes an amino acid sequence set forth in SEQ ID NO:64, and
the amino acid sequence of FR4 of the VL includes the amino acid sequence set forth in SEQ ID NO:30;
(t) an antibody or an antibody fragment thereof in which:
the amino acid sequence of FR1 of the VH includes the amino acid sequence set forth in SEQ ID NO:35,
the amino acid sequence of FR2 of the VH includes an amino acid sequence set forth in SEQ ID NO:43,
the amino acid sequence of FR3 of the VH includes an amino acid sequence set forth in SEQ ID NO:48,
the amino acid sequence of FR4 of the VH includes an amino acid sequence set forth in SEQ ID NO:50,
the amino acid sequence of FR1 of the VL includes an amino acid sequence set forth in SEQ ID NO:58,
the amino acid sequence of FR2 of the VL includes an amino acid sequence set forth in SEQ ID NO:60,
the amino acid sequence of FR3 of the VL includes an amino acid sequence set forth in SEQ ID NO:65, and
the amino acid sequence of FR4 of the VL includes the amino acid sequence set forth in SEQ ID NO:30;
(u) an antibody or an antibody fragment thereof in which:
the amino acid sequence of FR1 of the VH includes an amino acid sequence set forth in SEQ ID NO:40,
the amino acid sequence of FR2 of the VH includes an amino acid sequence set forth in SEQ ID NO:44,
the amino acid sequence of FR3 of the VH includes an amino acid sequence set forth in SEQ ID NO:46,
the amino acid sequence of FR4 of the VH includes an amino acid sequence set forth in SEQ ID NO:50,
the amino acid sequence of FR1 of the VL includes an amino acid sequence set forth in SEQ ID NO:52,
the amino acid sequence of FR2 of the VL includes an amino acid sequence set forth in SEQ ID NO:61,
The amino acid sequence of FR3 of the VL includes an amino acid sequence set forth in SEQ ID NO:64, and
the amino acid sequence of FR4 of the VL includes the amino acid sequence set forth in SEQ ID NO:30;
(v) an antibody or an antibody fragment thereof in which:
the amino acid sequence of FR1 of the VH includes an amino acid sequence set forth in SEQ ID NO:41,
the amino acid sequence of FR2 of the VH includes an amino acid sequence set forth in SEQ ID NO:43,
the amino acid sequence of FR3 of the VH includes an amino acid sequence set forth in SEQ ID NO:49,
the amino acid sequence of FR4 of the VH includes an amino acid sequence set forth in SEQ ID NO:50,
the amino acid sequence of FR1 of the VL includes an amino acid sequence set forth in SEQ ID NO:58,
the amino acid sequence of FR2 of the VL includes an amino acid sequence set forth in SEQ ID NO:61,
the amino acid sequence of FR3 of the VL includes an amino acid sequence set forth in SEQ ID NO:68, and
the amino acid sequence of FR4 of the VL includes the amino acid sequence set forth in SEQ ID NO:30;
(w) an antibody or an antibody fragment thereof in which:
the amino acid sequence of FR1 of the VH includes the amino acid sequence set forth in SEQ ID NO:33,
the amino acid sequence of FR2 of the VH includes an amino acid sequence set forth in SEQ ID NO:44,
the amino acid sequence of FR3 of the VH includes an amino acid sequence set forth in SEQ ID NO:46, the amino acid sequence of FR4 of the VH includes an amino acid sequence set forth in SEQ ID NO:50,
the amino acid sequence of FR1 of the VL includes an amino acid sequence set forth in SEQ ID NO:59,
the amino acid sequence of FR2 of the VL includes an amino acid sequence set forth in SEQ ID NO:61,
The amino acid sequence of FR3 of the VL includes an amino acid sequence set forth in SEQ ID NO:64, and
the amino acid sequence of FR4 of the VL includes the amino acid sequence set forth in SEQ ID NO:30;
(x) an antibody or an antibody fragment thereof in which:
the amino acid sequence of FR1 of the VH includes the amino acid sequence set forth in SEQ ID NO:33,
the amino acid sequence of FR2 of the VH includes an amino acid sequence set forth in SEQ ID NO:44,
the amino acid sequence of FR3 of the VH includes an amino acid sequence set forth in SEQ ID NO:47,
the amino acid sequence of FR4 of the VH includes an amino acid sequence set forth in SEQ ID NO:50,
the amino acid sequence of FR1 of the VL includes an amino acid sequence set forth in SEQ ID NO:58,
the amino acid sequence of FR2 of the VL includes an amino acid sequence set forth in SEQ ID NO:62,
The amino acid sequence of FR3 of the VL includes an amino acid sequence set forth in SEQ ID NO:64, and
the amino acid sequence of FR4 of the VL includes the amino acid sequence set forth in SEQ ID NO:30;
(y) an antibody or an antibody fragment thereof in which:
the amino acid sequence of FR1 of the VH includes the amino acid sequence set forth in SEQ ID NO:33,
the amino acid sequence of FR2 of VH includes an amino acid sequence set forth in SEQ ID NO:45,
the amino acid sequence of FR3 of the VH includes an amino acid sequence set forth in SEQ ID NO:47,
the amino acid sequence of FR4 of the VH includes an amino acid sequence set forth in SEQ ID NO:50,
the amino acid sequence of FR1 of the VL includes an amino acid sequence set forth in SEQ ID NO:54,
the amino acid sequence of FR2 of the VL includes an amino acid sequence set forth in SEQ ID NO:61,
The amino acid sequence of FR3 of the VL includes an amino acid sequence set forth in SEQ ID NO:64, and
the amino acid sequence of FR4 of the VL includes the amino acid sequence set forth in SEQ ID NO:30;
(z) an antibody or an antibody fragment thereof in which:
the amino acid sequence of FR1 of the VH includes the amino acid sequence set forth in SEQ ID NO:35,
the amino acid sequence of FR2 of the VH includes an amino acid sequence set forth in SEQ ID NO:43,
the amino acid sequence of FR3 of the VH includes an amino acid sequence set forth in SEQ ID NO:49,
the amino acid sequence of FR4 of the VH includes an amino acid sequence set forth in SEQ ID NO:50,
the amino acid sequence of FR1 of the VL includes an amino acid sequence set forth in SEQ ID NO:54,
the amino acid sequence of FR2 of the VL includes an amino acid sequence set forth in SEQ ID NO:60,
the amino acid sequence of FR3 of the VL includes an amino acid sequence set forth in SEQ ID NO:65, and
the amino acid sequence of FR4 of the VL includes the amino acid sequence set forth in SEQ ID NO:30;
(D) an antibody or an antibody fragment thereof in which:
the amino acid sequence of FR1 of the VH includes the amino acid sequence set forth in SEQ ID NO:31,
the amino acid sequence of FR2 of the VH includes an amino acid sequence set forth in SEQ ID NO:44,
the amino acid sequence of FR3 of the VH includes an amino acid sequence set forth in SEQ ID NO:46,
the amino acid sequence of FR4 of the VH includes an amino acid sequence set forth in SEQ ID NO:51,
the amino acid sequence of FR1 of the VL includes an amino acid sequence set forth in SEQ ID NO:54,
the amino acid sequence of FR2 of the VL includes an amino acid sequence set forth in SEQ ID NO:61,
The amino acid sequence of FR3 of the VL includes an amino acid sequence set forth in SEQ ID NO:64, and
the amino acid sequence of FR4 of the VL includes the amino acid sequence set forth in SEQ ID NO:30;
(E) an antibody or an antibody fragment thereof in which:
the amino acid sequence of FR1 of the VH includes an amino acid sequence set forth in SEQ ID NO:72,
the amino acid sequence of FR2 of the VH includes an amino acid sequence set forth in SEQ ID NO:44,
the amino acid sequence of FR3 of the VH includes an amino acid sequence set forth in SEQ ID NO:46,
the amino acid sequence of FR4 of the VH includes an amino acid sequence set forth in SEQ ID NO:50,
the amino acid sequence of FR1 of the VL includes an amino acid sequence set forth in SEQ ID NO:58,
the amino acid sequence of FR2 of the VL includes an amino acid sequence set forth in SEQ ID NO:60,
the amino acid sequence of FR3 of the VL includes an amino acid sequence set forth in SEQ ID NO:65, and
the amino acid sequence of FR4 of the VL includes the amino acid sequence set forth in SEQ ID NO:30;
(F) an antibody or an antibody fragment thereof in which:
the amino acid sequence of FR1 of the VH includes the amino acid sequence set forth in SEQ ID NO:32,
the amino acid sequence of FR2 of the VH includes an amino acid sequence set forth in SEQ ID NO:44,
the amino acid sequence of FR3 of the VH includes an amino acid sequence set forth in SEQ ID NO:47,
the amino acid sequence of FR4 of the VH includes an amino acid sequence set forth in SEQ ID NO:50,
the amino acid sequence of FR1 of the VL includes an amino acid sequence set forth in SEQ ID NO:56,
the amino acid sequence of FR2 of the VL includes an amino acid sequence set forth in SEQ ID NO:61,
The amino acid sequence of FR3 of the VL includes an amino acid sequence set forth in SEQ ID NO:64, and
the amino acid sequence of FR4 of the VL includes the amino acid sequence set forth in SEQ ID NO:30;
(G) an antibody or an antibody fragment thereof in which:
the amino acid sequence of FR1 of the VH includes the amino acid sequence set forth in SEQ ID NO:33,
the amino acid sequence of FR2 of the VH includes an amino acid sequence set forth in SEQ ID NO:44,
the amino acid sequence of FR3 of the VH includes an amino acid sequence set forth in SEQ ID NO:49,
the amino acid sequence of FR4 of the VH includes an amino acid sequence set forth in SEQ ID NO:50,
the amino acid sequence of FR1 of the VL includes an amino acid sequence set forth in SEQ ID NO:58,
the amino acid sequence of FR2 of the VL includes an amino acid sequence set forth in SEQ ID NO:60,
the amino acid sequence of FR3 of the VL includes an amino acid sequence set forth in SEQ ID NO:63, and
the amino acid sequence of FR4 of the VL includes the amino acid sequence set forth in SEQ ID NO:30;
(H) an antibody or an antibody fragment thereof in which:
the amino acid sequence of FR1 of the VH includes the amino acid sequence set forth in SEQ ID NO:39, the amino acid sequence of FR2 of the VH includes an amino acid sequence set forth in SEQ ID NO:43,
the amino acid sequence of FR3 of the VH includes an amino acid sequence set forth in SEQ ID NO:48,
the amino acid sequence of FR4 of the VH includes an amino acid sequence set forth in SEQ ID NO:50,
the amino acid sequence of FR1 of the VL includes an amino acid sequence set forth in SEQ ID NO:58,
the amino acid sequence of FR2 of the VL includes an amino acid sequence set forth in SEQ ID NO:60,
The amino acid sequence of FR3 of the VL includes an amino acid sequence set forth in SEQ ID NO:64, and
the amino acid sequence of FR4 of the VL includes the amino acid sequence set forth in SEQ ID NO:30;
(I) an antibody or an antibody fragment thereof in which:
the amino acid sequence of FR1 of the VH includes the amino acid sequence set forth in SEQ ID NO:31,
the amino acid sequence of FR2 of the VH includes an amino acid sequence set forth in SEQ ID NO:44,
the amino acid sequence of FR3 of the VH includes an amino acid sequence set forth in SEQ ID NO:46,
the amino acid sequence of FR4 of the VH includes an amino acid sequence set forth in SEQ ID NO:51,
the amino acid sequence of FR1 of the VL includes an amino acid sequence set forth in SEQ ID NO:57,
the amino acid sequence of FR2 of the VL includes an amino acid sequence set forth in SEQ ID NO:60,
The amino acid sequence of FR3 of the VL includes an amino acid sequence set forth in SEQ ID NO:64, and
the amino acid sequence of FR4 of the VL includes the amino acid sequence set forth in SEQ ID NO:30;

The amino acid sequences set forth in SEQ ID NO:31 to SEQ ID NO:68 and SEQ ID NO:72 are shown in Table 4.

TABLE 4

| Sequence No. | Variable region | FR | Sequence |
|---|---|---|---|
| 31 | VH | 1 | QSVKESGGGLFKPTDTLTLTCTVS |
| 32 |  | 2 | QSVEESGGGLFKPTDTLTLTCTVS |
| 33 |  |  | QTVKESGGGLFKPTDTLTLTCTVS |
| 34 |  |  | QSVKESGGGLFKPTDTLTLTCTVS |
| 35 |  |  | QSVKESGGGLFKPADTLTLTCTVS |
| 36 |  |  | QSLEESGGGLFKPTDTLTLTCTVS |
| 37 |  |  | QEQQKESEGGLFKPADTLTLTCTVS |
| 38 |  |  | QSVKESRGGLFKPTDTLTLTCTVS |
| 39 |  |  | QTVKESGGGLFKPADTLTLTCTVS |
| 40 |  |  | QSVKESGGGLVKPGGSLTLTCTVS |
| 41 |  |  | QSLGESRGSLFKPADTLTLTCTVS |
| 72 |  |  | QEQLKESGGGLFKPTDTLTLTCTVS |
| 42 |  |  | VSWVRQAPGFGLDWIGN |
| 43 |  |  | VSWVRQAPGNGLDWIGN |
| 44 |  |  | VSWVRQAPGIGLDWIGN |
| 45 |  |  | VSWVRQAPGVGLDWIGN |
| 46 |  | 3 | FYASWAKSRSTITRN-TNENTVTLKMTSLTAADTATYFC |
| 47 |  |  | YYASWAKSRSTITRN-TNENTVTLKMTSLTAADTATYFC |
| 48 |  |  | FYAR-WAKSRSTITRHTNLNTVTLKMTSLTAADTATYFC |
| 49 |  |  | YYASWAKSRSTITRN-TNLNTVTLKMTSLTAADTATYFC |
| 50 |  | 4 | WGPGTLVTVSS |
| 51 |  |  | WGPGTPVTVSS |
| 52 | VL | 1 | AIKMTQTPSSVSAAVGGTVTINCQAS |
| 53 |  |  | AQVMTQTPSSVSAAVGGTVTINCQSS |
| 54 |  |  | AQVLTQTPSSVSAAVGGTVTINCQAS |
| 55 |  |  | AQGLTQTPSSVSAAVGGTVTINCQAS |
| 56 |  |  | ALVLTQTPSSVSAAVGGTVTINCQAS |
| 57 |  |  | AQGMTQTPSSVSAAVGGTVTINCQAS |
| 58 |  |  | ALVMTQTPSSVSAAVGGTVTINCQAS |
| 59 |  |  | AIQMTQTPSSVSAAVGGTVTINCQAS |
| 60 |  | 2 | LSWFQQKPGQPPKQLIY |
| 61 |  |  | LSWFQQKPGQPPRQLIY |
| 62 |  |  | LSWYQQKPGQPPKQLIY |
| 63 |  | 3 | NLASGVPSRFSGSGSGTQFTLTISSVQCDDAATYYC |
| 64 |  |  | NLASGVPSRFSGSGSGTEFTLTISSVQCDDAATYYC |
| 65 |  |  | NLASGVPSRFSGSGSGTEFTLTISDVQCDDAATYYC |
| 66 |  |  | NLASGVPSRFSGSGSGTEFTLTITSVQCDDAATYYC |
| 67 |  |  | NLASGVPSRFSGSGS-GAEFTLTISSVQCDDAATYYC |
| 68 |  |  | NLASGVPSRFSGSGSGTEFTLTISSAQCDDAATYYC |

The anti-8-OHdG antibody or the antibody fragment thereof of the present embodiment can also be produced by using a known gene recombination technology. Specifically, from a positive phage clone that reacts with the 8-OHdG, nucleic acids encoding the anti-8-OHdG antibody or the antibody fragment thereof of the present embodiment, VH, VL, CDR of VH, CDR of VL, FR of VH, FR of VL, and the like of the antibody or the antibody fragment thereof are inserted into a vector for expressing IgG. The obtained vector is introduced into a host bacterium and transformed to amplify and purify the vector. The obtained vector is introduced into a host cell to obtain an antibody-producing cell. An 8-OHdG antibody or an antibody fragment thereof can be produced and accumulated in the antibody-producing cell, and the anti-8-OHdG antibody or the antibody fragment thereof of the present embodiment can be produced from the culture.

Second Embodiment

[Nucleic Acid]

A nucleic acid of a second embodiment of the present invention is a nucleic acid encoding the anti-8-OHdG antibody or the antibody fragment thereof of the first embodiment. The nucleic acid of the present embodiment can be produced using a known gene recombination technology. Specifically, the nucleic acid is obtained by extracting nucleic acids encoding the anti-8-OHdG antibody or the antibody fragment thereof according to the first embodiment, VH, VL, CDR of VH, CDR of VL, FR of VH, FR of VL, and the like of the antibody or the antibody fragment thereof, from a positive phage clone that reacts with 8-OHdG. The obtained nucleic acid is inserted into a vector for expressing IgG to produce a vector, the vector is introduced into a host bacterium to transform the host bacterium, and the vector is amplified and purified. The vector is introduced into a host cell, and thereby an antibody-producing cell is obtained. An 8-OHdG antibody or an antibody fragment thereof can be produced and accumulated in the antibody-producing cell, and the anti-8-OHdG antibody or the antibody fragment thereof of the present embodiment can be produced from the culture.

Third Embodiment

[Vector]

A vector of a third embodiment of the present invention contains a nucleic acid encoding the anti-8-OHdG antibody of the second embodiment or an antibody fragment thereof. The vector of the present embodiment can be produced by using a known gene recombination technology. Specifically, the vector can be produced by extracting nucleic acid from a positive phage clone that reacts with the 8-OHdG, decoding the genetic information, and inserting an antibody sequence region into a vector for expressing IgG. The vector for expressing IgG into which a nucleic acid encoding the anti-8-OHdG antibody or antibody fragment thereof can be introduced is not particularly limited as long as the nucleic acid can be expressed, and any known vector, for example, any known expression vector derived from mammal can be used.

Fourth Embodiment

[Antibody-Producing Cell]

An antibody-producing cell of a fourth embodiment of the present invention is a host cell having the vector of the third embodiment introduced therein. The antibody-producing cell of the present embodiment can be produced using a known gene recombination technology. Specifically, nucleic acid is extracted from a positive phage clone that reacts with the 8-OHdG, subsequently genetic information is decoded, and an antibody sequence region is inserted into a vector for expressing IgG. The obtained vector is introduced into a host bacterium to transform the host bacterium, and then the vector is amplified and purified. The obtained vector can be introduced into a host cell to produce the antibody-producing cell of the present embodiment. The antibody-producing cell can be cultured to produce and accumulate an 8-OHdG antibody or an antibody fragment thereof, and the anti-8-OHdG antibody or the antibody fragment thereof of the first embodiment can be produced from the culture. The host cell into which the vector can be introduced is not particularly limited as long as the vector can be introduced, and any known host cell, for example, a known host cell derived from mammal such as HEK293 cell or CHO cell can be used.

Fifth Embodiment

[Production Method]

A production method of a fifth embodiment of the present invention is such that the antibody-producing cell of the fourth embodiment is cultured to produce and accumulate the antibody or the antibody fragment thereof of the first embodiment, and the antibody or the antibody fragment thereof is collected from the culture. The culturing method, the collecting method, and the like are within the technical scope of those skilled in the art, and appropriate conditions and methods can be suitably used.

Sixth Embodiment

[Measuring Method]

An immunological measuring method of 8-OHdG in a specimen of a sixth embodiment of the present invention uses the antibody or the antibody fragment thereof of the first embodiment. Regarding the measuring method of the present embodiment, an immunological measuring method of 8-OHdG in a specimen, the method including reacting 8-OHdG in a specimen with the anti-8-OHdG antibody or the antibody fragment thereof of the first embodiment, subsequently adding a labeled antibody or a labeled antibody fragment which has been obtained by binding a label to the anti-8-OHdG antibody or the antibody fragment thereof, producing an immune complex composed of 8-OHdG, the anti-8-OHdG antibody or antibody fragment thereof, and the labeled antibody or labeled antibody fragment, and measuring the amount of label in the produced immune complex may be mentioned.

With regard to the measuring method of the present embodiment, examples of the specimen include blood such as serum, plasma, or whole blood, lymph, tissue fluid, spinal fluid, body cavity fluid, digestive juice, nasal mucus, tears, sweat, and urine of animals including humans; however, it is preferable to use urine as the specimen in view of the ease of acquisition and treatment. Furthermore, the specimen may be the specimen itself collected from the subject, or a product obtained by subjecting the collected to treatments such as dilution and concentration, which are usually performed. In addition, the specimen used in the present embodiment may be a specimen collected or prepared at the time of carrying out the measuring method of the present embodiment or may be a specimen that has been collected or prepared in advance and stored.

Here, the immunological measuring method refers to a method of qualitatively or quantitatively measuring the amount of antigen using an antigen-antibody reaction. Examples include ELISA, immunochromatography, chemiluminescence-enzyme immunoassay, chemiluminescence immunoassay, electrochemiluminescence immunoassay, enzyme immunoassay, a fluorescence antibody method, fluorescence enzyme immunoassay, fluorescence polarization immunoassay, a metal particle-labeled antibody electrochemical measurement method, and a latex coagulating method.

8-OHdG in the specimen can be measured by washing the immune complex and then measuring the label in the immune complex. For example, in the case of ELISA, 8-OHdG in the specimen can be measured by reacting an enzyme, which is a label, with a substrate of the enzyme and measuring the absorbance of the product that has developed color (sandwich method). Furthermore, 8-OHdG in the specimen can also be measured by reacting the antibody or the antibody fragment thereof of the present embodiment immobilized on a solid support with 8-OHdG in the specimen, subsequently adding an unlabeled anti-8-OHdG antibody or an antibody fragment thereof (primary antibody), further adding a labeled secondary antibody obtained by enzyme-labeling an antibody (secondary antibody) to this unlabeled anti-8-OHdG antibody or the antibody fragment thereof, and measuring the label of the secondary antibody. 8-OHdG in the specimen can also be measured by labeling the secondary antibody with biotin, causing avidin or streptavidin labeled with an enzyme or the like to bind to biotin, labeling the secondary antibody with an enzyme or the like, and measuring the label of the secondary antibody.

8-OHdG in the specimen can also be measured by adding an unlabeled anti-8-OHdG antibody or an antibody fragment thereof (primary antibody) to 8-OHdG or a conjugate of 8-OHdG and a protein such as BSA immobilized on a solid support to produce an immune complex composed of 8-OHdG and the primary antibody on the solid support, adding the specimen, further adding a secondary antibody obtained by labeling an antibody (secondary antibody) against this unlabeled antibody, and measuring the label of the labeled secondary antibody (competitive method).

Regarding the label, in ELISA, enzymes such as peroxidase and alkaline phosphatase; in the RIA method, radioactive substances such as $^{125}$I, $^{131}$I, $^{35}$S, and $^{3}$H; in the FPIA method, fluorescent substances such as fluorescein isothiocyanate, rhodamine, dansyl chloride, phycoerythrin, tetramethylrhodamine isothiocyanate, and near-infrared fluorescent materials; and in the CLIA method, enzymes such as luciferase and β-galactosidase and luminescent substrates that are converted into luminescent substances by each enzyme, and luminescent substances such as luciferin and aequorin can be used. In addition to those, nanoparticles such as colloidal gold and quantum dots can also be used as labels.

Seventh Embodiment

[Kit]

A kit for measuring 8-OHdG in a specimen of a seventh embodiment of the present invention includes the antibody or the antibody fragment thereof of the first embodiment. The kit of the present embodiment may include a labeled antibody or a labeled antibody fragment in which a label is bound to the antibody of or the antibody fragment thereof the first embodiment.

The kit of the present embodiment may further include a reagent necessary for measuring 8-OHdG in a specimen by the immunological measuring method of 8-OHdG in the specimen of the sixth embodiment. Examples of the reagent necessary for measuring 8-OHdG in a specimen include reagents for measuring the anti-8-OHdG antibody or the antibody fragment thereof of the first embodiment; a labeled antibody or a labeled antibody fragment in which a label is bound to the anti-8-OHdG antibody or the antibody fragment thereof; solid supports such as a microtiter plate; and a reagent for measuring labels.

In the case of such a kit, first, the anti-8-OHdG antibody or the antibody fragment thereof of the first embodiment is immobilized on a solid support such as a microtiter plate, an appropriately treated and diluted specimen is added thereto, subsequently the mixture is incubated, and any specimen unbound to the antibody or the antibody fragment thereof is removed by washing. Next, a labeled antibody or a labeled antibody fragment is added and then incubated, and the label on the solid support is measured. For example, when the label is an enzyme, 8-OHdG in a specimen can be measured by adding a substrate of the enzyme to develop color and measuring the color development using a microtiter plate reader or the like.

According to another embodiment, the kit of the present embodiment may include a secondary antibody which is an antibody to the anti-8-OHdG antibody or the antibody fragment thereof of the first embodiment. Examples of the kit include a kit including a solid support such as a microtiter plate; an anti-8-OHdG antibody or an antibody fragment thereof as a primary antibody; a labeled secondary antibody labeled with alkaline phosphatase, peroxidase, or the like, against the anti-8-OHdG antibody or the antibody fragment thereof, as a secondary antibody; and a substrate for alkaline phosphatase such as pNPP, or a substrate for peroxidase such as DAB, TMB, or OPD.

In the case of such a kit, first, the antibody or the antibody fragment thereof of the first embodiment is immobilized on a solid support such as a microtiter plate, an appropriately treated and diluted specimen is added thereto, subsequently the mixture is incubated, and any specimen unbound to the antibody or the antibody fragment thereof is removed by washing. Subsequently, a primary antibody is added thereto, the mixture is incubated, subsequently washing is performed, an enzyme-labeled secondary antibody that recognizes the primary antibody is further added, and the mixture is incubated. Subsequently, a substrate for the labeling enzyme is added to develop color, the color development is measured using a microplate reader or the like, and thereby 8-OHdG in the specimen can be measured.

Alternatively, 8-OHdG or a conjugate of 8-OHdG and a protein such as BSA is immobilized on a solid support such as a microtiter plate, and the antibody or the antibody fragment thereof of the first embodiment is added thereto, an appropriately treated and diluted specimen is added, subsequently the mixture is incubated, and any specimen unbound to the antibody or the antibody fragment thereof is removed by washing. Subsequently, an enzyme-labeled secondary antibody that recognizes the primary antibody is added thereto, and the mixture is incubated. Subsequently, a substrate for the labeling enzyme is added to develop color, the color development is measured using a microplate reader or the like, and thereby 8-OHdG in the specimen can be measured.

Eighth Embodiment

[Device]

A device for measuring 8-OHdG in a specimen of an eighth embodiment of the present invention includes the antibody or the antibody fragment thereof of the first embodiment. The device of the present embodiment may include a labeled antibody or a labeled antibody fragment in which a label is bound to the antibody or the antibody fragment thereof of the first embodiment.

The device of the present embodiment may further include a member necessary for measuring 8-OHdG in a specimen by the immunological measuring method of 8-OHdG in a specimen of the sixth embodiment. Examples of the member necessary for measuring 8-OHdG in a specimen include the anti-8-OHdG antibody or the antibody fragment thereof of the first embodiment, a labeled antibody or a labeled antibody fragment in which a label is bound to the anti-8-OHdG antibody or the antibody fragment thereof, a substrate including a solid support such as a microtiter plate, and a specimen-adding unit for adding a specimen to the substrate, a reaction unit for performing an antigen-antibody reaction, as well as a measuring unit for measuring a label.

In the case of such a device, first, an appropriately treated and diluted specimen is added, at the specimen-adding unit, to a substrate including a solid support such as a microtiter plate having the anti-8-OHdG antibody or the antibody fragment thereof of the first embodiment immobilized thereon, and the mixture is incubated in the reaction unit. Subsequently, any unreacted specimen is removed by washing, next a labeled antibody or a labeled antibody fragment is added, subsequently the mixture is incubated, and the label on the solid support is measured by the measuring unit. For example, when the label is an enzyme, 8-OHdG in the specimen can be measured by adding a substrate for the enzyme to develop color and measuring the color development by means of the measuring unit such as a microtiter plate reader.

According to another embodiment, the device of the present embodiment may include a secondary antibody which is an antibody to the anti-8-OHdG antibody or the antibody fragment thereof of the first embodiment. Examples of the device include a device that includes a substrate including a solid support such as a microtiter plate, an anti-8-OHdG antibody or an antibody fragment thereof as a primary antibody, a labeled secondary antibody labeled with alkaline phosphatase, peroxidase, or the like, against the anti-8-OHdG antibody or the antibody fragment thereof, as a secondary antibody; and a substrate for alkaline phosphatase such as pNPP, or a substrate for peroxidase such as DAB, TMB or OPD.

In the case of such a device, first, an appropriately treated and diluted specimen is added, at the specimen-adding unit, to a substrate including a solid support such as a microtiter plate having the anti-8-OHdG antibody or the antibody fragment thereof of the first embodiment immobilized thereon, and the mixture is incubated in the reaction unit. Subsequently, any unreacted specimen is removed by washing by means of the washing unit, next a primary antibody is added, the mixture is incubated, subsequently washing is performed, an enzyme-labeled secondary antibody that recognizes the primary antibody is further added, and incubation is performed. Subsequently, a substrate for the labeling enzyme is added to develop color, the color development is measured by the measuring unit such as a microplate reader, and thereby 8-OHdG in the specimen can be measured.

Alternatively, the antibody or the antibody fragment thereof of the first embodiment is added to a substrate including a solid support such as a microtiter plate having 8-OHdG or a conjugate of 8-OHdG and a protein such as BSA immobilized thereon, an appropriately treated and diluted specimen is added thereto by means of the specimen-adding unit, and then the mixture is incubated in the reaction unit. Subsequently, any unreacted specimen is removed by washing, an enzyme-labeled secondary antibody that recognizes the primary antibody is added, and the mixture is incubated. Subsequently, a substrate for the labeling enzyme is added to develop color, the color development is measured by the measuring unit such as a microplate reader, and thereby 8-OHdG in the specimen can be measured.

As described above, according to the antibody or the antibody fragment thereof of the first embodiment, 8-OHdG in a specimen, particularly urine, can be measured conveniently with high sensitivity, without having 8-OHdG in the specimen, particularly urine, affected by an analog of 8-OHdG and urea.

According to the nucleic acid of the second embodiment, an antibody or an antibody fragment thereof which can measure 8-OHdG in a specimen, particularly urine, conveniently with high sensitivity without having 8-OHdG in the specimen, particularly urine, affected by an analog of 8-OHdG and urea can be produced.

According to the IgG vector of the third embodiment, an antibody or an antibody fragment thereof which can measure 8-OHdG in a specimen, particularly urine, conveniently with high sensitivity without having 8-OHdG in the specimen, particularly urine, affected by an analog of 8-OHdG and urea can be produced.

According to the antibody-producing cell of the fourth embodiment, an antibody or an antibody fragment thereof which can measure 8-OHdG in a specimen, particularly urine, conveniently with high sensitivity without having 8-OHdG in the specimen, particularly urine, affected by an analog of 8-OHdG and urea can be produced.

According to the production method of the fifth embodiment, an antibody or an antibody fragment thereof which can measure 8-OHdG in a specimen, particularly urine, conveniently with high sensitivity without having 8-OHdG in the specimen, particularly urine, affected by an analog of 8-OHdG and urea can be produced.

According to the measuring method of the sixth embodiment, 8-OHdG in a specimen, particularly urine, can be measured conveniently with high sensitivity, without being affected by an analog of 8-OHdG and urea.

According to the kit of the seventh embodiment, 8-OHdG in a specimen, particularly urine, can be measured conveniently with high sensitivity without being affected by an analog of 8-OHdG and urea.

According to the device of the eighth embodiment, 8-OHdG in a specimen, particularly urine, can be measured conveniently with high sensitivity without being affected by an analog of 8-OHdG and urea.

EXAMPLES

Hereinafter, the present invention will be described in more detail by way of specific Examples; however, the present invention is not intended to be limited to these Examples.

Example 1

A rabbit was inoculated with an antigen in which 8-OHdG was immobilized by succinylation to keyhole limpet hemocyanin, and messenger RNA was extracted from total RNA isolated from either or both of the bone marrow and spleen tissues, in which the rabbit produced an antibody. cDNA was synthesized using messenger RNA as a template, an antibody sequence region of the cDNA was amplified and inserted into a phagemid vector, and the phagemid vector having the antibody sequence region inserted therein was used to transform a bacterium. Nucleic acids containing the antibody sequence region were extracted from the bacterium to create a gene library, and each nucleic acid containing the antibody sequence region in the gene library was individually used to transform a bacterium, while the bacterium was also infected with helper phages. Next, phages were extracted from the bacterial culture supernatant to create a phage library, positive phage clones were screened by a biopanning method in which an immobilized antigen and a phage antibody in the phage library are subjected to an antigen-antibody reaction, nucleic acids were extracted from the positive phage clones, genetic information was decoded, and the antibody sequence region was inserted into a vector for expressing IgG. The obtained vector was introduced into a host bacterium to transform the host bacterium, and the vector was amplified and purified. The obtained vector was introduced into a host cell to produce an antibody-producing cell, and a plurality of IgG antibodies were produced.

Among the positive phage clones obtained as described above, particularly regarding R4B-A4, R4B-B1, R4B-C1, R4B-D9, R4B-E5, R4B-G1, R4B-G10, R4B-G5, R4B-H2, R4B-H6, R4B-D4, R4B-C4, R4S-A12, R4S-A2, R4S-B2, R4S-B7, R4S-C5, R4S-F12, R4S-G2, R4S-C9, R4S-C3, R4S-A7 and R4S-A11, which are clones having high selectivity for 8-OHdG, the amino acid sequences of CDR1 to CDR3 thereof are shown in Tables 5 to 8, and the amino acid sequences of FR1 to FR4 thereof are shown in Tables 9 to 12.

TABLE 5

| Clone name | Sequence No. | Variable region | CDR | Amino acid sequence |
|---|---|---|---|---|
| R4B-A4 | 5 | VH | 1 | GFSPSTYG |
| | 6 | | 2 | INEWGNI |
| | 7 | | 3 | ASEVWGSRVFNI |
| | 8 | VL | 1 | QSVYSKNY |
| | 9 | | 2 | RAS |

TABLE 5-continued

| Clone name | Sequence No. | Variable region | CDR | Amino acid sequence |
|---|---|---|---|---|
| | 10 | | 3 | LGSYDARSGDSNV |
| R4B-B1 | 11 | VH | 1 | GTSLSTYG |
| | 6 | | 2 | INEWGNI |
| | 7 | | 3 | ASEVWGSRVFNI |
| | 8 | VL | 1 | QSVYSKNY |
| | 9 | | 2 | RAS |
| | 10 | | 3 | LGSYDARSGDSNV |
| R4B-C1 | 11 | VH | 1 | GFSLSTYG |
| | 12 | | 2 | INEWGNV |
| | 7 | | 3 | ASEVWGSRVEN1 |
| | 8 | VL | 1 | QSVYSKNY |
| | 9 | | 2 | RAS |
| | 10 | | 3 | LGSYDARSGDSNV |
| R4B-D9 | 11 | VH | 1 | GFSLSTYG |
| | 6 | | 2 | INEWGNI |
| | 7 | | 3 | ASEVWGSRVFNI |
| | 8 | VL | 1 | QSVYSKNY |
| | 9 | | 2 | RAS |
| | 10 | | 3 | LGSYDARSGDSNV |
| R4B-E5 | 11 | VH | 1 | GFSLSTYG |
| | 6 | | 2 | INEWGNI |
| | 13 | | 3 | ASLIWGSRVTNI |
| | 8 | VL | 1 | QSVYSKNY |
| | 9 | | 2 | RAS |
| | 14 | | 3 | LGSYDARYGDSNV |
| R4B-G1 | 11 | VH | 1 | GFSLSTYG |
| | 6 | | 2 | INEWGNI |
| | 7 | | 3 | ASEVWGSRVFNI |
| | 8 | VL | 1 | QSVYSKNY |
| | 9 | | 2 | RAS |
| | 10 | | 3 | LGSYDARSGDSNV |
| R4B-G10 | 11 | VH | 1 | GFSLSTYG |
| | 6 | | 2 | INEWGNI |
| | 13 | | 3 | ASEIWGSRVFNI |
| | 8 | VL | 1 | QSVYSKNY |
| | 9 | | 2 | RAS |
| | 15 | | 3 | LGSYDARYSDSNV |
| R4B-G5 | 11 | VH | 1 | GFSLSTYG |
| | 6 | | 2 | INEWGNI |
| | 7 | | 3 | ASEVWGSRVFNI |
| | 8 | VL | 1 | QSVYSKNY |
| | 9 | | 2 | RAS |
| | 10 | | 3 | LGSYDARSGDSNV |
| R4B-H2 | 11 | VH | 1 | GFSLSTYG |
| | 16 | | 2 | INEWGHI |
| | 13 | | 3 | ASEIWGSRVFNI |
| | 8 | VL | 1 | QSVYSKNY |
| | 9 | | 2 | RAS |
| | 10 | | 3 | LGSYDARSGDSNV |
| R4B-H6 | 11 | VH | 1 | GFSLSTYG |
| | 6 | | 2 | INEWGNI |
| | 7 | | 3 | ASEVWGSRVFNI |
| | 8 | VL | 1 | QSVYSKNY |
| | 9 | | 2 | RAS |
| | 10 | | 3 | LGSYDARSGDSNV |

TABLE 6

| Clone name | Sequence No. | Variable region | CDR | Amino acid sequence |
|---|---|---|---|---|
| R4B-D4 | 11 | VH | 1 | GFSLSTYG |
| | 6 | | 2 | INEWGNI |
| | 7 | | 3 | ASEVWGSRVFNI |
| | 8 | VL | 1 | QSVYSKNY |

TABLE 6-continued

| Clone name | Sequence No. | Variable region | CDR | Amino acid sequence |
|---|---|---|---|---|
| | 9 | | 2 | RAS |
| | 10 | | 3 | LGSYDARSGDSNV |
| R4B-C4 | 11 | VH | 1 | GFSLSTYG |
| | 6 | | 2 | INEWGNI |
| | 7 | | 3 | ASEVWGSRVFNI |
| | 69 | VL | 1 | QSVYGKNY |
| | 9 | | 2 | RAS |
| | 10 | | 3 | LGSYDARSGDSNV |

TABLE 7

| Clone name | Sequence No. | Variable region | CDR | Amino acid sequence |
|---|---|---|---|---|
| R4S-A12 | 11 | VH | 1 | GFSLSTYG |
| | 6 | | 2 | INEWGNI |
| | 13 | | 3 | ASEIWGSRVFNI |
| | 8 | VL | 1 | QSVYSKNY |
| | 9 | | 2 | RAS |
| | 10 | | 3 | LGSYDARSGDSNV |
| R4S-A2 | 11 | VH | 1 | GFSLSTYG |
| | 6 | | 2 | INEWGNI |
| | 7 | | 3 | ASEVWGSRVFNI |
| | 8 | VL | 1 | QSVYSKNY |
| | 9 | | 2 | RAS |
| | 10 | | 3 | LGSYDARSGDSNV |
| R4S-B2 | 11 | VH | 1 | GFSLSTYG |
| | 6 | | 2 | INEWGNI |
| | 13 | | 3 | ASEIWGSRVFNI |
| | 8 | VL | 1 | QSVYSKNY |
| | 9 | | 2 | RAS |
| | 10 | | 3 | LGSYDARSGDSNV |
| R4S-B7 | 11 | VH | 1 | GFSLSTYG |
| | 6 | | 2 | INEWGNI |
| | 7 | | 3 | ASEVWGSRVFNI |
| | 8 | VL | 1 | QSVYSKNY |
| | 9 | | 2 | RAS |
| | 10 | | 3 | LGSYDARSGDSNV |
| R4S-C5 | 17 | VH | 1 | GFSLMTYG |
| | 6 | | 2 | INEWGNI |
| | 7 | | 3 | ASEVWGSRVFNI |
| | 18 | VL | 1 | QSVYNKNY |
| | 9 | | 2 | RAS |
| | 10 | | 3 | LGSYDARSGDSNV |
| R4S-F12 | 11 | VH | 1 | GFSLSTYG |
| | 6 | | 2 | INEWGNI |
| | 7 | | 3 | ASEVWGSRVFNI |
| | 8 | VL | 1 | QSVYSKNY |
| | 9 | | 2 | RAS |
| | 10 | | 3 | LGSYDARSGDSNV |
| R4S-G2 | 11 | VH | 1 | GFSLSTYG |
| | 19 | | 2 | INEWGFI |
| | 13 | | 3 | ASEIWGSRVFNI |
| | 8 | VL | 1 | QSVYSKNY |
| | 9 | | 2 | RAS |
| | 10 | | 3 | LGSYDARSGDSNV |

TABLE 8

| Clone name | Sequence No. | Variable region | CDR | Amino acid sequence |
|---|---|---|---|---|
| R4S-C9 | 11 | VH | 1 | GFSLSTYG |
| | 6 | | 2 | INEWGNI |
| | 70 | | 3 | ASEVWGSRVFNV |

TABLE 8-continued

| Clone name | Sequence No. | Variable region | CDR | Amino acid sequence |
|---|---|---|---|---|
| | 8 | VL | 1 | QSVYSKNY |
| | 9 | | 2 | RAS |
| | 10 | | 3 | LGSYDARSGDSNV |
| R4S-C3 | 11 | VH | 1 | GFSLSTYG |
| | 71 | | 2 | INEWGTL |
| | 7 | | 3 | ASEVWGSRVFNI |
| | 8 | VL | 1 | QSVYSKNY |
| | 9 | | 2 | RAS |
| | 10 | | 3 | LGSYDARSGDSNV |
| R4S-A7 | 11 | VH | 1 | GFSLSTYG |
| | 6 | | 2 | INEWGNI |
| | 13 | | 3 | ASEIWGSRVFNI |
| | 8 | VL | 1 | QSVYSKNY |
| | 9 | | 2 | RAS |
| | 10 | | 3 | LGSYDARSGDSNV |
| R4S-A11 | 11 | VH | 1 | GFSLSTYG |
| | 6 | | 2 | INEWGNI |
| | 7 | | 3 | ASEVWGSRVFNI |
| | 8 | VL | 1 | QSVYSKNY |
| | 9 | | 2 | RAS |
| | 10 | | 3 | LGSYDARSGDSNV |

TABLE 9

| Clone name | Sequence No. | Variable region | FR | Amino acid sequence |
|---|---|---|---|---|
| R4B-A4 | 31 | VH | 1 | QSVKESGGGLFKPTDTLTLTCTVS |
| | 44 | | 2 | VSWVRQAPGIGLDWIGN |
| | 46 | | 3 | FYASWAKSRSTITRNTNENTVTLKMTSLTAADTATYFC |
| | 50 | | 4 | WGPGTLVTVSS |
| | 52 | VL | 1 | AIKMTQTPSSVSAAVGGTVTINCQAS |
| | 60 | | 2 | LSWFQQKPGQPPKQLIY |
| | 63 | | 3 | NLASGVPSRFSGSGSGTQFTLTISSVQCDDAATYYC |
| | 30 | | 4 | FGGGTEVVVK |
| R4B-B1 | 32 | VH | 1 | QSVEESGGGLFKPTDTLTLTCTVS |
| | 44 | | 2 | VSWVRQAPGIGLDWIGN |
| | 47 | | 3 | YYASWAKSRSTITRNTNENTVTLKMTSLTAADTATYFC |
| | 50 | | 4 | WGPGTLVTVSS |
| | 53 | VL | 1 | AQVMTQTPSSVSAAVGGTVTINCQSS |
| | 60 | | 2 | LSWFQQKPGQPPKQLIY |
| | 64 | | 3 | NLASGVPSRFSGSGSGTEFTLTISSVQCDDAATYYC |
| | 30 | | 4 | FGGGTEVVVK |
| R4B-C1 | 33 | VH | 1 | QTVKESGGGLFKPTDTLTLTCTVS |
| | 44 | | 2 | VSWVRQAPGIGLDWIGN |
| | 47 | | 3 | YYASWAKSRSTITRNTNENTVTLKMTSLTAADTATYFC |
| | 50 | | 4 | WGPGTLVTVSS |
| | 54 | VL | 1 | AQVLTQTPSSVSAAVGGTVTINCQAS |
| | 60 | | 2 | LSWFQQKPGQPPKQLIY |
| | 65 | | 3 | NLASGVPSRFSGSGSGTEFTLTISDVQCDDAATYYC |
| | 30 | | 4 | FGGGTEVVVK |
| R4B-D9 | 34 | VH | 1 | QSVKESGGGLFKPTDTLTLTCTVS |
| | 44 | | 2 | VSWVRQAPGIGLDWIGN |
| | 46 | | 3 | FYASWAKSRSTITRNTNENTVTLKMTSLTAADTATYFC |
| | 51 | | 4 | WGPGTPVTVSS |
| | 54 | VL | 1 | AQVLTQTPSSVSAAVGGTVTINCQAS |
| | 61 | | 2 | LSWFQQKPGQPPRQLIY |
| | 64 | | 3 | NLASGVPSRFSGSGSGTEFTLTISSVQCDDAATYYC |
| | 30 | | 4 | FGGGTEVVVK |
| R4B-E5 | 35 | VH | 1 | QSVKESGGGLFKPADTLTLTCTVS |
| | 43 | | 2 | VSWVRQAPGNGLDWIGN |
| | 48 | | 3 | FYARWAKSRSTITRHTNLNTVTLKMTSLTAADTATYFC |
| | 50 | | 4 | WGPGTLVTVSS |
| | 55 | VL | 1 | AQGLTQTPSSVSAAVGGTVTINCQAS |
| | 60 | | 2 | LSWFQQKPGQPPKQLIY |
| | 66 | | 3 | NLASGVPSRFSGSGSGTEFTLTITSVQCDDAATYYC |
| | 30 | | 4 | FGGGTEVVVK |
| R4B-G1 | 36 | VH | 1 | QSLEESGGGLFKPTDTLTLTCTVS |
| | 44 | | 2 | VSWVRQAPGIGLDWIGN |
| | 47 | | 3 | YYASWAKSRSTITRNTNENTVTLKMTSLTAADTATYFC |
| | 50 | | 4 | WGPGTLVTVSS |
| | 56 | VL | 1 | ALVLTQTPSSVSAAVGGTVTINCQAS |
| | 60 | | 2 | LSWFQQKPGQPPKQLIY |
| | 65 | | 3 | NLASGVPSRFSGSGSGTEFTLTISDVQCDDAATYYC |
| | 30 | | 4 | FGGGTEVVVK |

TABLE 10

| Clone name | Sequence No. | Variable region | FR | Amino acid sequence |
|---|---|---|---|---|
| R4B-G10 | 37 | VH | 1 | QEQQKESEGGLFKPADTLTLTCTVS |
| | 43 | | 2 | VSWVRQAPGNGLDWIGN |
| | 48 | | 3 | FYARWAKSRSTITRHTNLNTVTLKMTSLTAADTATYFC |
| | 50 | | 4 | WGPGTLVTVSS |
| | 57 | VL | 1 | AQGMTQTPSSVSAAVGGTVTINCQAS |
| | 60 | | 2 | LSWFQQKPGQPPKQLIY |
| | 66 | | 3 | NLASGVPSRFSGSGSGTEFTLTITSVQCDDAATYYC |
| | 30 | | 4 | FGGGTEVVVK |
| R4B-G5 | 38 | VH | 1 | QSVKESRGGLFKPTDTLTLTCTVS |
| | 44 | | 2 | VSWVRQAPGIGLDWIGN |
| | 46 | | 3 | FYASWAKSRSTITRNTNENTVTLKMTSLTAADTATYFC |
| | 50 | | 4 | WGPGTLVTVSS |
| | 57 | VL | 1 | AQGMTQTPSSVSAAVGGTVTINCQAS |
| | 60 | | 2 | LSWFQQKPGQPPKQLIY |
| | 65 | | 3 | NLASGVPSRFSGSGSGTEFTLTISDVQCDDAATYYC |
| | 30 | | 4 | FGGGTEVVVK |
| R4B-H2 | 39 | VH | 1 | QTVKESGGGLFKPADTLTLTCTVS |
| | 43 | | 2 | VSWVRQAPGNGLDWIGN |
| | 49 | | 3 | YYASWAKSRSTITRNTNLNTVTLKMTSLTAADTATYFC |
| | 50 | | 4 | WGPGTLVTVSS |
| | 56 | VL | 1 | ALVLTQTPSSVSAAVGGTVTINCQAS |
| | 61 | | 2 | LSWFQQKPGQPPRQLIY |
| | 67 | | 3 | NLASGVPSRFSGSGSGAEFTLTISSVQCDDAATYYC |
| | 30 | | 4 | FGGGTEVVVK |
| R4B-H6 | 32 | VH | 1 | QSVEESGGGLFKPTDTLTLTCTVS |
| | 44 | | 2 | VSWVRQAPGIGLDWIGN |
| | 47 | | 3 | YYASWAKSRSTITRNTNENTVTLKMTSLTAADTATYFC |
| | 50 | | 4 | WGPGTLVTVSS |
| | 55 | VL | 1 | AQGLTQTPSSVSAAVGGTVTINCQAS |
| | 60 | | 2 | LSWFQQKPGQPPKQLIY |
| | 64 | | 3 | NLASGVPSRFSGSGSGTEFTLTISSVQCDDAATYYC |
| | 30 | | 4 | FGGGTEVVVK |
| R4B-D4 | 31 | VH | 1 | QSVKESGGGLFKPTDTLTLTCTVS |
| | 44 | | 2 | VSWVRQAPGIGLDWIGN |
| | 46 | | 3 | FYASWAKSRSTITRNTNENTVTLKMTSLTAADTATYFC |
| | 51 | | 4 | WGPGTPVTVSS |
| | 54 | VL | 1 | AQVLTQTPSSVSAAVGGTVTINCQAS |
| | 61 | | 2 | LSWFQQKPGQPPRQLIY |
| | 64 | | 3 | NLASGVPSRFSGSGSGTEFTLTISSVQCDDAATYYC |
| | 30 | | 4 | FGGGTEVVVK |
| R4S-C4 | 72 | VH | 1 | QEQLKESGGGLFKPTDTLTLTCTVS |
| | 44 | | 2 | VSWVRQAPGIGLDWIGN |
| | 46 | | 3 | FYASWAKSRSTITRNTNENTVTLKMTSLTAADTATYFC |
| | 50 | | 4 | WGPGTLVTVSS |
| | 58 | VL | 1 | ALVMTQTPSSVSAAVGGTVTINCQAS |
| | 60 | | 2 | LSWFQQKPGQPPKQLIY |
| | 65 | | 3 | NLASGVPSRFSGSGSGTEFTLTISDVQCDDAATYYC |
| | 30 | | 4 | FGGGTEVVVK |

TABLE 11

| Clone name | Sequence No. | Variable region | FR | Amino acid sequence |
|---|---|---|---|---|
| R4S-A12 | 35 | VH | 1 | QSVKESGGGLFKPADTLTLTCTVS |
| | 43 | | 2 | VSWVRQAPGNGLDWIGN |
| | 48 | | 3 | FYARWAKSRSTITRHTNLNTVTLKMTSLYAADTATYFC |
| | 50 | | 4 | WGPGTLVTVSS |
| | 58 | VL | 1 | ALVMTQTPSSVSAAVGGTVTINCQAS |
| | 60 | | 2 | LSWFQQKPGQPPKQLIY |
| | 65 | | 3 | NLASGVPSRFSGSGSGTEFTLTISDVQCDDAATYYC |
| | 30 | | 4 | FGGGTEVVVK |
| R4S-A2 | 40 | VH | 1 | QSVKESGGGLVKPGSLTLTCTVS |
| | 44 | | 2 | VSWVRQAPGIGLDWIGN |
| | 46 | | 3 | FYASWAKSRSTITRNTNENTVTLKMTSLTAADTATYFC |
| | 50 | | 4 | WGPGTLVTVSS |
| | 52 | VL | 1 | AIKMTQTPSSVSAAVGGTVTINCQAS |
| | 61 | | 2 | LSWFQQKPGQPPRQLIY |

TABLE 11-continued

| Clone name | Sequence No. | Variable region | FR | Amino acid sequence |
|---|---|---|---|---|
| | 64 | | 3 | NLASGVPSRFSGSGSGTEFTLTISSVQCDDAATYYC |
| | 30 | | 4 | FGGGTEVVVK |
| R4S-B2 | 41 | VH | 1 | QSLGESRGSLFKPADTITLTCTVS |
| | 43 | | 2 | VSWVRQAPGNGLDWIGN |
| | 49 | | 3 | YYASWAKSRSTITRNTNLNTVTLKMTSLTAADTATYFC |
| | 50 | | 4 | WGPGTLVTVSS |
| | 58 | VL | 1 | ALVMTQTPSSVSAAVGGTVTINCQAS |
| | 61 | | 2 | LSWFQQKPGQPPRQLIY |
| | 68 | | 3 | NLASGVPSRFSGSGSGTEFTLTISSAQCDDAATYYC |
| | 30 | | 4 | FGGGTEVVVK |
| R4S-B7 | 33 | VH | 1 | QTVKESGGGLFKPTDTLTLTCTVS |
| | 44 | | 2 | VSWVRQAPGIGLDWIGN |
| | 46 | | 3 | FYASWAKSRSTITRNTNENTVTLKMTSLTAADTATYFC |
| | 50 | | 4 | WGPGTLVTVSS |
| | 59 | VL | 1 | AIQMTQTPSSVSAAVGGTVTINCQAS |
| | 61 | | 2 | LSWFQQKPGQPPRQLIY |
| | 64 | | 3 | NLASGVPSRFSGSGSGTEFTLTISSVQCDDAATYYC |
| | 30 | | 4 | FGGGTEVVVK |
| R4S-C5 | 33 | VH | 1 | QTVKESGGGLFKPTDTLTLTCTVS |
| | 42 | | 2 | VSWVRQAPGFGLDWIGN |
| | 47 | | 3 | YYASWAKSRSTITRNTNENTVTLKMTSLTAADTATYFC |
| | 50 | | 4 | WGPGTLVTVSS |
| | 58 | VL | 1 | ALVMTQTPSSVSAAVGGTVTINCQAS |
| | 62 | | 2 | LSWYQQKPGQPPKQLIY |
| | 64 | | 3 | NLASGVPSRFSGSGSGTEFTLTISSVQCDDAATYYC |
| | 30 | | 4 | FGGGTEVVVK |
| R4S-F12 | 33 | VH | 1 | QTVKESGGGLFKPTDTLTLTCTVS |
| | 45 | | 2 | VSWVRQAPGVGLDWIGN |
| | 47 | | 3 | YYASWAKSRSTITRNTNENTVTLKMTSLTAADTATYFC |
| | 50 | | 4 | WGPGTLVTVSS |
| | 54 | VL | 1 | AQVLTQTPSSVSAAVGGTVTINCQAS |
| | 61 | | 2 | LSWFQQKPGQPPRQIIY |
| | 64 | | 3 | NLASGVPSRFSGSGSGTEFTLTISSVQCDDAATYYC |
| | 30 | | 4 | FGGGTEVVVK |
| R4S-G2 | 35 | VH | 1 | QTVKESGGGLFKPADTLTLTCTVS |
| | 43 | | 2 | VSWVRQAPGNGLDWIGN |
| | 49 | | 3 | YYASWAKSRSTITRNTNLNTVTLKMTSLTAADTATYFC |
| | 50 | | 4 | WGPGTLVTVSS |
| | 54 | VL | 1 | AQVLTQTPSSVSAAVGGTVTINCQAS |
| | 60 | | 2 | LSWFQQKPGQPPKQIIY |
| | 65 | | 3 | NLASGVPSRFSGSGSGTEFTLTISDVQCDDAATYYC |
| | 30 | | 4 | FGGGTEVVVK |

TABLE 12

| Clone name | Sequence No. | Variable region | FR | Amino acid sequence |
|---|---|---|---|---|
| R4S-C9 | 32 | VH | 1 | QSVEESGGGLFKPTDTLTLTCTVS |
| | 44 | | 2 | VSWVRQAPGIGLDWIGN |
| | 47 | | 3 | YYASWAKSRSTITRNTNENTVTLKMTSLTAADTATYFC |
| | 50 | | 4 | WGPGTLVTVSS |
| | 56 | VL | 1 | ALVLTQTPSSVSAAVGGTVTINCQAS |
| | 61 | | 2 | LSWFQQKPGQPPRQLIY |
| | 64 | | 3 | NLASGVPSRFSGSGSGTEFTLTISSVQCDDAATYYC |
| | 30 | | 4 | FGGGTEVVVK |
| R4S-C3 | 33 | VH | 1 | QTVKESGGGLFKPTDTLTLTCTVS |
| | 44 | | 2 | VSWVRQAPGIGLDWIGN |
| | 49 | | 3 | YYASWAKSRSTITRNTNLNTVTLKMTSLTAADTATYFC |
| | 50 | | 4 | WGPGTLVTVSS |
| | 58 | VL | 1 | ALVMTQTPSSVSAAVGGTVTINCQAS |
| | 60 | | 2 | LSWFQQKPGQPPKQLIY |
| | 63 | | 3 | NLASGVPSRFSGSGSGTQFTLTISSVQCDDAATYYC |
| | 30 | | 4 | FGGGTEVVVK |
| R4S-A7 | 39 | VH | 1 | QTVKESGGGLFKPADTLTLTCTVS |
| | 43 | | 2 | VSWVRQAPGNGLDWIGN |

TABLE 12-continued

| Clone name | Sequence No. | Variable region | FR | Amino acid sequence |
|---|---|---|---|---|
| | 48 | | 3 | FYARWAKSRSTITRHTNLNTVTLKMTSLTAADTATYFC |
| | 50 | | 4 | WGPGTLVTVSS |
| | 58 | VL | 1 | ALVMTQTPSSVSAAVGGTVTINCQAS |
| | 60 | | 2 | LSWFQQKPGQPPKQLIY |
| | 64 | | 3 | NLASGVPSRFSGSGSGTEFTLTISSVQCDDAATYYC |
| | 30 | | 4 | FGGGTEVVVK |
| R4S-A11 | 31 | VH | 1 | QSVKESGGGLFKPTDTLTLTCTVS |
| | 44 | | 2 | VSWVRQAPGIGLDWIGN |
| | 46 | | 3 | FYASWAKSRSTITRNTNENTVTLKMTSLTAADTATYFC |
| | 51 | | 4 | WGPGTPVTVSS |
| | 57 | VL | 1 | AQGMTQTPSSVSAAVGGTVTINCQAS |
| | 60 | | 2 | LSWFQQKPGQPPKQLIY |
| | 64 | | 3 | NLASGVPSRFSGSGSGTEFTLTISSVQCDDAATYYC |
| | 30 | | 4 | FGGGTEVVVK |

Example 2

The reactivity of the anti-8-OHdG antibody of the present invention with 8-OHdG, analogs of 8-OHdG, and urea was evaluated using the following competitive ELISA method. As the analogs of 8-OHdG, 2'-deoxyguanosine (dG) and 8-mercaptoguanosine (8-SHG) were used.

A microplate coated with a conjugate antigen of 8-OHdG and BSA was used, 50 μL each of solutions at various concentrations of 8-OHdG, an analog of 8-OHdG, or urea was added to each well, and 50 μL of a solution of the anti-8-OHdG antibody (R4B-E5) obtained in Example 1 was added thereto as a primary antibody. The microplate was incubated at 37° C. for 1 hour and washed with PBS, and then 50 μL of an HRP-labeled anti-rabbit IgG antibody solution was added as a secondary antibody. The microplate was incubated at 37° C. for 1 hour and washed with PBS, subsequently 50 μL of a 3,3',5,5'-tetramethylbenzidine solution was added as a substrate, and after 5 minutes, 50 μL of 2N sulfuric acid was added as a reaction terminator. The OD value at 450 nm was measured with a microplate reader. The results are shown in FIG. 1. The concentrations of 8-OHdG, 8-SHG, and urea which inhibited the immune response between the anti-8-OHdG antibody (R4B-E5) obtained in Example 1 and 8-OHdG by 50% were 130 ng/mL, 70 μg/mL, and 400 mg/mL, respectively.

Example 3

The reactivity of the anti-8-OHdG antibody of the present invention with 8-OHdG, analogs of 8-OHdG, and substances contained in urine was evaluated using the following competitive ELISA method. Regarding the analogs of 8-OHdG, 8-bromoguanosine (8-BrG), guanine, 2'-deoxyadenosine (dA), 2'-deoxyinosine (dI), 2'-deoxycytidine (dC), 2'-deoxythymidine (dT), 2'-deoxyuridine (dU), 7-methylguanosine (7-methylG), 6-O-methylguanine, 6-O-methyldeoxyguanosine (6-O-methyldG), and 6-O-methylguanosine (6-O-methylG) were used, and as the substances contained in urine, uric acid, creatine, and creatinine were used.

Figure 2:
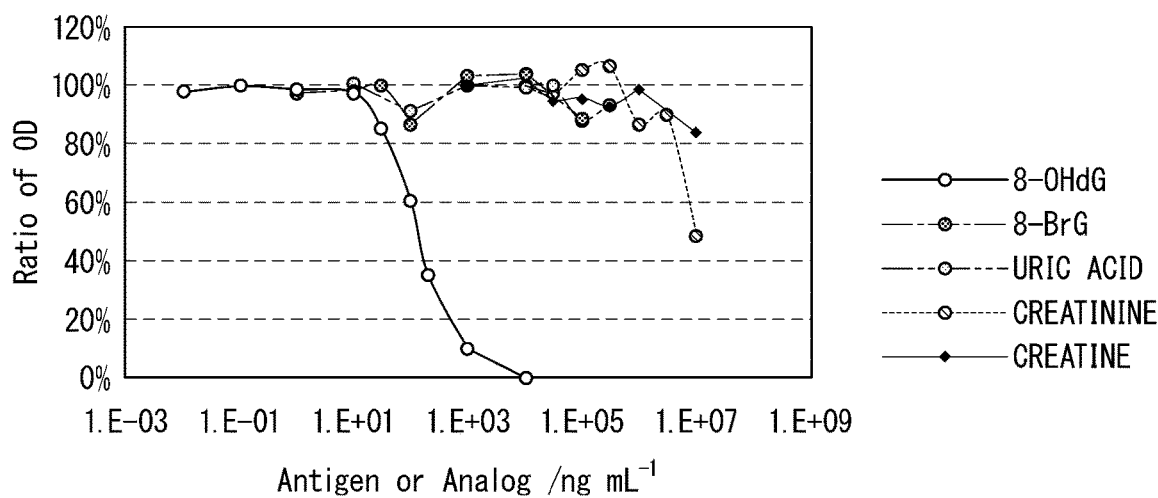
FIG. 2 is a diagram showing the results of measuring the reactivity of the anti-8-OHdG antibody (R4B-E5) of the present invention with 8-OHdG, analogs of 8-OHdG, and substances contained in urine by the competitive ELISA method. In the diagram, the ordinate axis shows the OD value when the OD value obtained at an 8-OHdG concentration in a specimen of 0.1 ng/mL is taken as 100%. The abscissa axis shows the concentration of 8-OHdG, 8-bromoguanosine (8-BrG), uric acid, creatinine, or creatine in the specimen.
Figure 3:
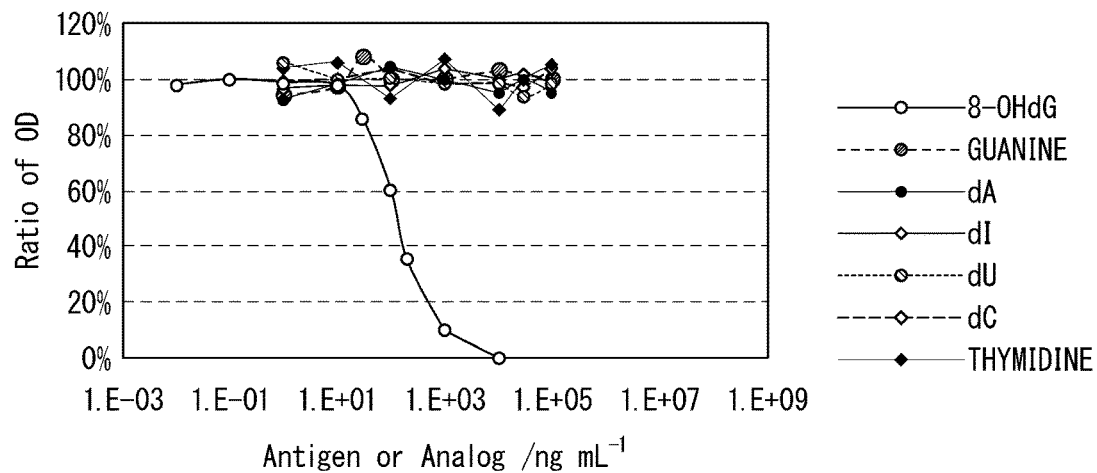
FIG. 3 is a diagram showing the results of measuring the reactivity of the anti-8-OHdG antibody (R4B-E5) of the present invention with 8-OHdG, analogs of 8-OHdG, and substances contained in urine by the competitive ELISA method. In the diagram, the ordinate axis shows the OD value when the OD value obtained at an 8-OHdG concentration in a specimen of 0.1 ng/mL is taken as 100%. The abscissa axis shows the concentration of 8-OHdG, Guanine, T-Deoxyadenosine (2'-deoxyadenosine monohydrate, dA), 2'-Deoxyinosine (dI), and 2'-Deoxycytidine (dC), Thymidine, or 2'-Deoxyuridine (dU) in the specimen.
Figure 4:
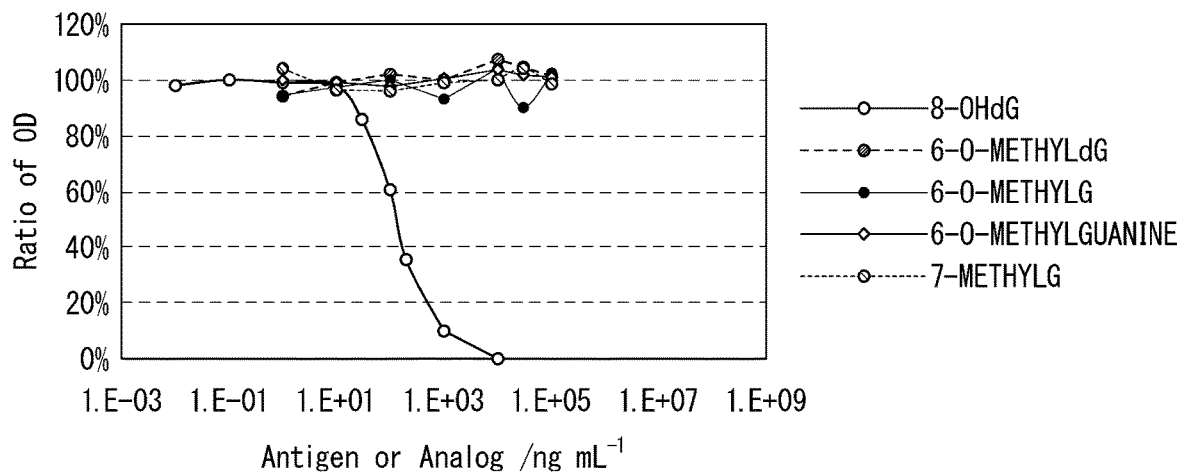
FIG. 4 is a diagram showing the results of measuring the reactivity of the anti-8-OHdG antibody (R4B-E5) of the present invention with 8-OHdG and analogs of 8-OHdG by the competitive ELISA method. In the diagram, the ordinate axis shows the OD value when the OD value obtained at an 8-OHdG concentration in a specimen of 0.1 ng/mL is taken as 100%. The abscissa axis shows the concentration of 8-OHdG, 6-O-methyldeoxyguanosine (6-O-methyl-2'-deoxyguanosine, 6-O-methyldG), 6-O-methylguanosine (6-O-methylG), 6-O-methylguanine, or 7-methylguanine (7-methylG) in the specimen.
Figure 5:
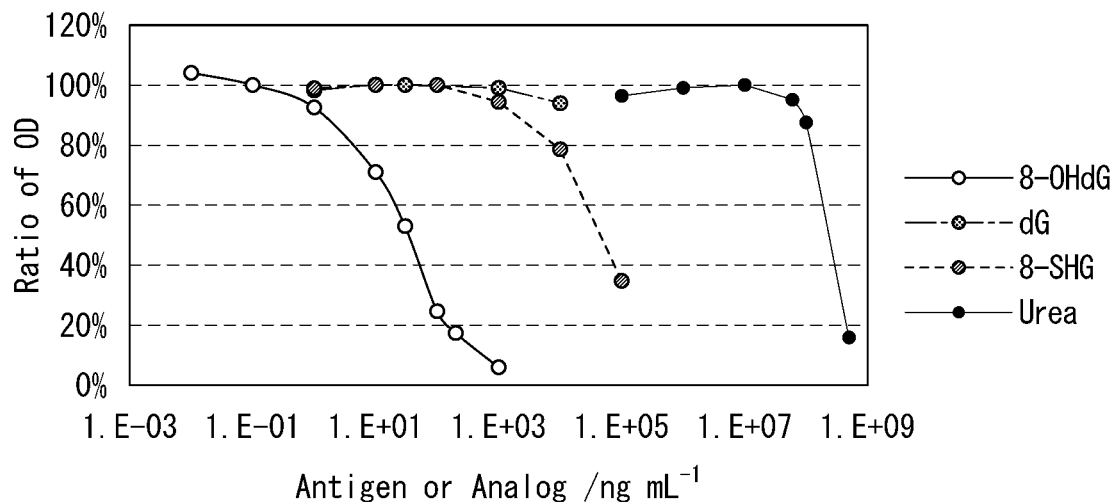
FIG. 5 is a diagram showing the results of measuring the reactivity of the anti-8-OHdG antibody (R4B-E5) of the present invention with 8-OHdG, analogs of 8-OHdG, and urea by the competitive ELISA method. In the diagram, the ordinate axis shows the OD value when the OD value obtained at an 8-OHdG concentration in a specimen of 0.1 ng/mL is taken as 100%. The abscissa axis shows the concentration of 8-OHdG, 8-mercaptoguanosine (8-SHG), 2'-deoxyguanosine (dG), or urea in the specimen.
Figure 6:
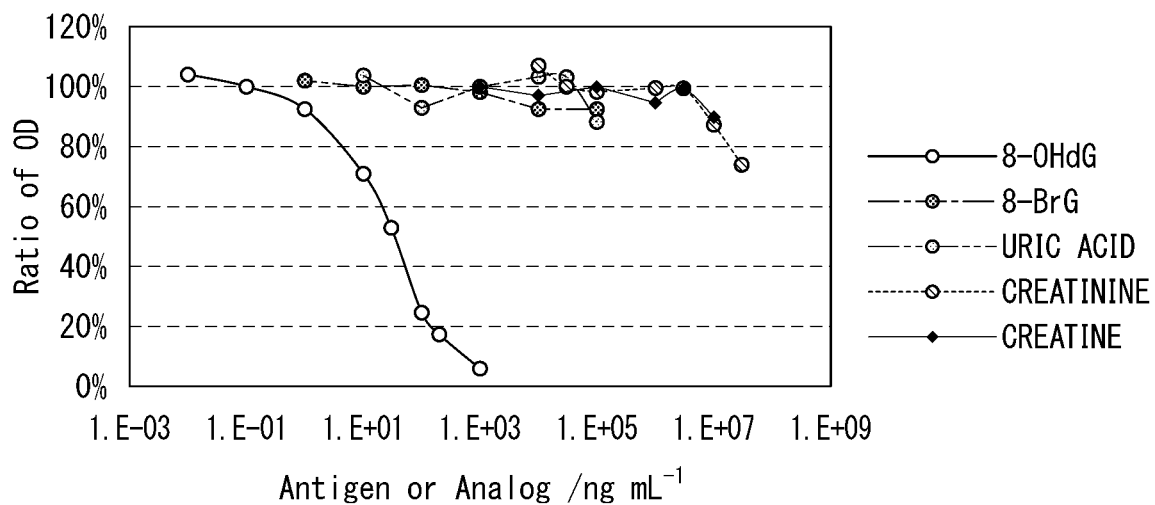
FIG. 6 is a diagram showing the results of measuring the reactivity of the anti-8-OHdG antibody (R4B-E5) of the present invention with 8-OHdG, analogs of 8-OHdG, and substances contained in urine by the competitive ELISA method. In the diagram, the ordinate axis shows the OD value when the OD value obtained at an 8-OHdG concentration in a specimen of 0.1 ng/mL is taken as 100%. The abscissa axis shows the concentration of 8-OHdG, 8-bromoguanosine (8-BrG), uric acid, creatinine, or creatine in the specimen.
Figure 7:
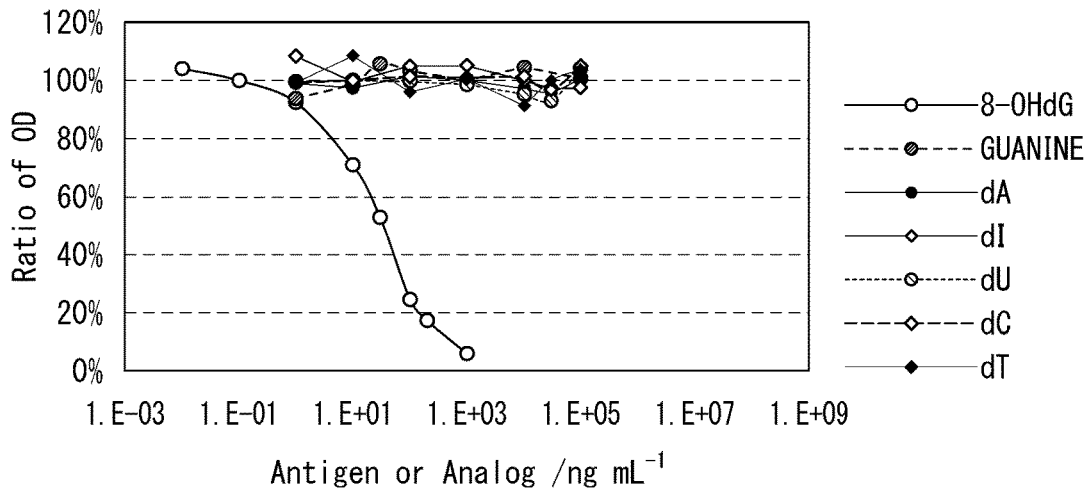
FIG. 7 is a diagram showing the results of measuring the reactivity of the anti-8-OHdG antibody (R4B-E5) of the present invention with 8-OHdG, analogs of 8-OHdG, and substances contained in urine by the competitive ELISA method. In the diagram, the ordinate axis shows the OD value when the OD value obtained at an 8-OHdG concentration in a specimen of 0.1 ng/mL is taken as 100%. The abscissa axis shows the concentration of 8-OHdG, guanine, 2'-deoxyadenosine (2'-deoxyadenosine monohydrate, dA), 2'-deoxyinosine (dI), 2'-deoxyuridine (dU), 2'-deoxycytidine (dC), or 2'-deoxythymidine (dT).
Figure 8:
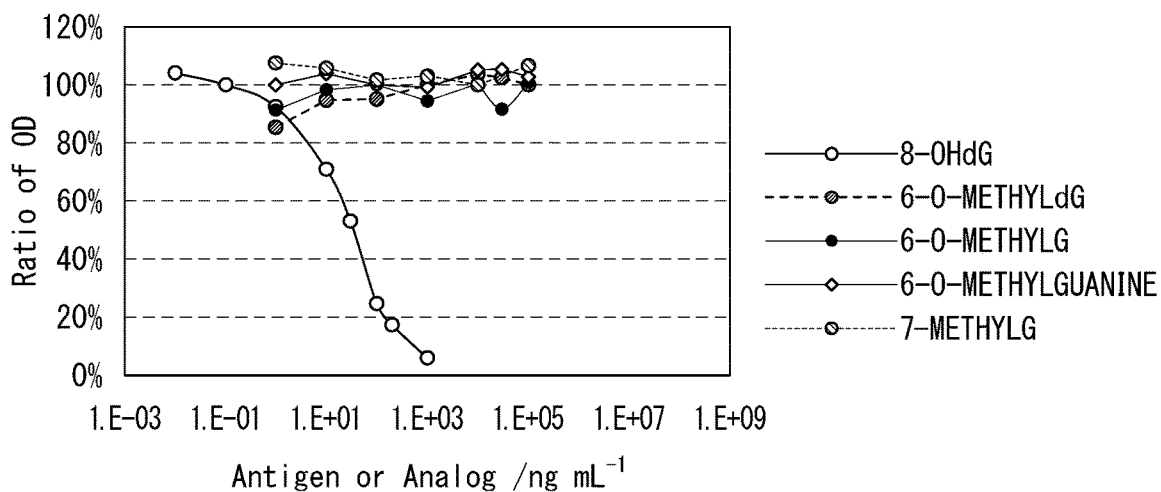
FIG. 8 is a diagram showing the results of measuring the reactivity of the anti-8-OHdG antibody (R4B-E5) of the present invention with 8-OHdG, analogs of 8-OHdG, and urea by the competitive ELISA method. In the diagram, the ordinate axis shows the OD value when the OD value obtained at an 8-OHdG concentration in a specimen of 0.1 ng/mL is taken as 100%. The abscissa axis shows the concentration of 8-OHdG, 6-O-methyldeoxyguanosine (6-O-methyl-2'-deoxyguanosine, 6-O-methyldG), 6-O-methylguanosine (6-O-methylG), 6-O-methylguanine, or 7-methylguanine (7-methylG) in the specimen.

A microplate coated with a conjugate antigen of 8-OHdG and BSA was used, 50 μL each of solutions at various concentrations of 8-OHdG, an analog of 8-OHdG, or urea was added to each well, and 50 μL of a solution of the anti-8-OHdG antibody (R4B-E5) obtained in Example 1 was added thereto as a primary antibody. The microplate was incubated at 37° C. for 1 hour and washed with PBS, and then 50 μL of an HRP-labeled anti-rabbit IgG antibody solution was added as a secondary antibody. The microplate was incubated at 37° C. for 1 hour and washed with PBS, subsequently 50 μL of a 3,3',5,5'-tetramethylbenzidine solution was added as a substrate, and after 5 minutes, 50 μL of 2N sulfuric acid was added as a reaction terminator. The OD value at 450 nm was measured with a microplate reader. The results are shown in FIG. 2 to FIG. 4. The concentration of creatinine that inhibits the immune response between the anti-8-OHdG antibody (R4B-E5) obtained in Example 1 and 8-OHdG by 50% was 90 mg/mL.

Example 4

Evaluation was performed using the competitive ELISA method in the same manner as in Example 2, except that 50 μL of a 3,3',5,5'-tetramethylbenzidine solution was added as a substrate, and after 4 minutes, 50 μL of 2 N sulfuric acid was added as a reaction terminator. The results are shown in FIG. 5 to FIG. 8.

Example 5

Figure 9:
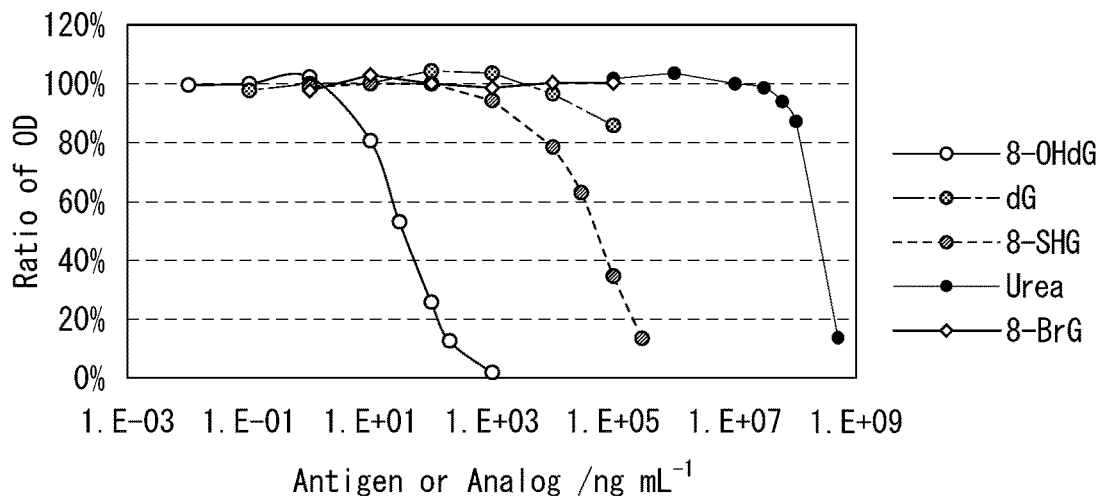
FIG. 9 is a diagram showing the results of measuring the reactivity of the anti-8-OHdG antibody (R4S-B7) of the present invention with 8-OHdG, analogs of 8-OHdG, and urea by the competitive ELISA method. In the diagram, the ordinate axis shows the OD value when the OD value obtained at an 8-OHdG concentration in a specimen of 0.1 ng/mL is taken as 100%. The abscissa axis shows the concentration of 8-OHdG, 8-mercaptoguanosine (8-SHG), 2'-deoxyguanosine (dG), 8-bromoguanosine (8-BrG), or urea in the specimen.

Evaluation was performed using the competitive ELISA method in the same manner as in Example 4, except that the anti-8-OHdG antibody (R4S-B7) obtained in Example 1 was used as the primary antibody, and 2'-deoxyguanosine (dG), 8-mercaptoguanosine (8-SHG), and 8-bromoguanosine (8-BrG) were used as the analogs of 8-OHdG. The results are shown in FIG. 9.

Example 6

Figure 10:
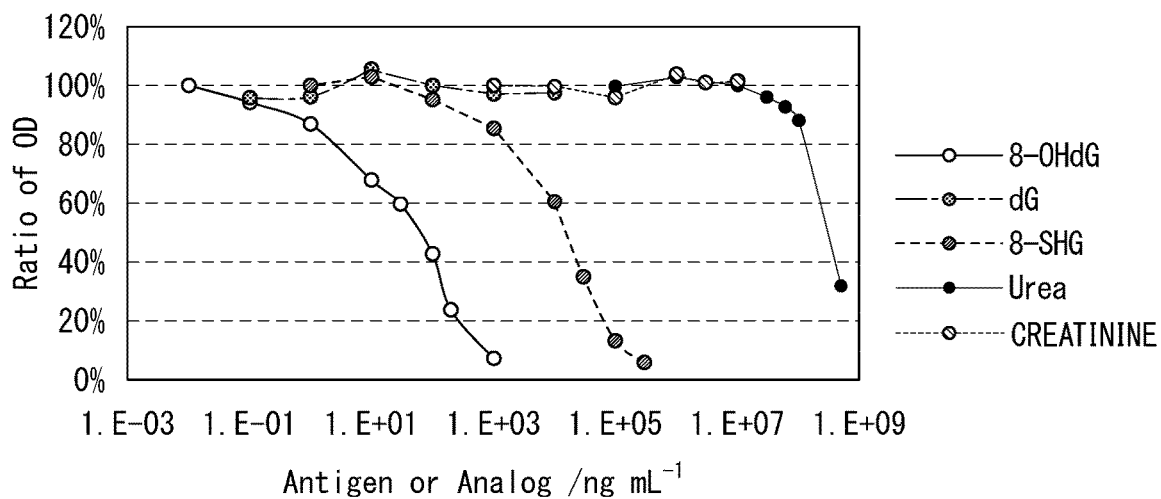
FIG. 10 is a diagram showing the results of measuring the reactivity of the anti-8-OHdG antibody (R4B-G10) of the present invention with 8-OHdG, analogs of 8-OHdG, and urea by the competitive ELISA method. In the diagram, the ordinate axis shows the OD value when the OD value obtained at an 8-OHdG concentration in a specimen of 0.1 ng/mL is taken as 100%. The abscissa axis shows the concentration of 8-OHdG, 8-mercaptoguanosine (8-SHG), 2'-deoxyguanosine (dG), creatinine, or urea in the specimen.

Evaluation was performed using the competitive ELISA method in the same manner as in Example 4, except that the anti-8-OHdG antibody (R4B-G10) obtained in Example 1 was used as the primary antibody, and 2'-deoxyguanosine (dG), 8-mercaptoguanosine (8-SHG), and creatinine were used as the analogs of 8-OHdG. The results are shown in FIG. 10.

Comparative Example 1

Figure 11:
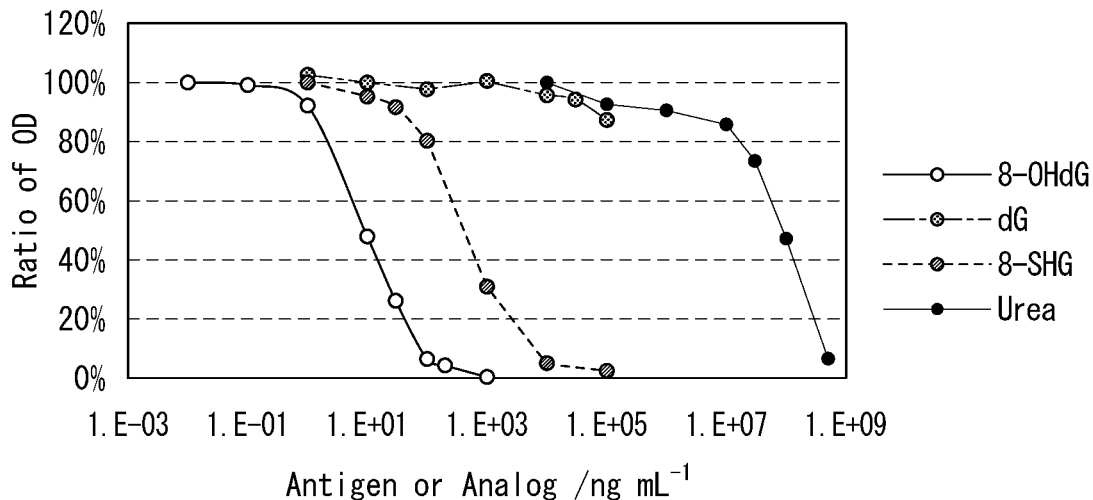
FIG. 11 is a diagram showing the results of measuring the reactivity of N45.1, which is a conventional anti-8-OHdG antibody, with 8-OHdG, analogs of 8-OHdG, and urea by the competitive ELISA method. In the diagram, the ordinate axis shows the OD value when the OD value obtained at an 8-OHdG concentration in a specimen of 0.1 ng/mL is taken as 100%. The abscissa axis shows the concentration of 8-OHdG, 8-mercaptoguanosine (8-SHG), 2'-deoxyguanosine (dG), or urea in the specimen.

The reactivity of N45.1 with 8-OHdG, analogs of 8-OHdG, and urea was evaluated using the competitive ELISA method in the same manner as in Example 2, except that N45.1 (manufactured by Abcam plc), which is a conventional anti-8-OHdG antibody described in Non-Patent Document 1, was used instead of the anti-8-OHdG antibody (R4B-E5). The results are shown in FIG. 11.

Comparative Example 2

Figure 12:
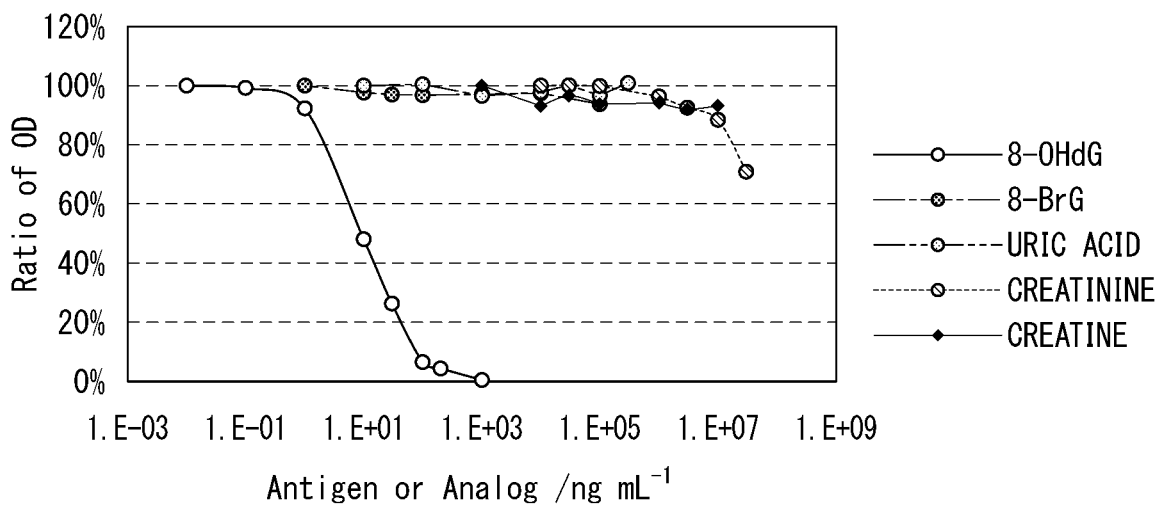
FIG. 12 is a diagram showing the results of measuring the reactivity of N45.1, which is a conventional anti-8-OHdG antibody, with 8-OHdG, analogs of 8-OHdG, and substances contained in urine by the competitive ELISA method. In the diagram, the ordinate axis shows the OD value when the OD value obtained at an 8-OHdG concentration in a specimen of 0.1 ng/mL is taken as 100%. The abscissa axis shows the concentration of 8-OHdG, 8-bromoguanosine (8-BrG), uric acid, creatinine, or creatine in the specimen.
Figure 13:
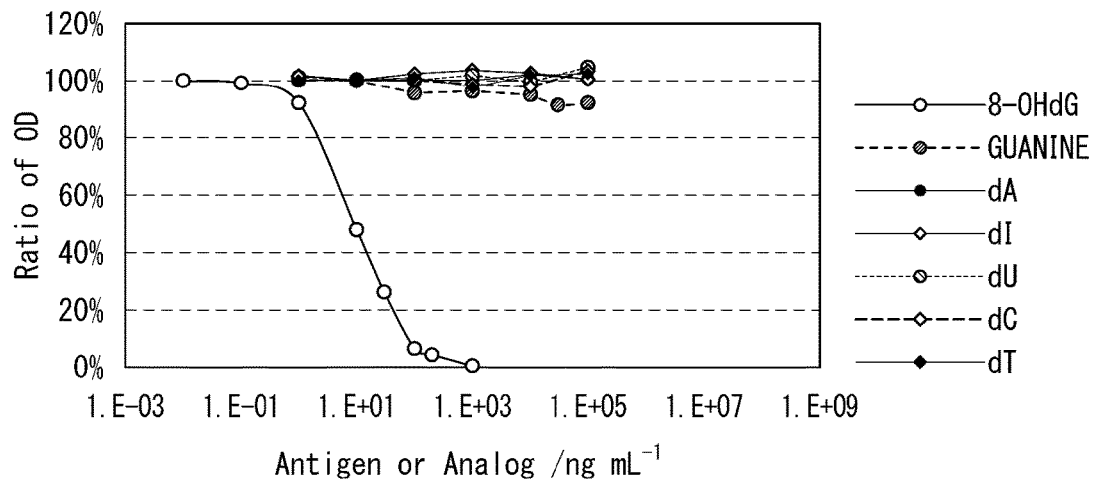
FIG. 13 is a diagram showing the results of measuring the reactivity of N45.1, which is a conventional anti-8-OHdG antibody, with 8-OHdG, analogs of 8-OHdG, and substances contained in urine by the competitive ELISA method. In the diagram, the ordinate axis shows the OD value when the OD value obtained at an 8-OHdG concentration in a specimen of 0.1 ng/mL is taken as 100%. The abscissa axis shows the concentration of 8-OHdG, guanine, 2'-deoxyadenosine (T-deoxyadenosine monohydrate, dA), 2'-deoxyinosine (dI), 2'-deoxycytidine (dC), or 2'-deoxythymidine (dT) in the specimen.
Figure 14:
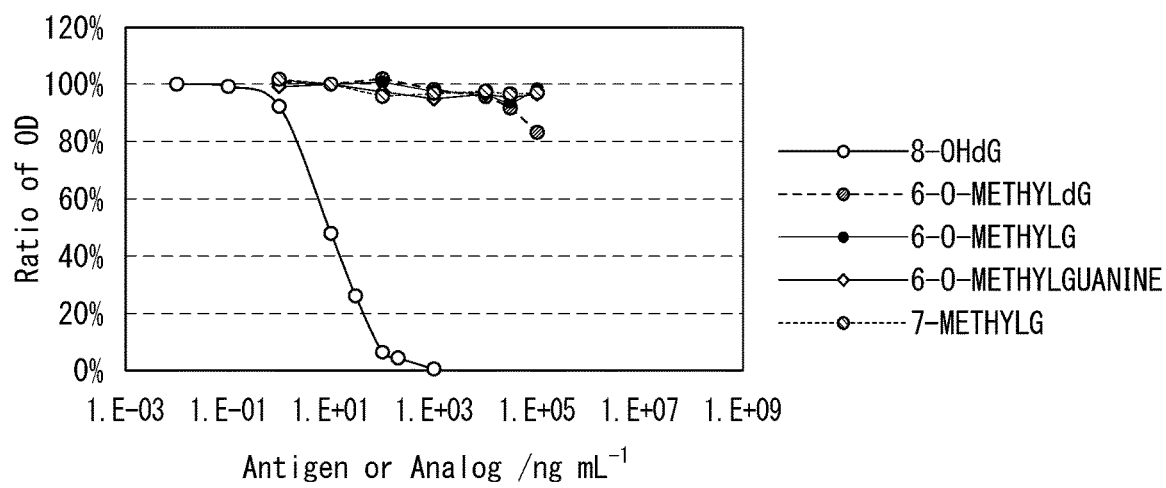
FIG. 14 is a diagram showing the results of measuring the reactivity of N45.1, which is a conventional anti-8-OHdG antibody, with 8-OHdG, analogs of 8-OHdG, and substances contained in urine by the competitive ELISA method. In the diagram, the ordinate axis shows the OD value when the OD value obtained at an 8-OHdG concentration in a specimen of 0.1 ng/mL is taken as 100%. The abscissa axis shows the concentration of 8-OHdG, 6-O-methyldeoxyguanosine (6-O-methyl-2'-deoxyguanosine, 6-O-methyldG), 6-O-methylguanosine (6-O-methylG), 6-O-methylguanine, or 7-methylguanosine (7-methylG) in the specimen.

The reactivity of N45.1 with 8-OHdG, analogs of 8-OHdG, and substances contained in urine was evaluated using the competitive ELISA method in the same manner as in Example 3, except that N45.1 (manufactured by Abcam plc), which is a conventional anti-8-OHdG antibody described in Non-Patent Document 1, was used instead of the anti-8-OHdG antibody (R4B-E5). The results are shown in FIG. 12 to FIG. 14.

As shown in FIGS. 1 to 10, the anti-8-OHdG antibody of the present invention specifically reacted with 8-OHdG but did not react with the analogs of 8-OHdG and the substances contained in urine. Regarding urea, cross-reactivity was not recognized in the concentration range of $1\times10^5$ to $6\times10^7$ ng/mL.

In contrast, with regard to N45.1, which is a conventional anti-8-OHdG antibody, cross-reactivity with 8-mercaptoguanosine, which is an analog of 8-OHdG, was recognized as shown in FIG. 11. Furthermore, with regard to N45.1, cross-reactivity with creatinine was recognized as shown in FIG. 12. In addition, with regard to N45.1, cross-reactivity with urea was recognized in the concentration range of $1\times10^5$ to $6\times10^7$ ng/mL.

From the above-described results, since the specificity of the anti-8-OHdG antibody of the present invention is such that the specificity to 8-OHdG is high and the reactivity with urea is low as compared to the conventional antibody N45.1, 8-OHdG in urine can be accurately measured.

Example 7

A calibration curve of 8-OHdG was created as follows using the anti-8-OHdG antibody of the present invention, by a metal particle-labeled antibody electrochemical measurement method.

A solution of a conjugate of 8-OHdG and BSA was added dropwise onto a carbon electrode to be immobilized thereon, and then blocking was performed with 0.5% casein in order to prevent non-specific adsorption. The anti-8-OHdG antibody (R4B-E5) was used as the anti-8-OHdG antibody of the present invention, a PBS solution of 8-OHdG at each concentration and the anti-8-OHdG antibody were added in this order, and an antigen-antibody reaction was carried out at room temperature for 30 minutes. Next, a gold nanoparticle-labeled IgG secondary antibody (CTD/AC-40-17-05/Rabbit; manufactured by Cytodiagnostics, Inc.) immobilized on the anti-8-OHdG antibody (R4B-E5) was added, reaction was carried out at room temperature for 30 minutes, and an immune complex of electrode-BSA-8-OHdG conjugate-anti-8-OHdG antibody-IgG secondary antibody-gold nanoparticle was formed on the electrode. The electrode was washed with PBS and dried with an air gun, subsequently the electrode was maintained at 1.25 V (based on Ag/AgCl reference electrodes) for 60 seconds in 0.1 M hydrochloric acid as an electrolyte solution using a normal tripolar electrochemical cell to oxidize the gold nanoparticle label into a gold chloride complex, next the gold chloride complex was reduced to metal gold by scanning from 0.6 to 0.2 V (based on Ag/AgCl reference electrodes) with a Differential Potential Voltammetry (DPV), and the reduction current was measured as a potential-current curve. A calibration curve plotting each concentration of 8-OHdG in PBS and the current peak value at the concentration is shown in FIG. 15.

Figure 15:
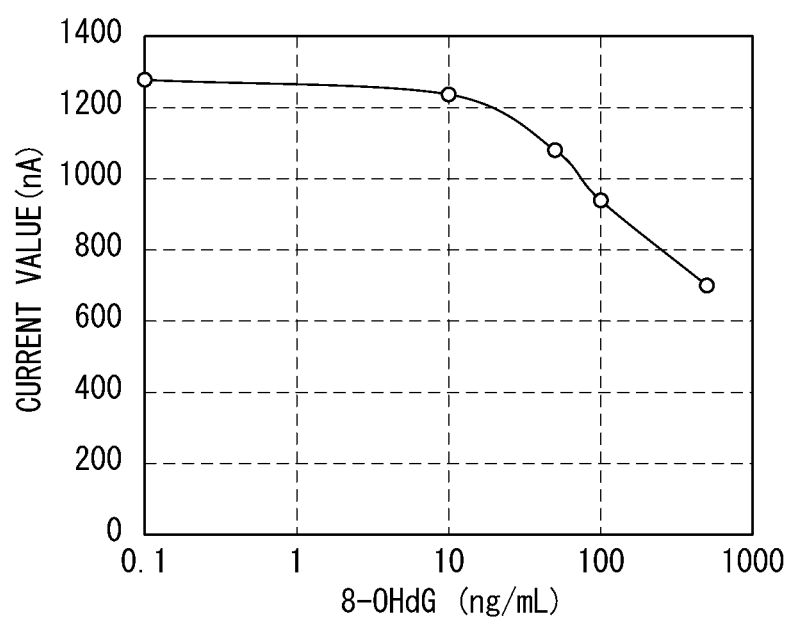
FIG. 15 is a diagram showing the results of measuring the reactivity of the anti-8-OHdG antibody (R4B-E5) of the present invention with 8-OHdG by a metal particle-labeled antibody electrochemical measurement method. In the diagram, the ordinate axis represents the current value, and the abscissa axis represents the concentration of 8-OHdG in the specimen.

As shown in FIG. 15, since a calibration curve can be created using the anti-8-OHdG antibody of the present invention, it was found that the concentration of 8-OHdG in a specimen can be quantified using the anti-8-OHdG antibody of the present invention not only in ELISA but also in a method of electrochemically detecting an antigen-antibody reaction, as immunological measuring methods.

[Sequence Listing]

The invention claimed is:

1. An anti-8-hydroxy-2'-deoxyguanosine antibody ("anti-8-OHdG") or an antibody fragment thereof which specifically reacts with 8-hydroxy-2'-deoxyguanosine and does not react with 30 mg/ml of urea, wherein the antibody is any one antibody selected from the group consisting of the following (1) to (9):

(1) an antibody in which:
the amino acid sequence of CDR1 of the VH includes the amino acid sequence set forth in SEQ ID NO:5,
the amino acid sequence of CDR2 of the VH includes the amino acid sequence set forth in SEQ ID NO:6,
the amino acid sequence of CDR3 of the VH includes the amino acid sequence set forth in SEQ ID NO:7,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(2) an antibody in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes the amino acid sequence set forth in SEQ ID NO:7,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(3) an antibody in which:
the amino acid sequence of CDR1 of the VH includes the amino acid sequence set forth in SEQ ID NO:11,
the amino acid sequence of CDR2 of the VH includes the amino acid sequence set forth in SEQ ID NO:12,
the amino acid sequence of CDR3 of the VH includes the amino acid sequence set forth in SEQ ID NO:7,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

(4) an antibody in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes the amino acid sequence set forth in SEQ ID NO:13,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:14;

(5) an antibody in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes the amino acid sequence set forth in SEQ ID NO:13,
the amino acid sequence of CDR1 of the VL includes the amino acid sequence set forth in SEQ ID NO:8, the amino acid sequence of CDR2 of the VL includes
the amino acid sequence set forth in SEQ ID NO:9,
and the amino acid sequence of CDR3 of the VL includes
the amino acid sequence set forth in SEQ ID NO:15;

(6) an antibody in which:

the amino acid sequence of CDR1 of the VH includes
the amino acid sequence set forth in SEQ ID NO:11, the amino acid sequence of CDR2 of the VH includes
the amino acid sequence set forth in SEQ ID NO:6, the amino acid sequence of CDR3 of the VH includes
the amino acid sequence set forth in SEQ ID NO:13, the amino acid sequence of CDR1 of the VL includes
the amino acid sequence set forth in SEQ ID NO:8, the amino acid sequence of CDR2 of the VL includes
the amino acid sequence set forth in SEQ ID NO:9,
and the amino acid sequence of CDR3 of the VL includes
the amino acid sequence set forth in SEQ ID NO:10;

(7) an anti-8-OHdG antibody in which:

the amino acid sequence of CDR1 of the VH includes
the amino acid sequence set forth in SEQ ID NO:11, the amino acid sequence of CDR2 of the VH includes
the amino acid sequence set forth in SEQ ID NO:6, the amino acid sequence of CDR3 of the VH includes
the amino acid sequence set forth in SEQ ID NO:7, the amino acid sequence of CDR1 of the VL includes
the amino acid sequence set forth in SEQ ID NO:69, the amino acid sequence of CDR2 of the VL includes
the amino acid sequence set forth in SEQ ID NO:9,
and the amino acid sequence of CDR3 of the VL includes
the amino acid sequence set forth in SEQ ID NO:10;

(8) an anti-8-OHdG antibody in which:

the amino acid sequence of CDR1 of the VH includes
the amino acid sequence set forth in SEQ ID NO:11, the amino acid sequence of CDR2 of the VH includes
the amino acid sequence set forth in SEQ ID NO:6, the amino acid sequence of CDR3 of the VH includes
the amino acid sequence set forth in SEQ ID NO:70, the amino acid sequence of CDR1 of the VL includes
the amino acid sequence set forth in SEQ ID NO:8, the amino acid sequence of CDR2 of the VL includes
the amino acid sequence set forth in SEQ ID NO:9,
and the amino acid sequence of CDR3 of the VL includes
the amino acid sequence set forth in SEQ ID NO:10;
and (9) an anti-8-OHdG antibody in which:

the amino acid sequence of CDR1 of the VH includes
the amino acid sequence set forth in SEQ ID NO:11, the amino acid sequence of CDR2 of the VH includes
the amino acid sequence set forth in SEQ ID NO:71, the amino acid sequence of CDR3 of the VH includes
the amino acid sequence set forth in SEQ ID NO:7, the amino acid sequence of CDR1 of the VL includes
the amino acid sequence set forth in SEQ ID NO:8, the amino acid sequence of CDR2 of the VL includes
the amino acid sequence set forth in SEQ ID NO:9,
and the amino acid sequence of CDR3 of the VL includes
the amino acid sequence set forth in SEQ ID NO:10.

2. The antibody or the antibody fragment thereof according to claim 1, wherein an amino acid sequence of Framework region
(hereinafter, also referred to as FR) 1 of a VH of the
antibody includes the amino acid sequence set forth in
SEQ ID NO: 20, an amino acid sequence of FR2 of the VH includes the
amino acid sequence set forth in SEQ ID NO:21 or
SEQ ID NO:22, an amino acid sequence of FR3 of the VH includes the
amino acid sequence set forth in SEQ ID NO:23, an amino acid sequence of FR4 of the VH includes the
amino acid sequence set forth in SEQ ID NO:24 or
SEQ ID NO:25, an amino acid sequence of FR1 of a VL of the antibody
includes the amino acid sequence set forth in SEQ ID
NO:26, an amino acid sequence of FR2 of the VL includes an
amino acid sequence set forth in SEQ ID NO:27, an amino acid sequence of FR3 of the VL includes the
amino acid sequence set forth in SEQ ID NO:28 or
SEQ ID NO:29, and an amino acid sequence of FR4 of the VL includes the
amino acid sequence set forth in SEQ ID NO:30.

3. The antibody or the antibody fragment thereof according to claim 2, wherein the amino acid sequence of FR1 of a VH of the
antibody includes the amino acid sequence set forth in
any one of SEQ ID NO:31 to SEQ ID NO:41 and SEQ
ID NO: 72, the amino acid sequence of FR2 of the VH includes the
amino acid sequence set forth in any one of SEQ ID
NO:43 to SEQ ID NO:45, the amino acid sequence of FR3 of the VH includes the
amino acid sequence set forth in any one of SEQ ID
NO:46 to SEQ ID NO:49, the amino acid sequence of FR4 of the VH includes the
amino acid sequence set forth in SEQ ID NO:50 or
SEQ ID NO:51, the amino acid sequence of FR1 of a VL of the antibody
includes the amino acid sequence set forth in any one
of SEQ ID NO:52 to SEQ ID NO:59, the amino acid sequence of FR2 of the VL includes the
amino acid sequence set forth in any one of SEQ ID
NO:60 or SEQ ID NO:61, the amino acid sequence of FR3 of the VL may include
the amino acid sequence set forth in any one of SEQ ID
NO:63 to SEQ ID NO:66, and the amino acid sequence of FR4 of the VL includes the
amino acid sequence set forth in SEQ ID NO:30.

4. The antibody or the antibody fragment thereof according to claim 1, wherein the amino acid sequence of FR1 of a VH of the
antibody includes the amino acid sequence set forth in
any one of SEQ ID NO:31 to SEQ ID NO:41 and SEQ
ID NO: 72, the amino acid sequence of FR2 of the VH includes the
amino acid sequence set forth in any one of SEQ ID
NO:43 to SEQ ID NO:45, the amino acid sequence of FR3 of the VH includes the
amino acid sequence set forth in any one of SEQ ID
NO:46 to SEQ ID NO:49, the amino acid sequence of FR4 of the VH includes the
amino acid sequence set forth in SEQ ID NO:50 or
SEQ ID NO:51, the amino acid sequence of FR1 of a VL of the antibody
includes the amino acid sequence set forth in any one
of SEQ ID NO:52 to SEQ ID NO:59, the amino acid sequence of FR2 of the VL includes the amino acid sequence set forth in any one of SEQ ID NO:60 or SEQ ID NO:61,
the amino acid sequence of FR3 of the VL may include the amino acid sequence set forth in any one of SEQ ID NO:63 to SEQ ID NO:66, and
the amino acid sequence of FR4 of the VL includes the amino acid sequence set forth in SEQ ID NO:30.

5. The antibody or the antibody fragment thereof according to claim 4,
wherein the antibody or the antibody fragment thereof is any one antibody or antibody fragment thereof selected from the group consisting of the following (10) to (26):
(10) an antibody in which:
the amino acid sequence of FR1 of the VH includes the amino acid sequence set forth in SEQ ID NO:31,
the amino acid sequence of FR2 of the VH includes the amino acid sequence set forth in SEQ ID NO:44,
the amino acid sequence of FR3 of the VH includes the amino acid sequence set forth in SEQ ID NO:46,
the amino acid sequence of FR4 of the VH includes the amino acid sequence set forth in SEQ ID NO:50,
the amino acid sequence of FR1 of the VL includes the amino acid sequence set forth in SEQ ID NO:52,
the amino acid sequence of FR2 of the VL includes the amino acid sequence set forth in SEQ ID NO:60,
the amino acid sequence of FR3 of the VL includes the amino acid sequence set forth in SEQ ID NO:63, and
the amino acid sequence of FR4 of the VL includes the amino acid sequence set forth in SEQ ID NO:30;
(11) an antibody in which:
the amino acid sequence of FR1 of the VH includes the amino acid sequence set forth in SEQ ID NO:32,
the amino acid sequence of FR2 of the VH includes the amino acid sequence set forth in SEQ ID NO:44,
the amino acid sequence of FR3 of the VH includes the amino acid sequence set forth in SEQ ID NO:47,
the amino acid sequence of FR4 of the VH includes the amino acid sequence set forth in SEQ ID NO:50,
the amino acid sequence of FR1 of the VL includes the amino acid sequence set forth in SEQ ID NO:53,
the amino acid sequence of FR2 of the VL includes the amino acid sequence set forth in SEQ ID NO:60,
the amino acid sequence of FR3 of the VL includes the amino acid sequence set forth in SEQ ID NO:64, and
the amino acid sequence of FR4 of the VL includes the amino acid sequence set forth in SEQ ID NO:30;
(12) an antibody in which:
the amino acid sequence of FR1 of the VH includes the amino acid sequence set forth in SEQ ID NO:33,
the amino acid sequence of FR2 of the VH includes the amino acid sequence set forth in SEQ ID NO:44,
the amino acid sequence of FR3 of the VH includes the amino acid sequence set forth in SEQ ID NO:47,
the amino acid sequence of FR4 of the VH includes the amino acid sequence set forth in SEQ ID NO:50,
the amino acid sequence of FR1 of the VL includes the amino acid sequence set forth in SEQ ID NO:54,
the amino acid sequence of FR2 of the VL includes the amino acid sequence set forth in SEQ ID NO:60,
the amino acid sequence of FR3 of the VL includes the amino acid sequence set forth in SEQ ID NO:65, and
the amino acid sequence of FR4 of the VL includes the amino acid sequence set forth in SEQ ID NO:30;
(13) an antibody in which:
the amino acid sequence of FR1 of the VH includes the amino acid sequence set forth in SEQ ID NO:34,
the amino acid sequence of FR2 of the VH includes the amino acid sequence set forth in SEQ ID NO:44,
the amino acid sequence of FR3 of the VH includes the amino acid sequence set forth in SEQ ID NO:46,
the amino acid sequence of FR4 of the VH includes the amino acid sequence set forth in SEQ ID NO:51,
the amino acid sequence of FR1 of the VL includes the amino acid sequence set forth in SEQ ID NO:54,
the amino acid sequence of FR2 of the VL includes the amino acid sequence set forth in SEQ ID NO:61,
the amino acid sequence of FR3 of the VL includes the amino acid sequence set forth in SEQ ID NO:64, and
the amino acid sequence of FR4 of the VL includes the amino acid sequence set forth in SEQ ID NO:30;
(14) an antibody in which:
the amino acid sequence of FR1 of the VH includes the amino acid sequence set forth in SEQ ID NO:35,
the amino acid sequence of FR2 of the VH includes the amino acid sequence set forth in SEQ ID NO:43,
the amino acid sequence of FR3 of the VH includes the amino acid sequence set forth in SEQ ID NO:48,
the amino acid sequence of FR4 of the VH includes the amino acid sequence set forth in SEQ ID NO:50,
the amino acid sequence of FR1 of the VL includes the amino acid sequence set forth in SEQ ID NO:55,
the amino acid sequence of FR2 of the VL includes the amino acid sequence set forth in SEQ ID NO:60,
the amino acid sequence of FR3 of the VL includes the amino acid sequence set forth in SEQ ID NO:66, and
the amino acid sequence of FR4 of the VL includes the amino acid sequence set forth in SEQ ID NO:30;
(15) an antibody in which:
the amino acid sequence of FR1 of the VH includes the amino acid sequence set forth in SEQ ID NO:36,
the amino acid sequence of FR2 of the VH includes the amino acid sequence set forth in SEQ ID NO:44,
the amino acid sequence of FR3 of the VH includes the amino acid sequence set forth in SEQ ID NO:47,
the amino acid sequence of FR4 of the VH includes the amino acid sequence set forth in SEQ ID NO:50,
the amino acid sequence of FR1 of the VL includes the amino acid sequence set forth in SEQ ID NO:56,
the amino acid sequence of FR2 of the VL includes the amino acid sequence set forth in SEQ ID NO:60,
the amino acid sequence of FR3 of the VL includes the amino acid sequence set forth in SEQ ID NO:65, and
the amino acid sequence of FR4 of the VL includes the amino acid sequence set forth in SEQ ID NO:30;
(16) an antibody in which:
the amino acid sequence of FR1 of the VH includes the amino acid sequence set forth in SEQ ID NO:37,
the amino acid sequence of FR2 of the VH includes the amino acid sequence set forth in SEQ ID NO:43,
the amino acid sequence of FR3 of the VH includes the amino acid sequence set forth in SEQ ID NO:48,
the amino acid sequence of FR4 of the VH includes the amino acid sequence set forth in SEQ ID NO:50,
the amino acid sequence of FR1 of the VL includes the amino acid sequence set forth in SEQ ID NO:57,
the amino acid sequence of FR2 of the VL includes the amino acid sequence set forth in SEQ ID NO:60,
the amino acid sequence of FR3 of the VL includes the amino acid sequence set forth in SEQ ID NO:66, and
the amino acid sequence of FR4 of the VL includes the amino acid sequence set forth in SEQ ID NO:30;

(17) an antibody in which:
  the amino acid sequence of FR1 of the VH includes the amino acid sequence set forth in SEQ ID NO:38,
  the amino acid sequence of FR2 of the VH includes the amino acid sequence set forth in SEQ ID NO:44,
  the amino acid sequence of FR3 of the VH includes the amino acid sequence set forth in SEQ ID NO:46,
  the amino acid sequence of FR4 of the VH includes the amino acid sequence set forth in SEQ ID NO:50,
  the amino acid sequence of FR1 of the VL includes the amino acid sequence set forth in SEQ ID NO:57,
  the amino acid sequence of FR2 of the VL includes the amino acid sequence set forth in SEQ ID NO:60,
  the amino acid sequence of FR3 of the VL includes the amino acid sequence set forth in SEQ ID NO:65, and
  the amino acid sequence of FR4 of the VL includes the amino acid sequence set forth in SEQ ID NO:30;
(18) an antibody in which:
  the amino acid sequence of FR1 of the VH includes the amino acid sequence set forth in SEQ ID NO:32,
  the amino acid sequence of FR2 of the VH includes the amino acid sequence set forth in SEQ ID NO:44,
  the amino acid sequence of FR3 of the VH includes the amino acid sequence set forth in SEQ ID NO:47,
  the amino acid sequence of FR4 of the VH includes the amino acid sequence set forth in SEQ ID NO:50,
  the amino acid sequence of FR1 of the VL includes the amino acid sequence set forth in SEQ ID NO:55,
  the amino acid sequence of FR2 of the VL includes the amino acid sequence set forth in SEQ ID NO:60,
  the amino acid sequence of FR3 of the VL includes the amino acid sequence set forth in SEQ ID NO:64, and
  the amino acid sequence of FR4 of the VL includes the amino acid sequence set forth in SEQ ID NO:30;
(19) an antibody in which:
  the amino acid sequence of FR1 of the VH includes the amino acid sequence set forth in SEQ ID NO:35,
  the amino acid sequence of FR2 of the VH includes the amino acid sequence set forth in SEQ ID NO:43,
  the amino acid sequence of FR3 of the VH includes the amino acid sequence set forth in SEQ ID NO:48,
  the amino acid sequence of FR4 of the VH includes the amino acid sequence set forth in SEQ ID NO:50,
  the amino acid sequence of FR1 of the VL includes the amino acid sequence set forth in SEQ ID NO:58,
  the amino acid sequence of FR2 of the VL includes the amino acid sequence set forth in SEQ ID NO:60,
  the amino acid sequence of FR3 of the VL includes the amino acid sequence set forth in SEQ ID NO:65, and
  the amino acid sequence of FR4 of the VL includes the amino acid sequence set forth in SEQ ID NO:30;
(20) an antibody in which:
  the amino acid sequence of FR1 of the VH includes the amino acid sequence set forth in SEQ ID NO:33,
  the amino acid sequence of FR2 of the VH includes the amino acid sequence set forth in SEQ ID NO:44,
  the amino acid sequence of FR3 of the VH includes the amino acid sequence set forth in SEQ ID NO:46,
  the amino acid sequence of FR4 of the VH includes the amino acid sequence set forth in SEQ ID NO:50,
  the amino acid sequence of FR1 of the VL includes the amino acid sequence set forth in SEQ ID NO:59,
  the amino acid sequence of FR2 of the VL includes the amino acid sequence set forth in SEQ ID NO:61,
  the amino acid sequence of FR3 of the VL includes the amino acid sequence set forth in SEQ ID NO:64, and
  the amino acid sequence of FR4 of the VL includes the amino acid sequence set forth in SEQ ID NO:30;
(21) an antibody in which:
  the amino acid sequence of FR1 of the VH includes the amino acid sequence set forth in SEQ ID NO:31,
  the amino acid sequence of FR2 of the VH includes the amino acid sequence set forth in SEQ ID NO:44,
  the amino acid sequence of FR3 of the VH includes the amino acid sequence set forth in SEQ ID NO:46,
  the amino acid sequence of FR4 of the VH includes the amino acid sequence set forth in SEQ ID NO:51,
  the amino acid sequence of FR1 of the VL includes the amino acid sequence set forth in SEQ ID NO:54,
  the amino acid sequence of FR2 of the VL includes the amino acid sequence set forth in SEQ ID NO:61,
  the amino acid sequence of FR3 of the VL includes the amino acid sequence set forth in SEQ ID NO:64, and
  the amino acid sequence of FR4 of the VL includes the amino acid sequence set forth in SEQ ID NO:30;
(22) an antibody in which:
  the amino acid sequence of FR1 of the VH includes the amino acid sequence set forth in SEQ ID NO:72,
  the amino acid sequence of FR2 of the VH includes the amino acid sequence set forth in SEQ ID NO:44,
  the amino acid sequence of FR3 of the VH includes the amino acid sequence set forth in SEQ ID NO:46,
  the amino acid sequence of FR4 of the VH includes the amino acid sequence set forth in SEQ ID NO:50,
  the amino acid sequence of FR1 of the VL includes the amino acid sequence set forth in SEQ ID NO:58,
  the amino acid sequence of FR2 of the VL includes the amino acid sequence set forth in SEQ ID NO:60,
  the amino acid sequence of FR3 of the VL includes the amino acid sequence set forth in SEQ ID NO:65, and
  the amino acid sequence of FR4 of the VL includes the amino acid sequence set forth in SEQ ID NO:30;
(23) an antibody in which:
  the amino acid sequence of FR1 of the VH includes the amino acid sequence set forth in SEQ ID NO:32,
  the amino acid sequence of FR2 of the VH includes the amino acid sequence set forth in SEQ ID NO:44,
  the amino acid sequence of FR3 of the VH includes the amino acid sequence set forth in SEQ ID NO:47,
  the amino acid sequence of FR4 of the VH includes the amino acid sequence set forth in SEQ ID NO:50,
  the amino acid sequence of FR1 of the VL includes the amino acid sequence set forth in SEQ ID NO:56,
  the amino acid sequence of FR2 of the VL includes the amino acid sequence set forth in SEQ ID NO:61,
  the amino acid sequence of FR3 of the VL includes the amino acid sequence set forth in SEQ ID NO:64, and
  the amino acid sequence of FR4 of the VL includes the amino acid sequence set forth in SEQ ID NO:30;
(24) an antibody in which:
  the amino acid sequence of FR1 of the VH includes the amino acid sequence set forth in SEQ ID NO:33,
  the amino acid sequence of FR2 of the VH includes the amino acid sequence set forth in SEQ ID NO:44,
  the amino acid sequence of FR3 of the VH includes the amino acid sequence set forth in SEQ ID NO:49,
  the amino acid sequence of FR4 of the VH includes the amino acid sequence set forth in SEQ ID NO:50,
  the amino acid sequence of FR1 of the VL includes the amino acid sequence set forth in SEQ ID NO:58,
  the amino acid sequence of FR2 of the VL includes the amino acid sequence set forth in SEQ ID NO:60, the amino acid sequence of FR3 of the VL includes the amino acid sequence set forth in SEQ ID NO:63, and
the amino acid sequence of FR4 of the VL includes the amino acid sequence set forth in SEQ ID NO:30;
(25) an antibody in which:
the amino acid sequence of FR1 of the VH includes the amino acid sequence set forth in SEQ ID NO:39,
the amino acid sequence of FR2 of the VH includes the amino acid sequence set forth in SEQ ID NO:43,
the amino acid sequence of FR3 of the VH includes the amino acid sequence set forth in SEQ ID NO:48,
the amino acid sequence of FR4 of the VH includes the amino acid sequence set forth in SEQ ID NO:50,
the amino acid sequence of FR1 of the VL includes the amino acid sequence set forth in SEQ ID NO:58,
the amino acid sequence of FR2 of the VL includes the amino acid sequence set forth in SEQ ID NO:60,
the amino acid sequence of FR3 of the VL includes the amino acid sequence set forth in SEQ ID NO:64, and
the amino acid sequence of FR4 of the VL includes the amino acid sequence set forth in SEQ ID NO:30; and
(26) an antibody in which:
the amino acid sequence of FR1 of the VH includes the amino acid sequence set forth in SEQ ID NO:31,
the amino acid sequence of FR2 of the VH includes the amino acid sequence set forth in SEQ ID NO:44,
the amino acid sequence of FR3 of the VH includes the amino acid sequence set forth in SEQ ID NO:46,
the amino acid sequence of FR4 of the VH includes the amino acid sequence set forth in SEQ ID NO:51,
the amino acid sequence of FR1 of the VL includes the amino acid sequence set forth in SEQ ID NO:57,
the amino acid sequence of FR2 of the VL includes the amino acid sequence set forth in SEQ ID NO:60,
the amino acid sequence of FR3 of the VL includes the amino acid sequence set forth in SEQ ID NO:64, and
the amino acid sequence of FR4 of the VL includes the amino acid sequence set forth in SEQ ID NO:30.

6. The antibody or the antibody fragment thereof according to claim 1,
wherein the antibody is any one antibody selected from the group consisting of the following (27) to (43):
(27) an antibody in which:
the amino acid sequence of CDR1 of the VH includes the amino acid sequence set forth in SEQ ID NO:5,
the amino acid sequence of CDR2 of the VH includes the amino acid sequence set forth in SEQ ID NO:6,
the amino acid sequence of CDR3 of the VH includes the amino acid sequence set forth in SEQ ID NO:7,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;
the amino acid sequence of FR1 of the VH includes the amino acid sequence set forth in SEQ ID NO:31,
the amino acid sequence of FR2 of the VH includes the amino acid sequence set forth in SEQ ID NO:44,
the amino acid sequence of FR3 of the VH includes the amino acid sequence set forth in SEQ ID NO:46,
the amino acid sequence of FR4 of the VH includes the amino acid sequence set forth in SEQ ID NO:50,
the amino acid sequence of FR1 of the VL includes the amino acid sequence set forth in SEQ ID NO:52,
the amino acid sequence of FR2 of the VL includes the amino acid sequence set forth in SEQ ID NO:60,
the amino acid sequence of FR3 of the VL includes the amino acid sequence set forth in SEQ ID NO:63, and
the amino acid sequence of FR4 of the VL includes the amino acid sequence set forth in SEQ ID NO:30;
(28) an antibody in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes the amino acid sequence set forth in SEQ ID NO:7,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;
the amino acid sequence of FR1 of the VH includes the amino acid sequence set forth in SEQ ID NO:32,
the amino acid sequence of FR2 of the VH includes the amino acid sequence set forth in SEQ ID NO:44,
the amino acid sequence of FR3 of the VH includes the amino acid sequence set forth in SEQ ID NO:47,
the amino acid sequence of FR4 of the VH includes the amino acid sequence set forth in SEQ ID NO:50,
the amino acid sequence of FR1 of the VL includes the amino acid sequence set forth in SEQ ID NO:53,
the amino acid sequence of FR2 of the VL includes the amino acid sequence set forth in SEQ ID NO:60,
the amino acid sequence of FR3 of the VL includes the amino acid sequence set forth in SEQ ID NO:64, and
the amino acid sequence of FR4 of the VL includes the amino acid sequence set forth in SEQ ID NO:30;
(29) an antibody in which:
the amino acid sequence of CDR1 of the VH includes the amino acid sequence set forth in SEQ ID NO:11,
the amino acid sequence of CDR2 of the VH includes the amino acid sequence set forth in SEQ ID NO:12,
the amino acid sequence of CDR3 of the VH includes the amino acid sequence set forth in SEQ ID NO:7,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;
the amino acid sequence of FR1 of the VH includes the amino acid sequence set forth in SEQ ID NO:33,
the amino acid sequence of FR2 of the VH includes the amino acid sequence set forth in SEQ ID NO:44,
the amino acid sequence of FR3 of the VH includes the amino acid sequence set forth in SEQ ID NO:47,
the amino acid sequence of FR4 of the VH includes the amino acid sequence set forth in SEQ ID NO:50,
the amino acid sequence of FR1 of the VL includes the amino acid sequence set forth in SEQ ID NO:54,
the amino acid sequence of FR2 of the VL includes the amino acid sequence set forth in SEQ ID NO:60,
the amino acid sequence of FR3 of the VL includes the amino acid sequence set forth in SEQ ID NO:65, and
the amino acid sequence of FR4 of the VL includes the amino acid sequence set forth in SEQ ID NO:30;

(30) an antibody in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes the amino acid sequence set forth in SEQ ID NO:7,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;
the amino acid sequence of FR1 of the VH includes the amino acid sequence set forth in SEQ ID NO:34,
the amino acid sequence of FR2 of the VH includes the amino acid sequence set forth in SEQ ID NO:44,
the amino acid sequence of FR3 of the VH includes the amino acid sequence set forth in SEQ ID NO:46,
the amino acid sequence of FR4 of the VH includes the amino acid sequence set forth in SEQ ID NO:51,
the amino acid sequence of FR1 of the VL includes the amino acid sequence set forth in SEQ ID NO:54,
the amino acid sequence of FR2 of the VL includes the amino acid sequence set forth in SEQ ID NO:61,
the amino acid sequence of FR3 of the VL includes the amino acid sequence set forth in SEQ ID NO:64, and
the amino acid sequence of FR4 of the VL includes the amino acid sequence set forth in SEQ ID NO:30;

(31) an antibody in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes the amino acid sequence set forth in SEQ ID NO:13,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:14;
the amino acid sequence of FR1 of the VH includes the amino acid sequence set forth in SEQ ID NO:35,
the amino acid sequence of FR2 of the VH includes the amino acid sequence set forth in SEQ ID NO:43,
the amino acid sequence of FR3 of the VH includes the amino acid sequence set forth in SEQ ID NO:48,
the amino acid sequence of FR4 of the VH includes the amino acid sequence set forth in SEQ ID NO:50,
the amino acid sequence of FR1 of the VL includes the amino acid sequence set forth in SEQ ID NO:55,
the amino acid sequence of FR2 of the VL includes the amino acid sequence set forth in SEQ ID NO:60,
the amino acid sequence of FR3 of the VL includes the amino acid sequence set forth in SEQ ID NO:66, and
the amino acid sequence of FR4 of the VL includes the amino acid sequence set forth in SEQ ID NO:30;

(32) an antibody in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes the amino acid sequence set forth in SEQ ID NO:7,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;
the amino acid sequence of FR1 of the VH includes the amino acid sequence set forth in SEQ ID NO:36,
the amino acid sequence of FR2 of the VH includes the amino acid sequence set forth in SEQ ID NO:44,
the amino acid sequence of FR3 of the VH includes the amino acid sequence set forth in SEQ ID NO:47,
the amino acid sequence of FR4 of the VH includes the amino acid sequence set forth in SEQ ID NO:50,
the amino acid sequence of FR1 of the VL includes the amino acid sequence set forth in SEQ ID NO:56,
the amino acid sequence of FR2 of the VL includes the amino acid sequence set forth in SEQ ID NO:60,
the amino acid sequence of FR3 of the VL includes the amino acid sequence set forth in SEQ ID NO:65, and
the amino acid sequence of FR4 of the VL includes the amino acid sequence set forth in SEQ ID NO:30;

(33) an antibody in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes the amino acid sequence set forth in SEQ ID NO:13,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:15;
the amino acid sequence of FR1 of the VH includes the amino acid sequence set forth in SEQ ID NO:37,
the amino acid sequence of FR2 of the VH includes the amino acid sequence set forth in SEQ ID NO:43,
the amino acid sequence of FR3 of the VH includes the amino acid sequence set forth in SEQ ID NO:48,
the amino acid sequence of FR4 of the VH includes the amino acid sequence set forth in SEQ ID NO:50,
the amino acid sequence of FR1 of the VL includes the amino acid sequence set forth in SEQ ID NO:57,
the amino acid sequence of FR2 of the VL includes the amino acid sequence set forth in SEQ ID NO:60,
the amino acid sequence of FR3 of the VL includes the amino acid sequence set forth in SEQ ID NO:66, and
the amino acid sequence of FR4 of the VL includes the amino acid sequence set forth in SEQ ID NO:30;

(34) an antibody in which:
the amino acid sequence of CDR1 of the VH includes the amino acid sequence set forth in SEQ ID NO:11,
the amino acid sequence of CDR2 of the VH includes the amino acid sequence set forth in SEQ ID NO:6,
the amino acid sequence of CDR3 of the VH includes the amino acid sequence set forth in SEQ ID NO:7,
the amino acid sequence of CDR1 of the VL includes the amino acid sequence set forth in SEQ ID NO:8,
the amino acid sequence of CDR2 of the VL includes the amino acid sequence set forth in SEQ ID NO:9, and
the amino acid sequence of CDR3 of the VL includes the amino acid sequence set forth in SEQ ID NO:10;

the amino acid sequence of FR1 of the VH includes the
amino acid sequence set forth in SEQ ID NO:38,
the amino acid sequence of FR2 of the VH includes the
amino acid sequence set forth in SEQ ID NO:44,
the amino acid sequence of FR3 of the VH includes the
amino acid sequence set forth in SEQ ID NO:46,
the amino acid sequence of FR4 of the VH includes the
amino acid sequence set forth in SEQ ID NO:50,
the amino acid sequence of FR1 of the VL includes the
amino acid sequence set forth in SEQ ID NO:57,
the amino acid sequence of FR2 of the VL includes the
amino acid sequence set forth in SEQ ID NO:60,
the amino acid sequence of FR3 of the VL includes the
amino acid sequence set forth in SEQ ID NO:65, and
the amino acid sequence of FR4 of the VL includes the
amino acid sequence set forth in SEQ ID NO:30;
(35) an antibody in which:
the amino acid sequence of CDR1 of the VH includes
the amino acid sequence set forth in SEQ ID NO:11,
the amino acid sequence of CDR2 of the VH includes
the amino acid sequence set forth in SEQ ID NO:6,
the amino acid sequence of CDR3 of the VH includes
the amino acid sequence set forth in SEQ ID NO:7,
the amino acid sequence of CDR1 of the VL includes
the amino acid sequence set forth in SEQ ID NO:8,
the amino acid sequence of CDR2 of the VL includes
the amino acid sequence set forth in SEQ ID NO:9,
and
the amino acid sequence of CDR3 of the VL includes
the amino acid sequence set forth in SEQ ID NO:10;
the amino acid sequence of FR1 of the VH includes the
amino acid sequence set forth in SEQ ID NO:32,
the amino acid sequence of FR2 of the VH includes the
amino acid sequence set forth in SEQ ID NO:44,
the amino acid sequence of FR3 of the VH includes the
amino acid sequence set forth in SEQ ID NO:47,
the amino acid sequence of FR4 of the VH includes the
amino acid sequence set forth in SEQ ID NO:50,
the amino acid sequence of FR1 of the VL includes the
amino acid sequence set forth in SEQ ID NO:55,
the amino acid sequence of FR2 of the VL includes the
amino acid sequence set forth in SEQ ID NO:60,
the amino acid sequence of FR3 of the VL includes the
amino acid sequence set forth in SEQ ID NO:64, and
the amino acid sequence of FR4 of the VL includes the
amino acid sequence set forth in SEQ ID NO:30;
(36) an antibody in which:
the amino acid sequence of CDR1 of the VH includes
the amino acid sequence set forth in SEQ ID NO:11,
the amino acid sequence of CDR2 of the VH includes
the amino acid sequence set forth in SEQ ID NO:6,
the amino acid sequence of CDR3 of the VH includes
the amino acid sequence set forth in SEQ ID NO:7,
the amino acid sequence of CDR1 of the VL includes
the amino acid sequence set forth in SEQ ID NO:8,
the amino acid sequence of CDR2 of the VL includes
the amino acid sequence set forth in SEQ ID NO:9,
and
the amino acid sequence of CDR3 of the VL includes
the amino acid sequence set forth in SEQ ID NO:10;
the amino acid sequence of FR1 of the VH includes the
amino acid sequence set forth in SEQ ID NO:31,
the amino acid sequence of FR2 of the VH includes the
amino acid sequence set forth in SEQ ID NO:44,
the amino acid sequence of FR3 of the VH includes the
amino acid sequence set forth in SEQ ID NO:46,
the amino acid sequence of FR4 of the VH includes the
amino acid sequence set forth in SEQ ID NO:51,
the amino acid sequence of FR1 of the VL includes the
amino acid sequence set forth in SEQ ID NO:54,
the amino acid sequence of FR2 of the VL includes the
amino acid sequence set forth in SEQ ID NO:61,
the amino acid sequence of FR3 of the VL includes the
amino acid sequence set forth in SEQ ID NO:64, and
the amino acid sequence of FR4 of the VL includes the
amino acid sequence set forth in SEQ ID NO:30;
(37) an antibody in which:
the amino acid sequence of CDR1 of the VH includes
the amino acid sequence set forth in SEQ ID NO:11,
the amino acid sequence of CDR2 of the VH includes
the amino acid sequence set forth in SEQ ID NO:6,
the amino acid sequence of CDR3 of the VH includes
the amino acid sequence set forth in SEQ ID NO:7,
the amino acid sequence of CDR1 of the VL includes
the amino acid sequence set forth in SEQ ID NO:69,
the amino acid sequence of CDR2 of the VL includes
the amino acid sequence set forth in SEQ ID NO:9,
and
the amino acid sequence of CDR3 of the VL includes
the amino acid sequence set forth in SEQ ID NO:10;
the amino acid sequence of FR1 of the VH includes the
amino acid sequence set forth in SEQ ID NO:72,
the amino acid sequence of FR2 of the VH includes the
amino acid sequence set forth in SEQ ID NO:44,
the amino acid sequence of FR3 of the VH includes the
amino acid sequence set forth in SEQ ID NO:46,
the amino acid sequence of FR4 of the VH includes the
amino acid sequence set forth in SEQ ID NO:50,
the amino acid sequence of FR1 of the VL includes the
amino acid sequence set forth in SEQ ID NO:58,
the amino acid sequence of FR2 of the VL includes the
amino acid sequence set forth in SEQ ID NO:60,
the amino acid sequence of FR3 of the VL includes the
amino acid sequence set forth in SEQ ID NO:65, and
the amino acid sequence of FR4 of the VL includes the
amino acid sequence set forth in SEQ ID NO:30;
(38) an antibody in which:
the amino acid sequence of CDR1 of the VH includes
the amino acid sequence set forth in SEQ ID NO:11,
the amino acid sequence of CDR2 of the VH includes
the amino acid sequence set forth in SEQ ID NO:6,
the amino acid sequence of CDR3 of the VH includes
the amino acid sequence set forth in SEQ ID NO:13,
the amino acid sequence of CDR1 of the VL includes
the amino acid sequence set forth in SEQ ID NO:8,
the amino acid sequence of CDR2 of the VL includes
the amino acid sequence set forth in SEQ ID NO:9,
and
the amino acid sequence of CDR3 of the VL includes
the amino acid sequence set forth in SEQ ID NO:10;
the amino acid sequence of FR1 of the VH includes the
amino acid sequence set forth in SEQ ID NO:35,
the amino acid sequence of FR2 of the VH includes the
amino acid sequence set forth in SEQ ID NO:43,
the amino acid sequence of FR3 of the VH includes the
amino acid sequence set forth in SEQ ID NO:48,
the amino acid sequence of FR4 of the VH includes the
amino acid sequence set forth in SEQ ID NO:50,
the amino acid sequence of FR1 of the VL includes the
amino acid sequence set forth in SEQ ID NO:58,
the amino acid sequence of FR2 of the VL includes the
amino acid sequence set forth in SEQ ID NO:60, the amino acid sequence of FR3 of the VL includes the
   amino acid sequence set forth in SEQ ID NO:65, and
the amino acid sequence of FR4 of the VL includes the
   amino acid sequence set forth in SEQ ID NO:30;
(39) an antibody in which:
the amino acid sequence of CDR1 of the VH includes
   the amino acid sequence set forth in SEQ ID NO:11,
the amino acid sequence of CDR2 of the VH includes
   the amino acid sequence set forth in SEQ ID NO:6,
the amino acid sequence of CDR3 of the VH includes
   the amino acid sequence set forth in SEQ ID NO:7,
the amino acid sequence of CDR1 of the VL includes
   the amino acid sequence set forth in SEQ ID NO:8,
the amino acid sequence of CDR2 of the VL includes
   the amino acid sequence set forth in SEQ ID NO:9,
   and
the amino acid sequence of CDR3 of the VL includes
   the amino acid sequence set forth in SEQ ID NO:10;
the amino acid sequence of FR1 of the VH includes the
   amino acid sequence set forth in SEQ ID NO:33,
the amino acid sequence of FR2 of the VH includes the
   amino acid sequence set forth in SEQ ID NO:44,
the amino acid sequence of FR3 of the VH includes the
   amino acid sequence set forth in SEQ ID NO:46,
the amino acid sequence of FR4 of the VH includes the
   amino acid sequence set forth in SEQ ID NO:50,
the amino acid sequence of FR1 of the VL includes the
   amino acid sequence set forth in SEQ ID NO:59,
the amino acid sequence of FR2 of the VL includes the
   amino acid sequence set forth in SEQ ID NO:61,
the amino acid sequence of FR3 of the VL includes the
   amino acid sequence set forth in SEQ ID NO:64, and
the amino acid sequence of FR4 of the VL includes the
   amino acid sequence set forth in SEQ ID NO:30;
(40) an antibody in which:
the amino acid sequence of CDR1 of the VH includes
   the amino acid sequence set forth in SEQ ID NO:11,
the amino acid sequence of CDR2 of the VH includes
   the amino acid sequence set forth in SEQ ID NO:6,
the amino acid sequence of CDR3 of the VH includes
   the amino acid sequence set forth in SEQ ID NO:70,
the amino acid sequence of CDR1 of the VL includes
   the amino acid sequence set forth in SEQ ID NO:8,
the amino acid sequence of CDR2 of the VL includes
   the amino acid sequence set forth in SEQ ID NO:9,
   and
the amino acid sequence of CDR3 of the VL includes
   the amino acid sequence set forth in SEQ ID NO:10;
the amino acid sequence of FR1 of the VH includes the
   amino acid sequence set forth in SEQ ID NO:32,
the amino acid sequence of FR2 of the VH includes the
   amino acid sequence set forth in SEQ ID NO:44,
the amino acid sequence of FR3 of the VH includes the
   amino acid sequence set forth in SEQ ID NO:47,
the amino acid sequence of FR4 of the VH includes the
   amino acid sequence set forth in SEQ ID NO:50,
the amino acid sequence of FR1 of the VL includes the
   amino acid sequence set forth in SEQ ID NO:56,
the amino acid sequence of FR2 of the VL includes the
   amino acid sequence set forth in SEQ ID NO:61,
the amino acid sequence of FR3 of the VL includes the
   amino acid sequence set forth in SEQ ID NO:64, and
the amino acid sequence of FR4 of the VL includes the
   amino acid sequence set forth in SEQ ID NO:30;
(41) an antibody in which:
the amino acid sequence of CDR1 of the VH includes
   the amino acid sequence set forth in SEQ ID NO:11,
the amino acid sequence of CDR2 of the VH includes
   the amino acid sequence set forth in SEQ ID NO:71,
the amino acid sequence of CDR3 of the VH includes
   the amino acid sequence set forth in SEQ ID NO:7,
the amino acid sequence of CDR1 of the VL includes
   the amino acid sequence set forth in SEQ ID NO:8,
the amino acid sequence of CDR2 of the VL includes
   the amino acid sequence set forth in SEQ ID NO:9,
   and
the amino acid sequence of CDR3 of the VL includes
   the amino acid sequence set forth in SEQ ID NO:10;
the amino acid sequence of FR1 of the VH includes the
   amino acid sequence set forth in SEQ ID NO:33,
the amino acid sequence of FR2 of the VH includes the
   amino acid sequence set forth in SEQ ID NO:44,
the amino acid sequence of FR3 of the VH includes the
   amino acid sequence set forth in SEQ ID NO:49,
the amino acid sequence of FR4 of the VH includes the
   amino acid sequence set forth in SEQ ID NO:50,
the amino acid sequence of FR1 of the VL includes the
   amino acid sequence set forth in SEQ ID NO:58,
the amino acid sequence of FR2 of the VL includes the
   amino acid sequence set forth in SEQ ID NO:60,
the amino acid sequence of FR3 of the VL includes the
   amino acid sequence set forth in SEQ ID NO:63, and
the amino acid sequence of FR4 of the VL includes the
   amino acid sequence set forth in SEQ ID NO:30;
(42) an antibody in which:
the amino acid sequence of CDR1 of the VH includes
   the amino acid sequence set forth in SEQ ID NO:11,
the amino acid sequence of CDR2 of the VH includes
   the amino acid sequence set forth in SEQ ID NO:6,
the amino acid sequence of CDR3 of the VH includes
   the amino acid sequence set forth in SEQ ID NO:13,
the amino acid sequence of CDR1 of the VL includes
   the amino acid sequence set forth in SEQ ID NO:8,
the amino acid sequence of CDR2 of the VL includes
   the amino acid sequence set forth in SEQ ID NO:9,
   and
the amino acid sequence of CDR3 of the VL includes
   the amino acid sequence set forth in SEQ ID NO:10;
the amino acid sequence of FR1 of the VH includes the
   amino acid sequence set forth in SEQ ID NO:39,
the amino acid sequence of FR2 of the VH includes the
   amino acid sequence set forth in SEQ ID NO:43,
the amino acid sequence of FR3 of the VH includes the
   amino acid sequence set forth in SEQ ID NO:48,
the amino acid sequence of FR4 of the VH includes the
   amino acid sequence set forth in SEQ ID NO:50,
the amino acid sequence of FR1 of the VL includes the
   amino acid sequence set forth in SEQ ID NO:58,
the amino acid sequence of FR2 of the VL includes the
   amino acid sequence set forth in SEQ ID NO:60,
the amino acid sequence of FR3 of the VL includes the
   amino acid sequence set forth in SEQ ID NO:64, and
the amino acid sequence of FR4 of the VL includes the
   amino acid sequence set forth in SEQ ID NO:30; and
(43) an antibody in which:
the amino acid sequence of CDR1 of the VH includes
   the amino acid sequence set forth in SEQ ID NO:11,
the amino acid sequence of CDR2 of the VH includes
   the amino acid sequence set forth in SEQ ID NO:6,
the amino acid sequence of CDR3 of the VH includes
   the amino acid sequence set forth in SEQ ID NO:7,
the amino acid sequence of CDR1 of the VL includes
   the amino acid sequence set forth in SEQ ID NO:8, the amino acid sequence of CDR2 of the VL includes the amino acid sequence set forth in SEQ ID NO:9, and the amino acid sequence of CDR3 of the VL includes the amino acid sequence set forth in SEQ ID NO:10;

the amino acid sequence of FR1 of the VH includes the amino acid sequence set forth in SEQ ID NO:31, the amino acid sequence of FR2 of the VH includes the amino acid sequence set forth in SEQ ID NO:44, the amino acid sequence of FR3 of the VH includes the amino acid sequence set forth in SEQ ID NO:46, the amino acid sequence of FR4 of the VH includes the amino acid sequence set forth in SEQ ID NO:51, the amino acid sequence of FR1 of the VL includes the amino acid sequence set forth in SEQ ID NO:57, the amino acid sequence of FR2 of the VL includes the amino acid sequence set forth in SEQ ID NO:60, the amino acid sequence of FR3 of the VL includes the amino acid sequence set forth in SEQ ID NO:64, and the amino acid sequence of FR4 of the VL includes the amino acid sequence set forth in SEQ ID NO:30.

7. The antibody or the antibody fragment thereof according to claim 1, wherein the antibody is derived from rabbit.

8. A nucleic acid encoding the antibody or the antibody fragment thereof according to claim 1.

9. A vector comprising the nucleic acid according to claim 8.

10. The vector according to claim 9, wherein the vector is an expression vector derived from mammal.

11. An antibody-producing cell obtained by introducing the vector according to claim 9 into a host cell.

12. The antibody-producing cell according to claim 11, wherein the host cell is a HEK293 cell or a CHO cell.

13. An antibody-producing cell obtained by introducing the vector according to claim 9 into a host cell.

14. A method for producing the antibody or the antibody fragment thereof according to claim 1, the method comprising:

culturing an antibody-producing cell obtained by introducing a vector comprising a nucleic acid encoding the antibody or the antibody fragment thereof according to claim 1, wherein the vector is an expression vector derived from mammal, into a host cell to produce and accumulate the antibody or the antibody fragment thereof according to claim 1 in a culture; and collecting the antibody or the antibody fragment thereof from the culture.

15. An immunological measuring method of 8-hydroxy-2'-deoxyguanosine in a specimen, the method comprising:

reacting the antibody or antibody fragment thereof according to claim 1 with 8-hydroxy-2'-deoxyguanosine in a specimen; and measuring the 8-hydroxy-2'-deoxyguanosine by an immunological measuring method utilizing an antigen-antibody reaction, wherein the immunological measuring method is one of ELISA, immunochromatography, chemiluminescence-enzyme immunoassay, chemiluminescence immunoassay, electrochemiluminescence immunoassay, enzyme immunoassay, a fluorescence antibody method, fluorescence enzyme immunoassay, fluorescence polarization immunoassay, a metal particle-labeled antibody electrochemical measurement method, and a latex coagulating method.

16. The measuring method according to claim 15, wherein the specimen is urine.

17. A kit for measuring 8-hydroxy-2'-deoxyguanosine in a specimen, the kit comprising the antibody or the antibody fragment thereof according to claim 1.

18. The kit according to claim 17, wherein the specimen is urine.

19. A device for measuring 8-hydroxy-2'-deoxyguanosine in a specimen, the device comprising the antibody or the antibody fragment thereof according to claim 1.

20. The device according to claim 19, wherein the specimen is urine.

\* \* \* \* \*

```
SEQUENCE LISTING

<160> NUMBER OF SEQ ID NOS: 72

<210> SEQ ID NO 1
<211> LENGTH: 5
<212> TYPE: PRT
<213> ORGANISM: Oryctolagus cuniculus

<400> SEQUENCE: 1

Ile Asn Glu Trp Gly
1               5

<210> SEQ ID NO 2
<211> LENGTH: 8
<212> TYPE: PRT
<213> ORGANISM: Oryctolagus cuniculus

<400> SEQUENCE: 2

Trp Gly Ser Arg Val Phe Asn Ile
1               5

<210> SEQ ID NO 3
<211> LENGTH: 4
<212> TYPE: PRT
<213> ORGANISM: Oryctolagus cuniculus

<400> SEQUENCE: 3
```

```
Gln Ser Val Tyr
1

<210> SEQ ID NO 4
<211> LENGTH: 7
<212> TYPE: PRT
<213> ORGANISM: Oryctolagus cuniculus

<400> SEQUENCE: 4

Leu Gly Ser Tyr Asp Ala Arg
1               5

<210> SEQ ID NO 5
<211> LENGTH: 8
<212> TYPE: PRT
<213> ORGANISM: Oryctolagus cuniculus

<400> SEQUENCE: 5

Gly Phe Ser Pro Ser Thr Tyr Gly
1               5

<210> SEQ ID NO 6
<211> LENGTH: 7
<212> TYPE: PRT
<213> ORGANISM: Oryctolagus cuniculus

<400> SEQUENCE: 6

Ile Asn Glu Trp Gly Asn Ile
1               5

<210> SEQ ID NO 7
<211> LENGTH: 12
<212> TYPE: PRT
<213> ORGANISM: Oryctolagus cuniculus

<400> SEQUENCE: 7

Ala Ser Glu Val Trp Gly Ser Arg Val Phe Asn Ile
1               5                   10

<210> SEQ ID NO 8
<211> LENGTH: 8
<212> TYPE: PRT
<213> ORGANISM: Oryctolagus cuniculus

<400> SEQUENCE: 8

Gln Ser Val Tyr Ser Lys Asn Tyr
1               5

<210> SEQ ID NO 9
<211> LENGTH: 3
<212> TYPE: PRT
<213> ORGANISM: Oryctolagus cuniculus

<400> SEQUENCE: 9

Arg Ala Ser
1

<210> SEQ ID NO 10
<211> LENGTH: 13
<212> TYPE: PRT
<213> ORGANISM: Oryctolagus cuniculus

<400> SEQUENCE: 10

Leu Gly Ser Tyr Asp Ala Arg Ser Gly Asp Ser Asn Val
```

```
<210> SEQ ID NO 11
<211> LENGTH: 8
<212> TYPE: PRT
<213> ORGANISM: Oryctolagus cuniculus

<400> SEQUENCE: 11

Gly Phe Ser Leu Ser Thr Tyr Gly
1               5

<210> SEQ ID NO 12
<211> LENGTH: 7
<212> TYPE: PRT
<213> ORGANISM: Oryctolagus cuniculus

<400> SEQUENCE: 12

Ile Asn Glu Trp Gly Asn Val
1               5

<210> SEQ ID NO 13
<211> LENGTH: 12
<212> TYPE: PRT
<213> ORGANISM: Oryctolagus cuniculus

<400> SEQUENCE: 13

Ala Ser Glu Ile Trp Gly Ser Arg Val Phe Asn Ile
1               5                   10

<210> SEQ ID NO 14
<211> LENGTH: 13
<212> TYPE: PRT
<213> ORGANISM: Oryctolagus cuniculus

<400> SEQUENCE: 14

Leu Gly Ser Tyr Asp Ala Arg Tyr Gly Asp Ser Asn Val
1               5                   10

<210> SEQ ID NO 15
<211> LENGTH: 13
<212> TYPE: PRT
<213> ORGANISM: Oryctolagus cuniculus

<400> SEQUENCE: 15

Leu Gly Ser Tyr Asp Ala Arg Tyr Ser Asp Ser Asn Val
1               5                   10

<210> SEQ ID NO 16
<211> LENGTH: 7
<212> TYPE: PRT
<213> ORGANISM: Oryctolagus cuniculus

<400> SEQUENCE: 16

Ile Asn Glu Trp Gly His Ile
1               5

<210> SEQ ID NO 17
<211> LENGTH: 8
<212> TYPE: PRT
<213> ORGANISM: Oryctolagus cuniculus

<400> SEQUENCE: 17

Gly Phe Ser Leu Met Thr Tyr Gly
1               5
```

```
<210> SEQ ID NO 18
<211> LENGTH: 8
<212> TYPE: PRT
<213> ORGANISM: Oryctolagus cuniculus

<400> SEQUENCE: 18

Gln Ser Val Tyr Asn Lys Asn Tyr
1               5

<210> SEQ ID NO 19
<211> LENGTH: 7
<212> TYPE: PRT
<213> ORGANISM: Oryctolagus cuniculus

<400> SEQUENCE: 19

Ile Asn Glu Trp Gly Phe Ile
1               5

<210> SEQ ID NO 20
<211> LENGTH: 8
<212> TYPE: PRT
<213> ORGANISM: Oryctolagus cuniculus

<400> SEQUENCE: 20

Leu Thr Leu Thr Cys Thr Val Ser
1               5

<210> SEQ ID NO 21
<211> LENGTH: 9
<212> TYPE: PRT
<213> ORGANISM: Oryctolagus cuniculus

<400> SEQUENCE: 21

Val Ser Trp Val Arg Gln Ala Pro Gly
1               5

<210> SEQ ID NO 22
<211> LENGTH: 7
<212> TYPE: PRT
<213> ORGANISM: Oryctolagus cuniculus

<400> SEQUENCE: 22

Gly Leu Asp Trp Ile Gly Asn
1               5

<210> SEQ ID NO 23
<211> LENGTH: 20
<212> TYPE: PRT
<213> ORGANISM: Oryctolagus cuniculus

<400> SEQUENCE: 23

Asn Thr Val Thr Leu Lys Met Thr Ser Leu Thr Ala Ala Asp Thr Ala
1               5                   10                  15

Thr Tyr Phe Cys
            20

<210> SEQ ID NO 24
<211> LENGTH: 5
<212> TYPE: PRT
<213> ORGANISM: Oryctolagus cuniculus

<400> SEQUENCE: 24

Trp Gly Pro Gly Thr
1               5
```

<210> SEQ ID NO 25
<211> LENGTH: 5
<212> TYPE: PRT
<213> ORGANISM: Oryctolagus cuniculus

<400> SEQUENCE: 25

Val Thr Val Ser Ser
1               5

<210> SEQ ID NO 26
<211> LENGTH: 22
<212> TYPE: PRT
<213> ORGANISM: Oryctolagus cuniculus

<400> SEQUENCE: 26

Thr Gln Thr Pro Ser Ser Val Ser Ala Ala Val Gly Gly Thr Val Thr
1               5                   10                  15

Ile Asn Cys Gln Ala Ser
            20

<210> SEQ ID NO 27
<211> LENGTH: 12
<212> TYPE: PRT
<213> ORGANISM: Oryctolagus cuniculus

<400> SEQUENCE: 27

Leu Ser Trp Phe Gln Gln Lys Pro Gly Gln Pro Pro
1               5                   10

<210> SEQ ID NO 28
<211> LENGTH: 16
<212> TYPE: PRT
<213> ORGANISM: Oryctolagus cuniculus

<400> SEQUENCE: 28

Asn Leu Ala Ser Gly Val Pro Ser Arg Phe Ser Gly Ser Gly Ser Gly
1               5                   10                  15

<210> SEQ ID NO 29
<211> LENGTH: 10
<212> TYPE: PRT
<213> ORGANISM: Oryctolagus cuniculus

<400> SEQUENCE: 29

Gln Cys Asp Asp Ala Ala Thr Tyr Tyr Cys
1               5                   10

<210> SEQ ID NO 30
<211> LENGTH: 10
<212> TYPE: PRT
<213> ORGANISM: Oryctolagus cuniculus

<400> SEQUENCE: 30

Phe Gly Gly Gly Thr Glu Val Val Val Lys
1               5                   10

<210> SEQ ID NO 31
<211> LENGTH: 24
<212> TYPE: PRT
<213> ORGANISM: Oryctolagus cuniculus

<400> SEQUENCE: 31

Gln Ser Val Lys Glu Ser Gly Gly Gly Leu Phe Lys Pro Thr Asp Thr

```
1               5                   10                  15

Leu Thr Leu Thr Cys Thr Val Ser
            20

<210> SEQ ID NO 32
<211> LENGTH: 24
<212> TYPE: PRT
<213> ORGANISM: Oryctolagus cuniculus

<400> SEQUENCE: 32

Gln Ser Val Glu Glu Ser Gly Gly Gly Leu Phe Lys Pro Thr Asp Thr
1               5                   10                  15

Leu Thr Leu Thr Cys Thr Val Ser
            20

<210> SEQ ID NO 33
<211> LENGTH: 24
<212> TYPE: PRT
<213> ORGANISM: Oryctolagus cuniculus

<400> SEQUENCE: 33

Gln Thr Val Lys Glu Ser Gly Gly Gly Leu Phe Lys Pro Thr Asp Thr
1               5                   10                  15

Leu Thr Leu Thr Cys Thr Val Ser
            20

<210> SEQ ID NO 34
<211> LENGTH: 24
<212> TYPE: PRT
<213> ORGANISM: Oryctolagus cuniculus

<400> SEQUENCE: 34

Gln Ser Val Lys Glu Ser Gly Gly Gly Leu Phe Lys Pro Thr Asp Thr
1               5                   10                  15

Leu Thr Leu Thr Cys Thr Val Ser
            20

<210> SEQ ID NO 35
<211> LENGTH: 24
<212> TYPE: PRT
<213> ORGANISM: Oryctolagus cuniculus

<400> SEQUENCE: 35

Gln Ser Val Lys Glu Ser Gly Gly Gly Leu Phe Lys Pro Ala Asp Thr
1               5                   10                  15

Leu Thr Leu Thr Cys Thr Val Ser
            20

<210> SEQ ID NO 36
<211> LENGTH: 24
<212> TYPE: PRT
<213> ORGANISM: Oryctolagus cuniculus

<400> SEQUENCE: 36

Gln Ser Leu Glu Glu Ser Gly Gly Gly Leu Phe Lys Pro Thr Asp Thr
1               5                   10                  15

Leu Thr Leu Thr Cys Thr Val Ser
            20

<210> SEQ ID NO 37
<211> LENGTH: 25
<212> TYPE: PRT
```

<213> ORGANISM: Oryctolagus cuniculus

<400> SEQUENCE: 37

Gln Glu Gln Gln Lys Glu Ser Glu Gly Gly Leu Phe Lys Pro Ala Asp
1               5                   10                  15

Thr Leu Thr Leu Thr Cys Thr Val Ser
            20                  25

<210> SEQ ID NO 38
<211> LENGTH: 24
<212> TYPE: PRT
<213> ORGANISM: Oryctolagus cuniculus

<400> SEQUENCE: 38

Gln Ser Val Lys Glu Ser Arg Gly Gly Leu Phe Lys Pro Thr Asp Thr
1               5                   10                  15

Leu Thr Leu Thr Cys Thr Val Ser
            20

<210> SEQ ID NO 39
<211> LENGTH: 24
<212> TYPE: PRT
<213> ORGANISM: Oryctolagus cuniculus

<400> SEQUENCE: 39

Gln Thr Val Lys Glu Ser Gly Gly Gly Leu Phe Lys Pro Ala Asp Thr
1               5                   10                  15

Leu Thr Leu Thr Cys Thr Val Ser
            20

<210> SEQ ID NO 40
<211> LENGTH: 24
<212> TYPE: PRT
<213> ORGANISM: Oryctolagus cuniculus

<400> SEQUENCE: 40

Gln Ser Val Lys Glu Ser Gly Gly Gly Leu Val Lys Pro Gly Gly Ser
1               5                   10                  15

Leu Thr Leu Thr Cys Thr Val Ser
            20

<210> SEQ ID NO 41
<211> LENGTH: 24
<212> TYPE: PRT
<213> ORGANISM: Oryctolagus cuniculus

<400> SEQUENCE: 41

Gln Ser Leu Gly Glu Ser Arg Gly Ser Leu Phe Lys Pro Ala Asp Thr
1               5                   10                  15

Leu Thr Leu Thr Cys Thr Val Ser
            20

<210> SEQ ID NO 42
<211> LENGTH: 17
<212> TYPE: PRT
<213> ORGANISM: Oryctolagus cuniculus

<400> SEQUENCE: 42

Val Ser Trp Val Arg Gln Ala Pro Gly Phe Gly Leu Asp Trp Ile Gly
1               5                   10                  15

Asn

```
<210> SEQ ID NO 43
<211> LENGTH: 17
<212> TYPE: PRT
<213> ORGANISM: Oryctolagus cuniculus

<400> SEQUENCE: 43

Val Ser Trp Val Arg Gln Ala Pro Gly Asn Gly Leu Asp Trp Ile Gly
1               5                   10                  15

Asn

<210> SEQ ID NO 44
<211> LENGTH: 17
<212> TYPE: PRT
<213> ORGANISM: Oryctolagus cuniculus

<400> SEQUENCE: 44

Val Ser Trp Val Arg Gln Ala Pro Gly Ile Gly Leu Asp Trp Ile Gly
1               5                   10                  15

Asn

<210> SEQ ID NO 45
<211> LENGTH: 17
<212> TYPE: PRT
<213> ORGANISM: Oryctolagus cuniculus

<400> SEQUENCE: 45

Val Ser Trp Val Arg Gln Ala Pro Gly Val Gly Leu Asp Trp Ile Gly
1               5                   10                  15

Asn

<210> SEQ ID NO 46
<211> LENGTH: 38
<212> TYPE: PRT
<213> ORGANISM: Oryctolagus cuniculus

<400> SEQUENCE: 46

Phe Tyr Ala Ser Trp Ala Lys Ser Arg Ser Thr Ile Thr Arg Asn Thr
1               5                   10                  15

Asn Glu Asn Thr Val Thr Leu Lys Met Thr Ser Leu Thr Ala Ala Asp
            20                  25                  30

Thr Ala Thr Tyr Phe Cys
            35

<210> SEQ ID NO 47
<211> LENGTH: 38
<212> TYPE: PRT
<213> ORGANISM: Oryctolagus cuniculus

<400> SEQUENCE: 47

Tyr Tyr Ala Ser Trp Ala Lys Ser Arg Ser Thr Ile Thr Arg Asn Thr
1               5                   10                  15

Asn Glu Asn Thr Val Thr Leu Lys Met Thr Ser Leu Thr Ala Ala Asp
            20                  25                  30

Thr Ala Thr Tyr Phe Cys
            35

<210> SEQ ID NO 48
<211> LENGTH: 38
<212> TYPE: PRT
<213> ORGANISM: Oryctolagus cuniculus
```

```
<400> SEQUENCE: 48

Phe Tyr Ala Arg Trp Ala Lys Ser Arg Ser Thr Ile Thr Arg His Thr
1               5                   10                  15

Asn Leu Asn Thr Val Thr Leu Lys Met Thr Ser Leu Thr Ala Ala Asp
            20                  25                  30

Thr Ala Thr Tyr Phe Cys
            35

<210> SEQ ID NO 49
<211> LENGTH: 38
<212> TYPE: PRT
<213> ORGANISM: Oryctolagus cuniculus

<400> SEQUENCE: 49

Tyr Tyr Ala Ser Trp Ala Lys Ser Arg Ser Thr Ile Thr Arg Asn Thr
1               5                   10                  15

Asn Leu Asn Thr Val Thr Leu Lys Met Thr Ser Leu Thr Ala Ala Asp
            20                  25                  30

Thr Ala Thr Tyr Phe Cys
            35

<210> SEQ ID NO 50
<211> LENGTH: 11
<212> TYPE: PRT
<213> ORGANISM: Oryctolagus cuniculus

<400> SEQUENCE: 50

Trp Gly Pro Gly Thr Leu Val Thr Val Ser Ser
1               5                   10

<210> SEQ ID NO 51
<211> LENGTH: 11
<212> TYPE: PRT
<213> ORGANISM: Oryctolagus cuniculus

<400> SEQUENCE: 51

Trp Gly Pro Gly Thr Pro Val Thr Val Ser Ser
1               5                   10

<210> SEQ ID NO 52
<211> LENGTH: 26
<212> TYPE: PRT
<213> ORGANISM: Oryctolagus cuniculus

<400> SEQUENCE: 52

Ala Ile Lys Met Thr Gln Thr Pro Ser Ser Val Ser Ala Ala Val Gly
1               5                   10                  15

Gly Thr Val Thr Ile Asn Cys Gln Ala Ser
            20                  25

<210> SEQ ID NO 53
<211> LENGTH: 26
<212> TYPE: PRT
<213> ORGANISM: Oryctolagus cuniculus

<400> SEQUENCE: 53

Ala Gln Val Met Thr Gln Thr Pro Ser Ser Val Ser Ala Ala Val Gly
1               5                   10                  15

Gly Thr Val Thr Ile Asn Cys Gln Ser Ser
            20                  25
```

```
<210> SEQ ID NO 54
<211> LENGTH: 26
<212> TYPE: PRT
<213> ORGANISM: Oryctolagus cuniculus

<400> SEQUENCE: 54

Ala Gln Val Leu Thr Gln Thr Pro Ser Ser Val Ser Ala Ala Val Gly
1               5                   10                  15

Gly Thr Val Thr Ile Asn Cys Gln Ala Ser
            20                  25

<210> SEQ ID NO 55
<211> LENGTH: 26
<212> TYPE: PRT
<213> ORGANISM: Oryctolagus cuniculus

<400> SEQUENCE: 55

Ala Gln Gly Leu Thr Gln Thr Pro Ser Ser Val Ser Ala Ala Val Gly
1               5                   10                  15

Gly Thr Val Thr Ile Asn Cys Gln Ala Ser
            20                  25

<210> SEQ ID NO 56
<211> LENGTH: 26
<212> TYPE: PRT
<213> ORGANISM: Oryctolagus cuniculus

<400> SEQUENCE: 56

Ala Leu Val Leu Thr Gln Thr Pro Ser Ser Val Ser Ala Ala Val Gly
1               5                   10                  15

Gly Thr Val Thr Ile Asn Cys Gln Ala Ser
            20                  25

<210> SEQ ID NO 57
<211> LENGTH: 26
<212> TYPE: PRT
<213> ORGANISM: Oryctolagus cuniculus

<400> SEQUENCE: 57

Ala Gln Gly Met Thr Gln Thr Pro Ser Ser Val Ser Ala Ala Val Gly
1               5                   10                  15

Gly Thr Val Thr Ile Asn Cys Gln Ala Ser
            20                  25

<210> SEQ ID NO 58
<211> LENGTH: 26
<212> TYPE: PRT
<213> ORGANISM: Oryctolagus cuniculus

<400> SEQUENCE: 58

Ala Leu Val Met Thr Gln Thr Pro Ser Ser Val Ser Ala Ala Val Gly
1               5                   10                  15

Gly Thr Val Thr Ile Asn Cys Gln Ala Ser
            20                  25

<210> SEQ ID NO 59
<211> LENGTH: 26
<212> TYPE: PRT
<213> ORGANISM: Oryctolagus cuniculus

<400> SEQUENCE: 59

Ala Ile Gln Met Thr Gln Thr Pro Ser Ser Val Ser Ala Ala Val Gly
1               5                   10                  15
```

-continued

Gly Thr Val Thr Ile Asn Cys Gln Ala Ser
            20                  25

<210> SEQ ID NO 60
<211> LENGTH: 17
<212> TYPE: PRT
<213> ORGANISM: Oryctolagus cuniculus

<400> SEQUENCE: 60

Leu Ser Trp Phe Gln Gln Lys Pro Gly Gln Pro Pro Lys Gln Leu Ile
1               5                   10                  15

Tyr

<210> SEQ ID NO 61
<211> LENGTH: 17
<212> TYPE: PRT
<213> ORGANISM: Oryctolagus cuniculus

<400> SEQUENCE: 61

Leu Ser Trp Phe Gln Gln Lys Pro Gly Gln Pro Pro Arg Gln Leu Ile
1               5                   10                  15

Tyr

<210> SEQ ID NO 62
<211> LENGTH: 17
<212> TYPE: PRT
<213> ORGANISM: Oryctolagus cuniculus

<400> SEQUENCE: 62

Leu Ser Trp Tyr Gln Gln Lys Pro Gly Gln Pro Pro Lys Gln Leu Ile
1               5                   10                  15

Tyr

<210> SEQ ID NO 63
<211> LENGTH: 36
<212> TYPE: PRT
<213> ORGANISM: Oryctolagus cuniculus

<400> SEQUENCE: 63

Asn Leu Ala Ser Gly Val Pro Ser Arg Phe Ser Gly Ser Gly Ser Gly
1               5                   10                  15

Thr Gln Phe Thr Leu Thr Ile Ser Ser Val Gln Cys Asp Asp Ala Ala
            20                  25                  30

Thr Tyr Tyr Cys
        35

<210> SEQ ID NO 64
<211> LENGTH: 36
<212> TYPE: PRT
<213> ORGANISM: Oryctolagus cuniculus

<400> SEQUENCE: 64

Asn Leu Ala Ser Gly Val Pro Ser Arg Phe Ser Gly Ser Gly Ser Gly
1               5                   10                  15

Thr Glu Phe Thr Leu Thr Ile Ser Ser Val Gln Cys Asp Asp Ala Ala
            20                  25                  30

Thr Tyr Tyr Cys
        35

<210> SEQ ID NO 65

```
<211> LENGTH: 36
<212> TYPE: PRT
<213> ORGANISM: Oryctolagus cuniculus

<400> SEQUENCE: 65

Asn Leu Ala Ser Gly Val Pro Ser Arg Phe Ser Gly Ser Gly Ser Gly
1               5                   10                  15

Thr Glu Phe Thr Leu Thr Ile Ser Asp Val Gln Cys Asp Asp Ala Ala
            20                  25                  30

Thr Tyr Tyr Cys
        35

<210> SEQ ID NO 66
<211> LENGTH: 36
<212> TYPE: PRT
<213> ORGANISM: Oryctolagus cuniculus

<400> SEQUENCE: 66

Asn Leu Ala Ser Gly Val Pro Ser Arg Phe Ser Gly Ser Gly Ser Gly
1               5                   10                  15

Thr Glu Phe Thr Leu Thr Ile Thr Ser Val Gln Cys Asp Asp Ala Ala
            20                  25                  30

Thr Tyr Tyr Cys
        35

<210> SEQ ID NO 67
<211> LENGTH: 36
<212> TYPE: PRT
<213> ORGANISM: Oryctolagus cuniculus

<400> SEQUENCE: 67

Asn Leu Ala Ser Gly Val Pro Ser Arg Phe Ser Gly Ser Gly Ser Gly
1               5                   10                  15

Ala Glu Phe Thr Leu Thr Ile Ser Ser Val Gln Cys Asp Asp Ala Ala
            20                  25                  30

Thr Tyr Tyr Cys
        35

<210> SEQ ID NO 68
<211> LENGTH: 36
<212> TYPE: PRT
<213> ORGANISM: Oryctolagus cuniculus

<400> SEQUENCE: 68

Asn Leu Ala Ser Gly Val Pro Ser Arg Phe Ser Gly Ser Gly Ser Gly
1               5                   10                  15

Thr Glu Phe Thr Leu Thr Ile Ser Ser Ala Gln Cys Asp Asp Ala Ala
            20                  25                  30

Thr Tyr Tyr Cys
        35

<210> SEQ ID NO 69
<211> LENGTH: 8
<212> TYPE: PRT
<213> ORGANISM: Oryctolagus cuniculus

<400> SEQUENCE: 69

Gln Ser Val Tyr Gly Lys Asn Tyr
1               5

<210> SEQ ID NO 70
```

```
<211> LENGTH: 12
<212> TYPE: PRT
<213> ORGANISM: Oryctolagus cuniculus

<400> SEQUENCE: 70

Ala Ser Glu Val Trp Gly Ser Arg Val Phe Asn Val
1               5                   10

<210> SEQ ID NO 71
<211> LENGTH: 7
<212> TYPE: PRT
<213> ORGANISM: Oryctolagus cuniculus

<400> SEQUENCE: 71

Ile Asn Glu Trp Gly Thr Leu
1               5

<210> SEQ ID NO 72
<211> LENGTH: 25
<212> TYPE: PRT
<213> ORGANISM: Oryctolagus cuniculus

<400> SEQUENCE: 72

Gln Glu Gln Leu Lys Glu Ser Gly Gly Gly Leu Phe Lys Pro Thr Asp
1               5                   10                  15

Thr Leu Thr Leu Thr Cys Thr Val Ser
            20                  25
```